(12) United States Patent
Vellard et al.

(10) Patent No.: US 7,531,341 B1
(45) Date of Patent: May 12, 2009

(54) COMPOSITIONS OF PROKARYOTIC PHENYLALANINE AMMONIA-LYASE AND METHODS OF USING COMPOSITIONS THEREOF

(75) Inventors: Michel Claude Vellard, Corte Madera, CA (US); Paul Andrew Fitzpatrick, Albany, CA (US); Emil D. Kakkis, Novato, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 64 days.

(21) Appl. No.: 11/451,999

(22) Filed: Jun. 12, 2006

(51) Int. Cl.
*C12N 9/88* (2006.01)
*A61K 38/00* (2006.01)
(52) U.S. Cl. ..................... 435/232; 530/345
(58) Field of Classification Search .................. 435/232
See application file for complete search history.

(56) References Cited

U.S. PATENT DOCUMENTS

| | | |
|---|---|---|
| 4,252,822 A | 2/1981 | Berry |
| 4,562,151 A | 12/1985 | Kishore |
| 5,166,322 A | 11/1992 | Shaw et al. |
| 5,206,344 A | 4/1993 | Katre et al. |
| 5,690,929 A | 11/1997 | Lishko et al. |
| 5,753,487 A | 5/1998 | Eigtved et al. |
| 5,766,897 A | 6/1998 | Braxton |
| 5,981,239 A | 11/1999 | Liu |
| 6,057,292 A | 5/2000 | Cunningham et al. |
| 6,312,939 B1 | 11/2001 | Roberts et al. |
| 6,433,158 B1 | 8/2002 | Pettit |
| 6,451,986 B1 | 9/2002 | Pettit |
| 6,461,849 B1 | 10/2002 | Olsen et al. |
| 6,548,644 B1 | 4/2003 | Pettit |
| 6,586,398 B1 | 7/2003 | Kinstler et al. |
| 6,686,164 B1 | 2/2004 | Olsen et al. |
| 6,737,259 B1 | 5/2004 | Clark et al. |
| 2002/0052038 A1 | 5/2002 | Roberts et al. |
| 2002/0102712 A1 | 8/2002 | Yoshida et al. |
| 2003/0082238 A1 | 5/2003 | Babich et al. |
| 2007/0048855 A1 | 3/2007 | Gamez et al. |
| 2008/0008695 A1 | 1/2008 | Vellard et al. |
| 2009/0038023 A1 | 2/2009 | Weiner et al. |

FOREIGN PATENT DOCUMENTS

| | | |
|---|---|---|
| WO | WO 90/12874 A2 | 11/1990 |
| WO | WO 03/072743 A2 | 9/2003 |
| WO | WO 2004/044169 A2 | 5/2004 |
| WO | WO 2006/034373 | 3/2006 |
| WO | WO 2008/069958 | 6/2008 |
| WO | WO 2008/153776 | 12/2008 |

OTHER PUBLICATIONS

Molineux, G., Pegylation: Engineering Improved Pharmaceuticals for Enhanced Therapy. Cancer Treatment Reviews. 2002. vol. 28, Supplement A, pp. 13-16.*
Moffitt et al. Discovery of Two Cyanobacterial Phenylalanine Ammonia Lyase: Kinetic and Structural Characterization. Biochemistry, Jan. 05, 2007 (web pub.), vol. 46, pp. 1004-1012.*
Christiansen et al. The Role of the MoFe protein alpha-125-Phe and beta-125-Phe Residues in *Azotobacter vinelandii* MoFe-Fe protein Interaction. Journal of Inorganic Biochemistry. 2000, vol. 80, pp. 195-204.*
Sorlie et al. Mechanistic Features and Structure of the Nitrogenase alpha-Gln-195 MoFe protein. Biochemistry. 2001, vol. 40, pp. 1540-1549.*
Request for publication date of Xiang et al. (cited on IDS from May 25, 2007) and Fax from Director of publications for the Journal of Microbiology verifying full text availability date as Jun. 3, 1995.*
Abell et al., "An In Vivo Evaluation of the Chemotherapeutic Potency of Phenylalanine Ammonia-Lyase," Cancer Research, Oct. 1973, pp. 2529-2532, vol. 33.
Abell et al., "Phenylalanine Ammonia-Lyase from the Yeast *Rhodotorula glutinis*,"Methods in Enzymology, 1987, pp. 242-253, vol. 142.
Abrams et al., "Rational Antigen Modification as a Strategy to Upregulate or Downregulate Antigen Recognition," Current Opinion Immunology, 2000, pp. 85-91, vol. 12.
Alunni et al., "Mechanisms of Inhibitions of Phenylalanine Ammonia—Lyase by Phenol Inhibitors and Phenol/Glycine Synergistic Inhibitors," Archives of Biochemistry and Biophysics, 2003, pp. 170-175, vol. 412.
Ambrus et al., "Depletion of Phenylalanine in the Blood of Phenylketonuric Patents Using a PAL-Enzyme Reactor, an In Virto Study," Research Communications in Chemical Pathology and Pharmacology, Jun. 1982, pp. 105-111, vol. 37, No. 1.
Ambrus et al., "Extracorporeal Enzyme Reactors for Depletion of Phenylalanine in Phenylketonuria," Annals of Internal Medicine, 1987, pp. 531-537, vol. 106.
Ambrus et al., "In Vivo Safety of Hollow Fiber Enzyme-Reactors with Immobilized Phenylalanine Ammonia-Lyase in a Large Animal Model for Phenylketonuria," The Journal Pharmacology and Experimental Therapeutics, 1983, pp. 598-602, vol. 224, No. 3.
Ambrus et al., "Phenylalanine Depletion for the Management of Phenylketonuria: Use Enzyme Reactors with Immobilized Enzymes," Science, Sep. 1978, pp. 837-839, vol. 201.

(Continued)

*Primary Examiner*—Suzanne M. Noakes
(74) *Attorney, Agent, or Firm*—Jones Day

(57) ABSTRACT

The present invention is directed to phenylalanine ammonia lyase (PAL) produced by prokaryotes, wherein such prokaryotic PAL wherein the PAL variant has a greater phenylalanine-converting activity as compared to a wild-type PAL. The invention thus provides compositions of bacterial PAL and biologically active fragments, mutants, variants and analogs thereof, as well as methods for the production, purification, and use of such compositions for therapeutic and industrial purposes.

6 Claims, 10 Drawing Sheets

OTHER PUBLICATIONS

Baedeker et al., "Structures of two Histidine Ammonia-Lyase Modifications and Implications for the Catalytic Mechanism," European Journal of Biochemistry, 2002, pp. 1790-1797, vol. 269.

Becker et al., "Cloning, Sequencing, and Biochemical Characterization of the Nostocyclopeptide Biosynthetic Gene Cluster: Molecular Basis for Imine Macrocyclization," Gene, 2004, pp. 35-42, vol. 325.

Bezanson et al., "Biosynthesis of Cinnamamide and Detection of Phenylalanine Ammonia-Lyase in Streptomyces Verticillatus," Canadian Journal of Microbiology, 1970, pp. 147-151, vol. 16.

Billett et al., "A Specific and reversible Macromolecular Inhibitor of Phenylalanine Ammonia-Lyase and Cinnamic Acid-4-Hydroxylase in Gherkins," Biochim. Biophys. Acta., May 1978, pp. 219-230, vol. 524.

Bourget et al., "Artificial Cell-Microencapsulated Phenylalanine Ammonia-Lyase," Applied Biochemistry and Biotechnology, 1984, pp. 57-59, vol. 10.

Bourget et al., "Phenylalanine Ammonia-Lyase Immobilized in Semipermeable Microcapsules for Enzyme Replacement in Phenylketonuria," Federation of European Biochemical Societies Letters, Jan. 1985, pp. 5-8, vol. 180, No. 1.

Bourget et al., "Phenylalanine Ammonica-Lyase Immobilized in Microcapsules for the Depletion of Phenylalanine in Plasma in Phenylketonuric Rat Model," Biochimica et Biophysica Acta, 1986, pp. 432-438, vol. 883.

Brannigan et al., "Protein Engineering 20 Years On," Nature Reviews, Molecular Cell Biology, Dec. 2002, pp. 964-970, vol. 3.

Calabrase et al., "Crystal Structure of Phenylalanine Ammonia-Lyase: Multiple Helix Dipoles Implicated in Catalysis," Biochemistry, Sep. 2004, pp. 11403-11416, vol. 43, No. 36, American Chemical Society.

Chang et al., "A New Theory of Enterorecirculation of Amino Acids and Its Use for Depleting Unwanted Amino Acids Using Oral Enzyme-Artificial Cells, as in Removing Phenylalanine in Phenylketonuria," Art. Cells Blood Subs. and Immob. Biotech., 1995, pp. 1-21, vol. 23, No. 1.

Chang et al., "Procedures for Microencapsulation of Enzymes, Cells and Genetically Engineered Microorganisms," Molecular Biotechnology, 2001, pp. 249-260, vol. 17.

Chen et al., "Tuning the Activity of an Enzyme for Unusual Environments: Sequential Random Mutagenesis of Subtilism E for Catalysis in Dimethylformamide,"Proc. Natl. Acad. Sci. U.S.A., Jun. 1993, pp. 5618-5622, vol. 90.

Chirino et al., "Minimizing the Immunogenicity of Protein Therapeutics," Drug Discovery Today, Jan. 2004, pp. 82-90, vol. 9, No. 2.

D'Agostino, "Tetrahydrobiopterin and Mild Phenylketonuria," New England Journal of Medicine, pp. 1723-1724, vol. 348 (To the Editor). 2003.

Davis, "Biochemistry. Mimicking Posttranslational Modifications of Proteins,"Science, Jan. 2003, pp. 480-482, vol. 303.

Delgado et al., "The Uses and Properties of PEG-Linked Proteins," Critical Reviews in Therapeutic Drug Carriers Systems, 1992, pp. 249-304, vol. 9, No. 3-4.

Egrie et al., "Development and Characterization of Novel Erythropoiesis Stimulating Protein (NESP),"British Journal of Cancer, 2001, pp. 3-10, vol. 84, (Supplement 1).

Fritz et al., "Phenylalanine Ammonia-Lyase," The Journal of Biological Chemistry, Aug. 10, 1976, pp. 4646-4650, vol. 251, No. 15.

Gamez et al., "Developmet of Pegylated Forms of Recombinant Rhodosporidium Toruloides Phenylalanine Ammonia-Lyase for the Treatment of Classical Phenylketonuria," Molecular Theory, Jun. 2005, pp. 986-989, vol. 11, No. 6, The American Society of Gene Therapy.

Gilbert et al., "The Effect of Proteinase on Phenylalanine Ammonia-Lyase from the Yeast Rhodotorula Glutinism," Biochem. J., 1981, pp. 715-723, vol. 199.

Gilbert et al., "Protection of Phenylalanine Ammonia-Lyase from Proteolytic Attack," Biochemical and Biophysical Research Communications, Sep. 16, 1985, pp. 557-563, vol. 131, No. 2.

Goodson et al., "Site-Directed Pegylation of Recombinant Interleukin-2 at Its Glycosylation Site," Biotechnology, Apr. 1990, pp. 343-346, vol. 8.

Graham, "Pegaspargase: A Review of Clinical Studies," Advanced Drug Delivery Reviews, 2003, pp. 1293-1302, vol. 55.

Greenwald et al., "Effective Drug Delivery by PEGylated Drug Conjugates," Advanced Drug Delivery Reviews, 2003, pp. 217-250, vol. 55.

Harris et al., "Effect of Pegylation on Pharmaceuticals," Nature Reviews, Drug Discovery, Mar. 2003, pp. 214-221, vol. 2.

Hedstrom et al., "Converting Trypsin to Chymotrysin: The Role of Surface Loops," Science, Mar. 6, 1992, pp. 1249-1254, vol. 255, No. 5049.

Hermeling et al., "Structure-Immunogenicity Relationships of Therapeutic Proteins," Pharmaceutical Research, Jun. 2004, pp. 897-903, vol. 21, No. 6.

Hershfield, Enzyme Replacement Therapy of Adenosine Deaminase Deficiency with Polyethylene Glycol-Modified Adenosine Deaminase (PEG-ADA), Immunodeficiency, 1993, pp. 93-97, vol. 4.

Hershfield et al., "Use of Site-Directed Mutagenesis to Enhance the Epitope-Shielding Effect of Covalent Modification of Proteins with Polyethylene Glycol," Proc. Natl. Acad. Sci. USA, Aug. 1991, pp. 7185-7189, vol. 88.

Hill et al., "Investigation of the Early Steps in Soraphen A Biosynthesis," Chemical Communications, 2003, pp. 1358-1359.

Hoffman et al., "Sequence Analysis and Biochemical Characterization of the Nostopeptolide A Biosynthetic Gene Cluster from Nostoc sp. GSV224," Gene, 2003, pp. 171-180, vol. 311.

Hoffman et al., "Recent Advances in the Application of Expressed Protein Ligation to Protein Engineering,"Current Opinion in Biotechnology, Aug. 2002, pp. 297-303, vol. 13, No. 4.

Hopfner et al., "New Enzyme Lineages by Subdomain Shuffling," Proc. Natl. Acad. Sci., USA, Aug. 1998, pp. 9813-9818, vol. 95.

Hoskins et al., "Enzymatic Control of Phenylalanine Intake in Phenylketonuria," The Lancet, Feb. 23, 1980, pp. 392-394.

Hoskins et al., "The Metabolism of Cinnamic Acid by Healthy and Phenylketonuric Adults: a Kinetic Study," Biomedical Mass Spectrometry, 1984, pp. 296-300, vol. 11, No. 6.

Hoskins et al., "Phenylalanine Ammonia Lyase in the Management of Phenylketonuria: The Relationship Between Ingested Cinnamate and Urinary Hippurate in Humans," Research Communications in Chemical Pathology and Pharmacology, Feb. 1982, pp. 275-282, vol. 35, No. 5.

Ikeda et al., "Phenylalanine Ammmonia-Lyase Modified with Polyethylene Glycol: Potential Therapeutic Agent for Phenylketonuria," Amino Acids, Nov. 2005, pp. 283-287, vol. 29, No. 3., Springer-Verlag, Vienna, Austria.

International Search Report and Written Opinion, PCT/US2005/033895, Sep. 5, 2006.

Kalaitzis et al., "Mutasynthesis of Enterocin and Wailupermycin Analogues," Journal of the American Chemical Society, 2003, pp. 9290-9291, vol. 125.

Kalghatgi et al., "Multitubular Reactors with Immobilized L-Phenylalanine Ammonia-Lyase for Use in Extracorporeal Shunts," Research Communications in Chemical Pathology and Pharmacology, Mar. 1980, pp. 551-561, vol. 26, No. 3.

Kim et al., "Trends in Enzyme Therapy for Phenylketonuria," Molecular Therapy, Aug. 2004, pp. 220-224, vol. 10, No. 2.

Kinstler et al., "Characterization and Stability of N-Terminally PEGylated rhG-CSF," Pharmaceutical Research, 1996, pp. 996-1002, vol. 13, No. 7.

Koch et al., "Large Neutral Amino Acid Therapy and Phenylketonuria: a Promising Approach to Treatment," Molecular Genetics and Metabolism, 2003, pp. 110-113, vol. 79.

Koukol et al., "The Metabolism of Aromatic Compounds in Higher Plants," The Journal of Biological Chemistry, Oct. 1961, pp. 2692-2698, vol. 236, No. 10.

Kriwacki et al., "Combined Use of Proteases and Mass Spectrometry in Structural Biology," Journal of Biomolecular Techniques, Sep. 1998, pp. 5-15, vol. 9, No. 3.

Kyndt et al., "Characterization of a Bacterial Tyrosine Ammonia Lyase, a Biosynthetic Enzyme for the Photoactive Yellow Protein," Federation of European Biochemical Societies Letters, 2002, pp. 240-244, vol. 512.

Langer et al., "Identification of Essential Amino Acids Phenylalanine Ammonia-Lyase by Site-Directed Mutagenesis," Biochemistry, Sep. 1997, pp. 10867-10871, vol. 36.

Langer et al., "Methylidene-Imidazole (MIO) from Histidine and Phenylalanine Ammonia-Lyase," Advances in Protein Chemistry, 2001, pp. 175-188, vol. 58.

Larue et al., "An Extracorporeal Hollow-Fiber Reactor for Phenylketonia Using Immobilized Phenylalanine Ammonia Lyase," Dev. Pharmacol. Ther., 1986, pp. 73-81, vol. 9.

Lazar et al., "Designing Proteins for Therapeutic Applications," Current Opinion in Structural Biology, 2003, pp. 513-518, vol. 13.

Lee et al., "N-Terminal Site-Specific Mono-PEGylation of Epidermal Growth Factor," Pharmaceutical Research, May 2003, pp. 818-825, vol. 20, No. 5.

Leong et al., Adapting Pharmacokinetic Properties of a Humanized Anti-Interleukin-8 Antibody for Therapeutic Applications using Site-Directed Pegylation, Cytokine, Nov. 2001, pp. 106-119, vol. 16, No. 3.

Levy, "Phenylketonuria: Old Disease, New Approach to Treatment," Proc. Natl. Acad. Sci. USA, Mar. 1999, pp. 1811-1813, vol. 96.

Liu et al., "Study on a Novel Strategy to Treatment of Phenylketonuria," Art. Cells. Blood Subs. Immob. Biotech., 2002, pp. 243-257, vol. 30, No. 4.

Lu et al., "Pegylation: a Method for Assessing Ttopological Accessibilities in Kv1.3," Biochemistry, Nov. 2001, pp. 13288-13301, vol. 40.

Lucke et al., "BH4-Sensitive Hyperphenylalaninemia: New Case and Review of Literature," Pediatric Neurology, 2003, pp. 228-230, vol. 28, No. 3.

Marconi et al., "Phenylalanine Ammonia-Lyase Entrapped in Fibers," Biochemie, 1980, pp. 575-580, vol. 62.

Marshall et al., "Rational Design and Engineering of Therapeutic Proteins," Drug Discovery Today, Mar. 2003, pp. 212-221, vol. 8, No. 5.

Matalon et al., "Bioterin Responsive Phenylalanine Hydroxylase Deficiency," Genetics in Medicine, Jan./Feb. 2004, pp. 27-32, vol. No. 1.

Maverakis et al., Autoreactive T Cells can be Protected from Tolerance Induction Through Competition by Flanking Determinants for Access to Class II MHC, Proceedings of the National Academy of Sciences USA, Apr. 2003, pp. 5342-5347, vol. 100, No. 9.

Mehvar, "Modulation of the Pharmacokinetics and Pharmacodynamics of Proteins by Polyethylene Glycol Conjugation," J. Pharmaceut. Sci., 2000, pp. 125-136, vol. 3, No. 1.

Meyer et al., "Reduced Antibody Response to Streptavidin Through Site-Directed Mutagenesis," Protein Science, 2001, pp. 491-503, vol. 10.

Moola et al., "Erwinia Chrysanthemi L-Aspariginase: Epitope Mapping and Production of Antigenically Modified Enzymes," Biochemical Journal 1994, pp. 921-927, vol. 302, No. Part 3, Portland Press, London, Great Britain.

Moore, "Biosynthesis of Marine Natural Products: Microorganisms (Part A)," Natural Products Reports, 2005, pp. 580-593, vol. 22.

National Institutes of Health, "Phenylketonuria (PKU): Screening and Management," NIH Consensus Statement, Oct. 2000, pp. 1-33, vol. 17, No. 3.

Parkinson et al., "Pegvisomant in the Treatment of Acromegaly," Advanced Drug Delivery Reviews, 2003, pp. 1303-1314, vol. 55.

Pederson et al., "Preperation of Immobilized L-Phenylalanine Ammonia-Lyase in Tubular Form for Depletion of L-Phenylalanine," Research Communications in Chemical Pathology and Pharmacology, Jun. 1978, pp. 559-569, vol. 20, No. 3.

Pettit et al., "Structure-Function Studies of Interleukin 15 Using Site-Specific Multigenesis, Polyethylene Glycol Conjugation, and Homology Modeling," The Journal of Biological Chemistry, Jan. 24, 1997, pp. 2312-2318, vol. 272, No. 4.

Poppe et al., "Friedel-Crafts-Type Mechanism for the Enzymatic Elimination of Ammonia from Histidine and Phenylalanine," Angewandte Chemie Int. Ed., 2005, pp. 3668-3688, vol. 44.

Poppe et al., "Methylidene-Imidazolone: a Novel Electrophile for Substrate Activation,"Current Opinion in Chemical Biology, 2001, pp. 512-524, vol. 5.

Poppe et al., "Properties and Synthetic Applicationa of Ammonia-Lyases," Current Organic Chemistry, 2003, pp. 1297-1315, vol. 7.

Rao et al., "Degradation of Aromatic Amino Acids by Fungi," Canadian Journal of Biochemistry, 1967, pp. 1863-1872, vol. 45.

Reddy et al., "Use of Peginterferon alfa-2a (40 KD) (Pegasys ®) for the Treatment of Hepatitis C," Advanced Drug Delivery Reviews, 2002, pp. 571-586, vol. 54.

Roberts et al., "In Vivo Effects of Phenylalanine Ammmonia-Lyase,"Cancer Treatment Reports, Mar. 1976, pp. 261-263, vol. 60, No. 3.

Rother et al., "Characterization of the Active Site of Histidine Ammonia-Lyase from Pseudomonas Putida," European Journal of Biochemistry, 2001, pp. 6011-6019, vol. 268.

Rother et al., "An Active Site Homology Model of Phenylalanine Ammonia-Lyase from Petroselinum Crispum," European Journal of Biochemistry, 2002, pp. 3065-3075, vol. 269.

Russell et al., "Recombinant Proteins for Genetics Disease," Clin. Genet., 1999, pp. 389-394, vol. 55.

Sarkissian et al., "A Different Approach to Treatment of Phenylketonuria: Phenylalanine Degradation with recombinant Phenylalanine Ammonia Lyase," Proceedings of the National Academy of Science USA, Mar. 1999, pp. 2339-2344, vol. 96.

Sarkissian et al., "A Heteroallelic Mutant Mouse Model: A New Orthologue for Human Hyperphenylalaninemia," Molecular Genetics and Metabolism, 2000, pp. 188-194, vol. 69.

Schuster et al., "Serine-202 is the Putative Precursor of the Active Site Dehydroalanine of Phenylalanine Ammonia Lyase. Site-directed Mutagenesis Studies on the Enzyme from Parsley (*Petroselinum crispum* L.)," Federation of European Biochemical Societies Letters, Aug. 1994, pp. 252-254, vol. 349.

Schuster et al., "The Mechanism of Action of Phenylalanine Ammonia-Lyase: The Role of Prosthetic Dehyroalanine," Proceedings of the National Academy Sciences USA, Aug. 1995, pp. 8433-8437, vol. 92.

Schwede et al., "Crystal Structure of Histidine Ammonia-Lyase Revealing a Novel Polypeptide Modification as the Catalytic Electrophile," Biochemistry, 1999, pp. 5355-5361, vol. 38.

Shen et al., "Biochemical Properties and Immunogenicity of L-Phenylalanine Ammonia-Lyase: Effects on Tumor-Bearing Mice," Cancer Treatment Reports, Jun. 1979, pp. 1063-1068, vol. 63, No. 6.

Shen et al., "Clearance of Phenylalanine Ammonia-Lyase from Normal and Tumor-Bearing Mice," Cancer Research, Apr. 1977, pp. 1051-1056, vol. 37.

Spaapen et al., "Tetrahydrobiopterin-Responsive Phenylalanine Hydroxylase deficiency, State of the Art," Molecular Genetics and Metabolism, 2002, pp. 93-99, vol. 78.

Spencer et al., "A Strategy for Mapping and Neutralizing Conformation Immunogenic Sites on Protein Therapeutics," Proteomics, Mar. 2002, pp. 271-279, vol. 2, No. 3, Wiley-VCH Verlag, Weinheim.

Suchi et al., "Molecular Cloning of a cDNA Encoding Human Histidase," Biochimica et Biophysica Acta, 1993, pp. 293-295, vol. 1216.

Tangri et al., "Rationally Engineered Proteins of Antibodies with Absent or Reduced Immunogenicity," Current Medical Chemistry, 2002, pp. 2191-2199, vol. 9.

Taylor et al., "Cloning and Expression of Rat Histidase," The Journal of Biological Chemistry, Oct. 25, 1990, pp. 18192-18199, vol. 265, No. 30.

Taylor et al., "Site-Directed Mutegenesis of Conserved Serines in Rat Histidase," Journal of Biological Chemistry, Nov. 1994, pp. 27473-27477, vol. 269, No. 44.

Veronese et al., "Branched and Linear Poly(Ethylene Glycol): Influence of the Polymer Structure on Enzymological Pharmacokineti, and Immunological Properties of Protein Conjugates," Journal of Bioactive and Compatible Polymers, 1997, pp. 196-207, vol. 12.

Veronese et al., "Introduction and Overview of Peptide and Pegylation," Advanced Drug Delivery Reviews 2002, pp. 453-456, vol. 54(4).

Wang et al., "New Carbohydrate-Based Materials for the Stabilization of Proteins," Journal of the American Chemical Society, 1992, pp. 378-380, vol. 114.

Wang et al., "New Preparation for Oral Administration of Digestive Enzyme. Lactose Complex Microcapsules," Biomat. Art. Cells Immob. Biotech., 1993, pp. 637-646, vol. 21, No. 5.

Wang et al., "Structural and Biological Characterization of Pegylated Recombinant Interferon alpha-2b and Its Therapeutic Implications," Advanced Drug Delivery Reviews, 2002, pp. 547-570, vol. 54.

Wang et al., "Structure-Based Chemical Modifications Strategy for Enzyme Replacement Treatment of Phenylketonuria," Molecular Genetics and Metabolism, Sep. 2005, pp. 134-140, vol. 86, No. 1-2, Academic Press, San Diego, CA.

Whittle et al., "Protein Structure-Based Drug Design," Annual review of Biophysics and Biomolecular Structure, 1994, pp. 349-375, vol. 23, Annual Review Inc., Palo Alto, CA.

Weider et al., "Some Properties of Polyethylene Glycol: Phenylalanine Ammonia-Lyase Adducts," The Journal of Biological Chemistry, Dec. 25, 1979, pp. 12579-12587, vol. 254, No. 24.

Wilks et al., "Design of a Specific Phenyllactate Dehydrogenase by Peptide Loop Exchange on the Bacillus Stearothermophilus Lactate Dehydrogenase Framework," Biochemistry, 1992, pp. 7802-7806, vol. 31.

Williams et al., "The Gene sltA Encodes a Phenylalanine Ammonia-Lyase That is Involved in the Production of a Stilbene Antibiotic in Photorhabdus Luminescens TT01," Microbiology, 2005, pp. 2543-2550, vol. 151.

Woolf et al., "The Dietary Treatment of Phenylketonuria," Archives Disease in Childhood, 1958, pp. 31-45, vol. 33.

Xiang et al., "Inactivation, Complementation, and Heterologous Expression of encP, a Novel Bacterial Phenylalanine Ammonia-Lyase Gene," Journal of Biological Chemistry, Sep. 2002, pp. 32505-32509, vol. 277, No. 36.

Xiang et al., "Biochemical Characterization of a Prokaryotic Phenylalanine Ammonia Lyase," Journal of Bacteriology, Jun. 2005, pp. 4286-4289, vol. 187, No. 12.

Xiang et al., "Biochemical Characterization of a Prokaryotic Phenylalanine Ammonia Lyase," Journal of Bacteriology, Jul. 2006, p. 5331, vol. 188, No. 14 (Author's Correction).

Yeung et al., "Elimination of an Immunodominant CD4+ T Cell Epitope in Human IFN-β Does Not Result in an In Vivo Response Directed at the Subdominant Epitope," Journal of Immunology, 2004, pp. 6658-6665, vol. 172.

Yoshioka et al., "Optimal Site-Specific PEGylation of Mutant TNF-α Improves Its Antitumor Potency," Biochemical and Biophysical Research Communications, 2004, pp. 808-814, vol. 315.

Zon et al., "Inhibitors of Phenylalanine Ammonia-Lyase: 1-Aminobenzylphosphonic Acids Substituted in the benzene ring," Phytochemistry, Jan. 2002, pp. 9-21, vol. 59.

U.S. Appl. No. 61/055,946, filed May 23, 2008, Fitzpatrick et al.
U.S. Appl. No. 61/066,125, filed Aug. 17, 2007, Vellard et al.
U.S. Appl. No. 61/084,961, filed Jul. 30, 2008, Foehr et al.
U.S. Appl. No. 12/107,736, filed Apr. 22, 2008, Kakkis et al.
U.S. Appl. No. 12/107,731, filed Apr. 22, 2008, Kakkis et al.

Abell et al., "The Effects of Phenylalanine Ammonia-Lyase on Leukemia Lymphocytes in Vitro." Cancer Research 32:285-290 (1972).

Chi et al., "Physical Stability of Proteins in Aqueous Solution: Mechanism and Driving Forces in Nonnative Protein Aggregation," Pharmaceutical Research, 20(9): 1325-1336 (2003).

Da Cunha, "Purification, Characterization and Induction of L-Phenylalanine Ammonia-Lyase in Phaseolus Vulgaris," European Journal of Biochemistry, 178:243-248 (1988).

Dengler, et al., "Development of a Propidium Iodide Fluorescence Assay for Proliferation and Cytotoxicity Assays," Anti-Cancer Drugs, 6:522-532 (1995).

Elstad et al., "Modulation of B16-BL6 Murine Melanoma Metastatic Phenotype by Tyrosine and Phenylalanine Restriction in the Absence of Host Selection Pressures," Anticancer Research, 13:523-528 (1993).

Elstad et al., "Tyrosine and Phenylalanine Restriction Sensitizes Adriamycin-Resistant P388 Leukemia Cells to Adriamycin," Nutrition and Cancer, 25:47-60 (1996).

Fu et al., "Influence of Tyrosine and Phenylalanine Limitation on Cytoxicity of Chimeric TGF-α Toxins on B16BL6 Murine Melanoma in Vitro," Nutrition and Cancer, 31(1):1-7 (1998).

Fu et al., "Focal Adhesion Kinase-Dependent Apoptosis of Melanoma Induced Tyrosine and Phenylalanine Deficiency," Cancer Research, 59:758-765 (1999).

Fu et al., "Specific Amino Acid Dependency Regulates Invasiveness and Viability of Androgen-Independent Prostate Cancer Cells," Nutrition and Cancer, 45(1):60-73 (2003).

Fu et al., "Selective Amino Acid Restriction Targets Mitochondria to Induce Apoptosis Androgen- Independent Prostate Cancer Cells," Journal of Cellular Physiology, 209:522-534 (2006).

Holden et al., "Chorismate Lyase: Kinetics and Engineering for Stability," Biochim. Biophys. Acta, 1594:160-167 (2002).

International Search Report and Written Opinion for PCT/US2008/006661 (WO2008/153776) dated Nov. 12, 2008.

Kim et al., "Trends in Enzyme Therapy in Phenylketonuria," Molecular Therapy, 10(2):220-224 (2004).

Kreitman, "Immunotoxins for Targeted Cancer Therapy," The AAPS Journal, 8(3):E532-E551 (2006).

Meadows et al., "Dietary Influence of Tyrosine and Phenylalanine on the Response of B16 Melanoma to Carbidopa-Levodopa Methyl Ester Chemotherapy," Cancer Res., 42:3056-3063 (1982).

Nunez et al., "PPAR-γ Ligands and Amino Acid Deprivation Promote Apoptosis of Melanoma, Prostate, and Breast Cancer Cells," Cancer Letters, 236:113-141 (2006).

Pilbak et al., "The Essential Tyrosine-Containing Loop Conformation and the Role of the C-Terminal Multi-Helix region in Eukaryotic Phenylalanine Ammonia-Lyases," FEBS Journal, 273:1004-1019 (2006).

Schellekens, "Factors Influencing the Immunogenicity of Therapeutic Proteins," Nephrology Dialysis Transplantation, 20( Suppl. 6):vi3-vi9 (2005).

Shen et al., "Total-Body Radiation Suppression of the Clearance of Phenylalanine Ammonia-Lyase from Mouse Plasma," Journal of the Reticuloendothelial Society, 23(3):167-175 (1978).

Stith et al., "Effects of Phenylalanine Ammonia-Lyase and Phenylalanine Deprivation on Murine Leukemic Lymphoblasts in vitro," Cancer Research, 33:966-971 (1973).

Vellard, "The Enzyme as Drug: Application of Enzymes as Pharmaceuticals," Current Opinion in Biotechnology, 14:1-7 (2003).

Watts et al., "Discovery of Substrate Selectivity Switch in Tyrosine Ammonia-Lyase, a Member of the Aromatic Amino Acid Lyase Family," Chemistry and Biology, Current Biology (London, GB) vol. 13, No. 12, pp. 1317-1326 (Dec. 26, 2006).

Wang et al., Structural and biochemical characterization of the therapeutic Anabaena variabilis phenylalanine ammonia lyase,: J. Mol. Biol. 380:623-635 (2008).

Office Action for U.S. Appl. No. 11/230,374 (U.S. Publ. No. 2007-0048855) dated Jun. 15, 2007.

Office Action for U.S. Appl. No. 11/230,374 (U.S. Publ. No. 2007-0048855) dated Nov. 30, 2007.

Notice of Allowance for U.S. Appl. No. 11/230,374 (U.S. Publ. No. 2007-0048855) dated Jan. 10, 2008.

Office Action for U.S. Appl. No. 11/807,227 (U.S. Publ. No. 2008-0008695) dated Jan. 16, 2009.

Office Action for U.S. Appl. No. 12/107,736 dated Jan. 29, 2009.

Office Action for U.S. Appl. No. 12/107,731 dated Dec. 12, 2008.

* cited by examiner

FIGURE 1A
Gene Sequence of Nostoc punctiforme

```
   1    atgaatataa catctctaca acagaacata acgcgttctt ggcaaatacc tttcactaat
  61    agttcagatt caatcgtaac tgtaggcgat cgcaatctga caatcgacga ggttgtaaat
 121    gttgctcgtc atggaacaca ggtgcgctta actgataatg cagatgtcat tcggggtgtt
 181    caagcatctt gtgattacat taacaatgca gtcgaaacag cacagccaat ttacggggtg
 241    acatctggct tggcggtat ggcagatgtt gtcatctctc gcgaacaagc agcggaactt
 301    cagactaatt taatttggtt tctgaaatcc ggcgcaggaa acaaattatc gttagcagac
 361    gtgcgtgcag ctatgctctt acgtgcaaat tcacatttgt atggtgcgtc tggtatacga
 421    ctcgaactta ttcagcggat tgaaactttc ctcaacgctg gcgtgacacc ccatgtctat
 481    gagtttggct ctatcggtgc tagcggcgat ttggtgccat tatcctacat tactggggca
 541    ctaatcggtc tagatcctag ctttacagtt gacttcgacg gtaaagaaat ggatgccgtt
 601    acagccttgt ctcgtttggg tttgccaaag ttgcaattgc aaccgaaaga aggtttagca
 661    atgatgaatg gcacctcagt catgacaggt attgcagcta actgtgtgta cgatgcgaaa
 721    gttttgctcg ctctgacaat gggtgtacac gccttagcca tccaaggttt atacggaacg
 781    aatcaatctt tccacccgtt tattcatcag tgcaagccac atcccggtca actatggaca
 841    gcagatcaaa tgttttctct gctgaaagat tcatctttag ttcgtgaaga gttggatggt
 901    aaacacgaat accgtggtaa agatctgata caggatcgtt attctctccg ctgtctggca
 961    cagttcatag gccaatcgt tgatggggta tcagagatta ccaagcaaat cgaggtagaa
1021    atgaactcag tcaccgataa cccattgatt gatgtcgaga accaagttag ttatcacggc
1081    ggcaattttc tcggacagta tgtgggtgtg acaatggatc gcctacgtta ttacataggg
1141    ctattggcca aacacatcga tgtgcagatt gcacttcttg tctcgccaga gtttagcaac
1201    ggcttaccac cctctttagt tggtaatagc gatcgcaaag ttaatatggg actcaaaggt
1261    ttgcaaatca gtggaaactc gattatgcca ctgttgagct tctatggaaa ttccctagcc
1321    gatcgctttc ctacccacgc cgagcaattt aatcaaaata ttaacagcca aggctatatt
1381    tccgcaaatt tgacacgtcg ttccgtagac atatttcaga attatatggc gatcgcgttg
1441    atgtttggag ttcaagctgt tgacctccgc acatataaga tgaaaggtca ttatgatgca
1501    cgtacatgcc tctcacccaa tactgtgcag ttatacacag cagtctgcga ggtagttgga
1561    aagccactaa cgtctgtgcg tccatacatt tggaacgaca acgagcaatg tttagatgag
1621    catattgccc ggatttcagc tgatatcgct ggtggtggtt taattgtgca agcagttgag
1681    catatttttt cgagcttaaa gtcaacgtaa
```

FIGURE 1B

Protein Sequence of Nostoc punctiforme

MNITSLQQNITRSWQIPFTNSSDSIVTVGDRNLTIDEVVNVARH

GTQVRLTDNADVIRGVQASCDYINNAVETAQPIYGVTSGFGGMADVVISREQAAELQT

NLIWFLKSGAGNKLSLADVRAAMLLRANSHLYGASGIRLELIQRIETFLNAGVTPHVY

EFGSIGASGDLVPLSYITGALIGLDPSFTVDFDGKEMDAVTALSRLGLPKLQLQPKEG

LAMMNGTSVMTGIAANCVYDAKVLLALTMGVHALAIQGLYGTNQSFHPFIHQCKPHPG

QLWTADQMFSLLKDSSLVREELDGKHEYRGKDLIQDRYSLRCLAQFIGPIVDGVSEIT

KQIEVEMNSVTDNPLIDVENQVSYHGGNFLGQYVGVTMDRLRYYIGLLAKHIDVQIAL

LVSPEFSNGLPPSLVGNSDRKVNMGLKGLQISGNSIMPLLSFYGNSLADRFPTHAEQF

NQNINSQGYISANLTRRSVDIFQNYMAIALMFGVQAVDLRTYKMKGHYDARTCLSPNT

VQLYTAVCEVVGKPLTSVRPYIWNDNEQCLDEHIARISADIAGGGLIVQAVEHIFSSL

KST

FIGURE 2A
Gene Sequence of Anabaena variabilis

```
   1    atgaagacac tatctcaagc acaaagcaaa acctcatctc aacaattttc ttttactgga
  61    aattcttctg ccaatgtaat tattggtaat cagaaactca caatcaatga tgttgcaagg
 121    gtagcgcgta atggcaccct agtgtcttta accaataaca ctgatatttt gcagggtatt
 181    caggcatctt gtgattacat taataatgct gttgaatctg gggaaccaat ttatggagtg
 241    acatctggtt ttggcggtat ggccaatgtt gccatatccc gtgaacaagc atctgaactc
 301    caaaccaact tagtttggtt cctgaaaaca ggtgcaggga acaaattacc cttggcggat
 361    gtgcgcgcag ctatgctctt gcgtgcaaac tctcatatgc gcggtgcatc tggcatcaga
 421    ttagaactta tcaagcgtat ggagattttc cttaacgctg gtgtcacacc atatgtgtat
 481    gagtttggtt caattggtgc aagtggtgat ttagtgccac tatcctacat tactggttca
 541    ctgataggct tagatcccag ttttaaggtt gacttcaacg gtaaagaaat ggatgcgcca
 601    acagctctac gtcaactgaa tttgtcaccc ttgacattgt tgccgaagga aggcttggcg
 661    atgatgaacg gcacttcagt catgacaggt attgcagcaa actgcgtcta cgatactcaa
 721    attttaactg cgatcgctat gggcgttcac gctctagata tccaagcttt aaacggaacc
 781    aatcaatcat ccatccatt tatccataat tccaaaccac atcctggtca attatgggca
 841    gcagatcaga tgatttcttt gttagccaat tcccagttag ttcgtgatga gttagatggt
 901    aaacacgatt atcgtgatca cgagttgatt caagatcgtt actcactccg atgccttccc
 961    cagtatttgg ggccaatcgt tgatggaatt tccagattg ccaaacaaat tgaaatcgaa
1021    atcaactcag tcaccgataa cccactaatt gatgttgata accaagctag ctatcatgga
1081    ggaaatttcc tcggacagta cgtgggtatg ggaatggatc acctgcgtta ctatattggg
1141    ttattggcta aacacctaga tgtgcagatt gccctcctcg cctcaccaga gtttagcaat
1201    ggactaccac catctttatt aggcaaccga gaacgtaaag tcaatatggg actcaaaggt
1261    ctgcaaatat gcggtaactc aattatgcca ctgttgacct tctatggaaa ttccatcgcc
1321    gatcgctttc ctacccatgc agaacaattt aatcagaaca tcaacagtca aggatacact
1381    tcagcgactc tagcccgccg ttctgtggat atcttccaga attatgtggc gatcgctctg
1441    atgtttggag tccaagctgt tgacctccgc acatataaaa agactggtca ttacgatgca
1501    cgcgcctgtc tatcacctgc aactgagcgc ttatattcag cagtccgcca cgtagttgga
1561    caaaaaccaa cttcagatcg cccatatatt tggaatgata atgagcaagg actggatgag
1621    catattgccc ggatttctgc tgatatcgct gctggtggtg tgattgtgca agcagttcaa
1681    gatatcttac cctgcttgca ttaa
```

FIGURE 2B

Protein Sequence of Anabaena variabilis

```
  1    mktlsqaqsk tssqqfsftg nssanviign qkltindvar varngtlvsl tnntdilqgi
 61    qascdyinna vesgepiygv tsgfggmanv aisreqasel qtnlvwflkt gagnklplad
121    vraamllran shmrgasgir lelikrmeif lnagvtpyvy efgsigasgd lvplsyitgs
181    ligldpsfkv dfngkemdap talrqlnlsp ltllpkegla mmngtsvmtg iaancvydtq
241    iltaiamgvh aldiqalngt nqsfhpfihn skphpgqlwa adqmisllan sqlvrdeldg
301    khdyrdheli qdryslrclp qylgpivdgi sqiakqieie insvtdnpli dvdnqasyhg
361    gnflgqyvgm gmdhlryyig llakhldvqi allaspefsn glppsllgnr erkvnmglkg
421    lqicgnsimp lltfygnsia drfpthaeqf nqninsqgyt satlarrsvd ifqnyvaial
481    mfgvqavdlr tykktghyda raclspater lysavrhvvg qkptsdrpyi wndneqglde
541    hiarisadia aggvivqavq dilpclh
```

FIGURE 4

Alignment of cyanobacterial protein sequences of N. punctiforme PAL (SEQ ID NO:4) and A. variabilis (SEQ ID NO:2) with EncP PAL (SEQ ID NO:5) and P. putida HAL (SEQ ID NO:6). Active site residues which correspond to PAL or HAL activity are highlighted and underlined.

```
Avar03005300    MKTLSQAQSK TSSQQFSFTG NSSANVIIGN QKLTINDVAR VARNGTLVSL
Npun02008223    MNITSLQQNI TRSWQIPFTN SSDSIVTVGD RNLTIDEVVN VARHGTQVRL
EncP            .......... .......... ..MTFVIELD MNVTLDQLED AARQRTPVEL
PputidaHAL      .......... .......... ..MTELTLKP GTLTLAQLRA IHAAPVRLQL Avar03005300    TNNTDILQGI QASCDYINNA VESGEPIYGV TSGFGGMANV AISREQASEL
Npun02008223    TDNADVIRGV QASCDYINNA VETAQPIYGV TSGFGGMADV VISREQAAEL
EncP            S..APVRSRV RASRDVLVKF VQDERVIYGV NTSMGGFVDH LVPVSQARQL
PputidaHAL      D..ASAAPAI DASVACVEQI IAEDRTAYGI NTGFGLLAST RIASHDLENL Avar03005300    QTNLVWFLKT GAGNKLPLAD VRAAMLLRAN SHMRGASGIR LELIKRMEIF
Npun02008223    QTNLIWFLKS GAGNKLSLAD VRAAMLLRAN SHLYGASGIR LELIQRIETF
EncP            QENLINAVAT NVGAYLDDTT ARTIMLSRIV SLARGNSAIT PANLDKLVAV
PputidaHAL      QRSLVLSHAA GIGAPLDDDL VRLIMVLKIN SLSRGFSGIR RKVIDALIAL Avar03005300    LNAGVTPYVY EFGSIGASGD LVPLSYITGS LIGLDPSFKV DFNGKEMDAP
Npun02008223    LNAGVTPHVY EFGSIGASGD LVPLSYITGA LIGLDPSFTV DFDGKEMDAV
EncP            LNAGIVPCIP EKGSLGTSGD LGPLAAIALV CAGQW...KA RYNGQIMPGR
PputidaHAL      VNAEVYPHIP LKGSVGASGD LAPLATMSLV LLGEG...KA RYKGQWLSAT Avar03005300    TALRQLNLSP LTLLPKEGLA MMNGTSVMTG IAANCVYDTQ ILTAIAMGVH
Npun02008223    TALSRLGLPK LQLQPKEGLA MMNGTSVMTG IAANCVYDAK VLLALTMGVH
EncP            QALSEAGVEP MELSYKDGLA LINGTSGMVG LGTMVLQAAR RLVDRYLQVS
PputidaHAL      EALAVAGLEP LTLAAKEGLA LLNGTQASTA YALRGLFYAE DLYAAAIACG Avar03005300    ALDIQALNGT NQSFHPFIHN SKPHPGQLWA ADQMISLLAN SQLVRDELDG
Npun02008223    ALAIQGLYGT NQSFHPFIHQ CKPHPGQLWT ADQMFSLLKD SSLVREELDG
EncP            ALSVEGLAGM TKPFDPRVHG VKPHRGQRQV ASRLWEGLAD SHLAVNELDT
PputidaHAL      GLSVEAVLGS RSPFDARIHE ARGQRGQIDT AACFRDLLGD SSEVS.....
```

FIGURE 4 (CONTINUED)

```
Avar03005300    .........K  HDYRDHELIQ  DRYSLRCLPQ  YLGPIVDGIS  QIAKQIEIEI
Npun02008223    .........K  HEYRGKDLIQ  DRYSLRCLAQ  FIGPIVDGVS  EITKQIEVEM
EncP            EQTLAGEMGT  VAKAGSLAIE  DAYSIRCTPQ  ILGPVVDVLD  RIGATLQDEL
PputidaHAL      ..........  LSHKNCDKVQ  DPYSLRCQPQ  VMGACLTQLR  QAAEVLGIEA Avar03005300    NSVTDNPLID  VDNQASYHGG  NFLGQYVGMG  MDHLRYYIGL  LAKHLDVQIA
Npun02008223    NSVTDNPLID  VENQVSYHGG  NFLGQYVGVT  MDRLRYYIGL  LAKHIDVQIA
EncP            NSSNDNPIVL  PEEAEVFHNG  HFHGQYVAMA  MDHLNMALAT  VTNLANRRVD
PputidaHAL      NAVSDNPLVF  AAEGDVISGG  NFHAEPVAMA  ADNLALAIAE  IGSLSERRIS Avar03005300    LLASPEFSNG  LPPSLLGNRE  RKVNMGLKGL  QICGNSIMPL  LTFYGNSIAD
Npun02008223    LLVSPEFSNG  LPPSLVGNSD  RKVNMGLKGL  QISGNSIMPL  LSFYGNSLAD
EncP            RFLDKSNSNG  LPAFLCREDP  .GLRLGLMGG  QFMTASITAE  TRTLTIPMSV
PputidaHAL      LMMDKHMS.Q  LPPFLVENG.  .GVNSGFMIA  QVTAAALASE  NKALSHPHSV Avar03005300    RFPTHAEQFN  QNINSQGYTS  ATLARRSVDI  FQNYVAIALM  FGVQAVDLRT
Npun02008223    RFPTHAEQFN  QNINSQGYIS  ANLTRRSVDI  FQNYMAIALM  FGVQAVDLRT
EncP            QSLTSTADF.  QDIVSFGFVA  ARRAREVLTN  AAYVVAFELL  CACQAVDIRG
PputidaHAL      DSLPTSANQ.  EDHVSMAPAA  GKRLWEMAEN  TRGVPAIEWL  GACQGLDLRK Avar03005300    YKKTGHYDAR  ACLSPATERL  YSAVRHVVGQ  KPTSDRPYIW  NDNEQGLDEH
Npun02008223    YKMKGHYDAR  TCLSPNTVQL  YTAVCEVVGK  PLTSVRPYIW  NDNEQCLDEH
EncP            ADKL......  ...SSFTRPL  YERTRKIVP.  ..........F  FDRDETITDY
PputidaHAL      GLKT......  ...SAKLEKA  RQALRSEVA.  ..........H  YDRDRFFAPD Avar03005300    IARISADIAA  GGVIVQAVQD  ILPCLH..
Npun02008223    IARISADIAG  GGLIVQAVEH  IFSSLKST
EncP            VEKLAADLIA  GEPVDAAVAA  H.......
PputidaHAL      IEKAVELLAK  GSLTGLLPAG  VLPSL...
```

COMPOSITIONS OF PROKARYOTIC PHENYLALANINE AMMONIA-LYASE AND METHODS OF USING COMPOSITIONS THEREOF

REFERENCE TO A SEQUENCE LISTING

This application contains a Sequence Listing appendix, provided as a paper copy, as required under 37 CFR § 1.821 (c), and is herein incorporated by reference in its entirety, as required by 37 CFR § 1.52(e)(5). A copy of the sequence listing is also provided as required under 37 CFR §1.821(e), as a Computer Readable Form (CRF) on a diskette. The compact disc contains a single ASCII file for the Sequence Listing, named "0165CPUS06.5T25", which was created on Aug. 11, 2006, using an IBM-PC machine format, is 45 kb in size, and is Windows compatible.

TECHNICAL FIELD OF INVENTION

This invention relates to prokaryotic phenylalanine ammonia-lyase (PAL) and compositions thereof, and optimization of such compositions to enhance PAL catalytic activity and stability while reducing immunogenicity and/or proteolytic sensitivity of PAL. The invention further relates to the use of such optimal compositions of PAL for therapeutic and industrial purposes.

BACKGROUND OF THE INVENTION

PAL is a non-mammalian enzyme widely distributed in plants (Koukol, et al., J. Biol. Chem. 236:2692-2698 (1961); Hanson, et al., The Enzymes 7:75-166 (1972); Poppe, et al., (2003) ibid.), some fungi (Rao, et al., Can. J. Biochem. 4512: 1863-1872 (1967); Abell, et al., Methods Enzymol. 142:242-253 (1987)) and bacteria (Bezanson, et al., Can. J. Microbiol. 16:147-151. (1970); Xiang, et al, J. Biol. Chem. 277:32505-32509 (2002); Hill, et al., Chem. Coomun. 1358-1359 (2003)) and can be recombinantly produced in *Escherichia coli*.

A representative list of PALs includes: Q9ATN7 *Agastache rugosa*; O93967 *Amanita muscaria* (Fly agaric); P35510, P45724, P45725, Q9SS45, Q8RWP4 *Arabidopsis thaliana* (Mouse-ear cress); Q6ST23 *Bambusa oldhamii* (Giant timber bamboo); Q42609 *Bromheadia finlaysoniana* (Orchid); P45726 *Camellia sinensis* (Tea); Q9MAX1 *Catharanthus roseus* (Rosy periwinkle) (Madagascar periwinkle); Q9SMK9 *Cicer arietinum* (Chickpea); Q9XFX5, Q9XFX6 *Citrus clementina×Citrus reticulate*; Q42667 *Citrus limon* (Lemon); Q8H6V9, Q8H6W0 *Coffea canephora* (Robusta coffee); Q852S1 *Daucus carota* (Carrot); O23924) *Digitalis lanata* (Foxglove); O23865) *Daucus carota* (Carrot); P27991) *Glycine max* (Soybean); O04058) *Helianthus annuus* (Common sunflower); P14166, (Q42858) *Ipomoea batatas* (Sweet potato); Q8GZR8, Q8W2E4 *Lactuca sativa* (Garden lettuce); O49835, O49836 *Lithospermum erythrorhizon*; P35511, P26600 *Lycopersicon esculentum* (Tomato); P35512 *Malus domestica* (Apple) (*Malus sylvestris*); Q94C45, Q94F89 *Manihot esculenta* (Cassava) (Manioc); P27990 *Medicago sativa* (Alfalfa); P25872, P35513, P45733 *Nicotiana tabacum* (Common tobacco); Q6T1C9 *Quercus suber* (Cork oak); P14717, P53443, Q7M1Q5, Q84VE0, Q84VE0 *Oryza sativa* (Rice); P45727 *Persea americana* (Avocado); Q9AXI5 *Pharbitis nil* (Violet) (Japanese morning glory); P52777 *Pinus taeda* (Loblolly pine); Q01861, Q04593 *Pisum sativum* (Garden pea); P24481, P45728, P45729 *Petroselinum crispum* (Parsley) (*Petroselinum hortense*); Q84LI2 *Phalaenopsis×Doritaenopsis* hybrid cultivar; P07218, P19142, P19143 *Phaseolus vulgaris* (Kidney bean) (French bean); Q7XJC3, Q7XJC4 *Pinus pinaster* (Maritime pine); Q6UD65 *Populus balsamifera* subsp. *trichocarpa×Populus deltoides*; P45731, Q43052, O24266 *Populus kitakamiensis* (Aspen); Q8H6V5, Q8H6V6 *Populus tremuloides* (Quaking aspen); P45730 *Populus trichocarpa* (Western balsam poplar); O64963 *Prunus avium* (Cherry); Q94EN0 *Rehmannia glutinosa*; P11544 *Rhodosporidium toruloides* (Yeast) (*Rhodotorula gracilis*); P10248 *Rhodotorula rubra* (Yeast) (*Rhodotorula mucilaginosa*); Q9M568, Q9M567 *Rubus idaeus* (Raspberry); P31425, P31426 *Solanum tuberosum* (Potato); Q6SPE8 *Stellaria longipes* (Longstalk starwort); P45732 *Stylosanthes humilis* (Townsville stylo); P45734 *Trifolium subterraneum* (Subterranean clover); Q43210, Q43664 *Triticum aestivum* (Wheat); Q96V77 *Ustilago maydis* (Smut fungus); P45735 *Vitis vinifera* (Grape); and Q8VXG7 *Zea mays* (Maize).

Numerous studies have focused on the use of the enzyme phenylalanine ammonia-lyase (PAL, EC 4.3.1.5) for enzyme substitution treatment of phenylketonuria (PKU) (Hoskins, et al., (1980) ibid.; Gilbert, et al., Biochem. J., 199(3):715-723 (1981); Hoskins, J. A., et al., (1982) ibid.; Sarkissian, et al., (1999) ibid.; Liu, et al., Artif. Cells Blood Substit. Immobil. Biotechnol., 30(4):243-257 (2002); Wieder, K. J., J Biol Chem., 254(24):12579-12587 (1979); Gamez, Development of Pegylated forms of Recombinant *Rhodosporidium toruloides* Phenylalanine Ammonia Lyase for the Treatment of Classical PKU. Mol. Ther. In press; Ambrus, et al., J. Pharmacol. Exp. Ther., 224(3):598-602 (1983); Ambrus, et al., Science, 201(4358):837-839 (1978); Kalghatgi, Res. Commun. Chem. Pathol. Pharmacol., 27(3):551-561 (1980); Ambrus, Res. Commun. Chem. Pathol. Pharmacol., 37(1): 105-111 (1982); Gilbert, et al., Biochem. Biophys. Res. Commun., 131(2):557-563 (1985); Pedersen, Res. Commun. Chem. Pathol. Pharmacol., 20(3):559-569 (1978); Marconi, et al., Biochimie, 62(8-9):575-580 (1980); Larue, et al., Dev. Pharmacol. Ther., 9(2):73-81 (1986); Ambrus, C. M., et al., (1987) ibid.; Bourget, et al., Appl. Biochem. Biotechnol., 10:57-59 (1984); Bourget, et al., FEBS Lett., 180(1):5-8 (1985); Bourget, et al., Biochim. Biophys. Acta, 883(3):432-438 (1986); Chang, et al., Artif. Cells Blood Substit. Immobil. Biotechnol., 23(1):1-21 (1995); Chang, et al., Mol. Biotechnol., 17(3):249-260 (2001); U.S. Pat. No. 5,753,487).

PKU is an inborn error of amino acid metabolism that results from impaired activity of hepatic phenylalanine hydroxylase (PAH), the enzyme responsible for the metabolism of phenylalanine. Patients with PAH mutations that lead to PKU and hyperphenylalaninemia (HPA) display elevated levels of phenylalanine, impaired neurophysiological functioning and reduced cognitive development. For patients with severe PKU, there is the potential for irreversible mental retardation unless phenylalanine levels are maintained at low levels using dietary restrictions. PAL converts phenylalanine to ammonia and trans-cinnamic acid, a harmless metabolite, which is further metabolized and excreted in the urine as hippurate (Hoskins, Lancet 8165:392-394 (1980); Hoskins, et al., Biomed Mass Spectrom 11(6): 296-300 (1984)).

Current treatment for PKU involves the lifetime adherence to a diet that is low in the amino acid phenylalanine (Levy, Proc. Natl. Acad. Sci. U.S.A. 96(5):1811-1813 (1999)). This dietary therapy is difficult to maintain (Matalon, et al., Genet. Med., 6(1): 27-32 (2004); Woolf, et al., Arch. Dis. Child. 33(167):31-45 (1958); Kim, Mol. Ther. 10(2):220-224 (2004)) and does not always eliminate the damaging neurological effects that can be caused by elevated phenylalanine levels (Sarkissian, et al., Mol. Genet. Metab. 69:188-194

(2000)). Less than ideal dietary control during pregnancy can lead to birth defects (Levy, (1999) ibid.). In addition, it is very difficult for PKU/HPA patients to live a normal life while following the restrictive diet, and dietary therapy can be associated with deficiencies of several nutrients, some of which are detrimental for brain development (Levy, (1999) ibid.). Most low phenylalanine diet products have organoleptic properties sufficiently unsatisfactory that compliance with this treatment is compromised (Levy, (1999) ibid.). Therefore, development of a therapeutic treatment would replace or supplement the current dietary treatment and prevent the neurological damages inflicted on those individuals with PKU, particularly for those patients with the most severe forms of the disease.

In 1999, Scriver and colleagues reported their initial studies on the use of the enzyme PAL from *Rhodosporidium toruloides* (Sarkissian, et al., 1999 ibid.) for PKU enzyme substitution applications. Mouse PKU and HPA model studies demonstrated that PAL administration (either by i.p. injection or orally using either PAL in combination with aprotinin protease inhibitor or PAL recombinantly expressed and present inside *E. coli* cells) was associated with lower blood plasma phenylalanine levels. In addition, preliminary studies describing the use of PAL with PKU patients have shown reduction in phenylalanine levels using PAL administered in enteric-coated gelatin capsules (Hoskins, et al., (1980) ibid.) or using an extracorporeal enzyme factory (Ambrus, et al., Ann. Intern. Med., 106(4):531-537 (1987)). These studies suggest that if PAL is protected against proteolytic degradation, significant reductions of plasma Phe can be achieved upon oral administration.

The use of PAL for cancer treatment has also been suggested based on its ability to limit the nutrient supply of phenylalanine to cancer cells and thereby inhibit neoplastic growth (Fritz, et al., J Biol Chem. 251(15):726 (1976); Roberts, et al., Cancer Treat Rep., 60(3):261-263 (1976); Shen, et al., Cancer Res. 37(4):1051-1056 (1977); Shen, et al., Cancer Treat Rep. 63(6):1063-1068 (1979); Wieder, et al, J Biol Chem., 254(24):12579-12587 (1979)). However, intravenously injected pegylated PAL was cleared rapidly from circulating blood after the 13th injection. In addition, PAL-mediated reduction in phenylalanine prevented the proliferation of murine leukemia and metastatic melanoma (Abell, et al., Cancer Res. 33:2529-2532 (1973)), Roberts, et al., ((1976) ibid) Shen, et al., ((1977) ibid)).

Bacterial PAL from the marine bacterium *Streptomyces maritimus* may serve as an important source of the bacteriostatic agent enterocin. *S. maritimus* PAL, EncP, catalyzes the initial step in enterocin synthesis, which is the conversion of phenylalanine to trans-cinnamic acid (Xiang, et al., J. Biol. Chem. 277:32505-32509 (2002)).

PAL may be used for the industrial synthesis of L-phenylalanine methyl ester (for Aspartame production) (D'Cunha, et al., Enzyme and Microbial Technology 19(6):421-427 (1996); Hamilton, et al., Trends in Biotechnol. 3(3):64-68 (1985)) and other substituted L-phenylalanine derivatives that are used as pharmaceutical precursors (U.S. Patent App. 20020102712).

PAL may also have agricultural applications, wherein PAL participates in the initial enzymatic process leading to the phenylpropanoids that produce lignins, coumarins, and flavanoids in plants, fungi, and bacteria. Hence, modulation of PAL activity can influence a number of agricultural phenomena such as the browning of fruit. In addition, structure-based drug design of active site PAL inhibitors could lead to effective herbicides (Poppe, et al., ibid.).

Although PAL potentially has various industrial and therapeutic applications, the use of PAL may be limited by reduced specific activity and proteolytic instability. Similar to other therapeutic proteins, use of PAL as an enzyme therapy is accompanied by several disadvantages such as immunogenicity and proteolytic sensitivity. Further, a delicate balance is required between substrate affinity and enzyme activity to achieve and maintain control of plasma phenylalanine levels within a normal somewhat narrow range in disorders characterized by hyperphenylalanemia. As yet, a concerted effort toward improving these parameters has not been made due to a paucity of structural and biochemical knowledge regarding this protein.

Thus, there remains a need for PAL molecules with optimal kinetic characteristics including potent catalytic activity and greater biological half-life, greater biochemical stability and attenuated immunogenicity.

SUMMARY OF THE INVENTION

Several bacterial PAL have been already identified as part of the HAL/PAL family, including but not limited to PAL from *Streptomyces maritimus* (also known as EncP, SEQ ID NO:7, FIG. 4), PAL/HAL from *Nostoc punctiforme* (Accession ZP_00105927 from *Nostoc punctiforme* ATCC 29133, submitted Oct. 1, 2004, NCBI Microbial Genomes Annotation Project) (SEQ ID NO:5, FIG. 4), PAL/HAL from *Anabaena variabilis* (Gene ID 3679622, Ava_3988 phenylalanine/histidine ammonia lyase[*Anabaena variabilis* ATCC 29413, Mar. 31, 2006 (SEQ ID NO:6, FIG. 4), the photosynthetic prokaryote *Anacystis nidulans* (Lofflehardt, Z. Naturforsch 31(11-12); 693-9 (1976)), the gram-negative bacteria from the family Enterobacteriaceae, *Photorabdus luminescens* TT01 (Williams, et al. Microbiology 151:2543-2550 (2005), and *Streptomyces verticillatus* (Bezanson, et al. Can. J. Microbiol. 16(3):147-51 (1970)). Further, PAL activity has been evaluated in *Streptomyces maritimus* (Xiang, L., et al., J. Biol. Chem. 277:32505-32509 (2002)). Cyanobacteria, such as *Anabaena* and *Nostoc* have been studied with respect to their production of bioactive natural products which are generated via mixed polyketide-peptide biosynthetic pathways (Moore, B. S., Natural Products Reports 22(5):580-593 (2005); Becker, et al., Gene 325:3542 (2004); Hoffman, et al., Gene 311:171-180 (2003)). The invention is based on the finding that prokaryotic or bacterial PAL may serve as an effective treatment for PKU and other disorders. The invention contemplates compositions of bacterial PAL and biologically active fragments, mutants, variants and analogs thereof, with enhanced properties, such as more potent catalytic activity, greater biochemical stability and, for therapeutic applications, attenuated immunogenicity and greater biological half-life. The present invention also provides methods of production and purficiation of bacterial PAL and biologically active fragments, mutants, variants and analogs thereof, and methods of using such compositions for therapeutic and industrial purposes.

As used herein, "bacterial PAL" and "prokaryotic PAL" are used interchangeably to mean (1) wild type PAL from prokaryotic organisms, including but not limited to PAL from *Streptomyces maritimus* (also known as EncP, SEQ ID NO:7, FIG. 4), *Nostoc punctiforme* (SEQ ID NO:5, FIG. 4), *Anabaena variabilis* (SEQ ID NO:6, FIG. 4), *Anacystis nidulans* (Lofflehardt, et al., (1976)), *Photorabdus luminescens* TT01 (Williams, et al., (2005), and *Streptomyces verticillatus* (Bezanson, et al., (1970)); (2) fragments, mutants, variants and analogues of such wild type enzymes that retain similar (i.e. at least 50%) catalytic activity for phenylalanine, and that preferably exhibit increased catalytic activity and/or increased half-life and/or decreased immunogenicity, and (3) chemically modified versions of such wild type enzymes, fragments, mutants, variants and analogs thereof that have been are linked to other chemical moieties that provide other advantageous effects, such as enhanced half-life. For example, any references to methods of making or using prokaryotic PAL, fragments, mutants, variants, analogs or chemically modified versions thereof, and compositions of such enzyme(s), for either therapeutic or industrial purposes, are meant to refer to methods of making, using or formulating all such wild type, fragments, mutants, variants, analogs or chemical modifications thereof.

In the first aspect, the present invention provides bacterial PAL and biologically active fragments, mutants, variants or analogs thereof. A preferred embodiment is a bacterial PAL from *Nostoc punctiforme* (SEQ ID NO:5) or biologically active fragment, mutant, variant or analog thereof. Another preferred embodiment is a bacterial PAL from *Anabaena variabilis* (SEQ ID NO:6) or biologically active fragment, mutant, variant or analog thereof. Preferably the variants retain the wild type active site residues at positions corresponding to Ser 210 Ala-Ser-Gly triad (211-213) Asp214, Leu215, Asn270, Val269, Leu266, Leu134, His137, Lys468, Glu496, Gln 500 in PAL from *Rhodosporidium toruloides* or conservative substitution(s) of these active site residue(s), of which the Ala-Ser-Gly triad at 211-213 is believed to be the binding site for phenylalanine.

Desirable variants may include fusion proteins in which the enzyme has been fused to another heterologous polypeptide, such as a native or modified constant region of an immunoglobulin or a fragment thereof that retains the salvage epitope, known in the art to increase half-life.

The invention further contemplates chemically modified versions of such polypeptides, which have been linked to a chemical moiety that provides other advantageous effects. For example, nonspecific or site-specific (e.g. N-terminal) linkage of water-soluble polymers to polypeptides is known in the art to improve half-life, and linkage of chemical moieties may also reduce immunogenicity and improve protease resistance.

Such bacterial PAL is isolated and purified in accordance with the methods of the present invention and is thereby present in amounts which enable using the enzyme therapeutically. In some embodiments, a cDNA encoding for a complete or wild-type bacterial PAL is used. However, in other embodiments, a cDNA encoding for a biologically active fragment or mutant thereof may be used. Further, the present invention provides compositions of optimized bacterial PAL obtained by structure-based molecular engineering approaches and/or chemically-modified (e.g. pegylated) forms of PAL. Specific embodiments contemplate optimal compositions of PAL with improved specific activity, enhanced stability, reduced immunogenicity and/or proteolytic sensitivity appropriate for therapeutic use. A preferred embodiment is a pegylated form of *Nostoc punctiforme* PAL with improved specific activity. Another preferred embodiment is a pegylated for of *Anabaena variabilis* PAL with improved specific activity.

In some embodiments, the biologically active sites of wild-type PAL according to the invention may be modified as desired to optimize PAL kinetic characteristics. In a preferred embodiment, a modified PAL has sufficient activity to reduce but also maintain plasma phenylalanine levels within the optimal range of about 120 uM to about 240 uM. In most preferred embodiments, the biologically active modified mutant PAL has a kcat of at least about 4.0 s−1 and preferably greater than 20 s−1. In other preferred embodiments, the biologically active modified PAL has a Km of between about 100 μM to about 1000 μM. In most preferred embodiments, the biologically active modified PAL exhibits enzymatic activity that is from about two-fold to about 1000-fold times greater that that of the wild-type. Such biological active mutants may be formed using methods well known in the art, such as by site-directed mutagenesis. In further embodiments, the invention contemplates use of bacterial PAL that metabolizes phenylalanine (i.e. converts phenylalanine to another substance) in preparation of a medicament for the treatment of a deficiency in PAH activity, in mammals, preferably humans, as well as a pharmaceutical composition containing bacterial PAL for use in treating a deficiency in PAH activity. In the preferred embodiment, the pharmaceutical composition comprises highly purified PAL derived from bacteria, or a biologically active fragment, mutant or analog thereof alone or in combination with a pharmaceutically suitable carrier. Preferred preparations contain bacterial PAL with a purity greater than 95%, 96%, 97%, 98%, 99%, 99.2%, 99.5%, 99.6%, 99.7%, 99.8%, or 99.9%. The relative specific activity of the bacterial PAL according to the present invention is preferably greater than about 110% of the specific activity of wild-type PAL.

In the second aspect, the present invention features novel methods of using PAL compositions for therapeutic and industrial purposes. In one embodiment, the invention contemplates methods of treating disorders caused all or in part by a deficiency in PAH activity by administering a therapeutically effective amount of a pharmaceutical composition comprising bacterial PAL to a subject in need of such treatment. The deficiency in PAH activity can be observed, e.g., as activity levels of 50% or less, 25% or less, or 10% or less or 1% or less, compared to normal levels of PAH activity and can manifest as elevated phenylalanine levels, for example, as in hyperphenylalanemia, mild phenylketonuria or classic severe phenylketonuria. In preferred embodiments, the disease is phenylketonuria (PKU).

In specific embodiments, the subject is one who has been diagnosed as having a mutant phenylalanine hydroxylase (PAH). The mutant PAH may comprise a mutation in the catalytic domain of PAH. Exemplary such mutations include but are not limited to mutations F39L, L48S, I65T, R68S, A104D, S110C, D129G, E178G, V190A, P211T, R241C, R261Q, A300S, L308F, A313T, K320N, A373T, V388M E390G, A395P, P407S, and Y414C.

Also contemplated is a method of treating a subject having above normal concentration of plasma phenylalanine (e.g., greater than 180 μM and more preferably, greater than 360 μM) comprising administering to the subject a bacterial PAL composition in an amount effective to produce a decrease in the plasma phenylalanine concentration of the subject. The subject will likely have a plasma phenylalanine concentration greater than 180 μM prior to administration of the bacterial PAL. More particularly, the subject has a plasma phenylalanine concentration of between 120 μM and 200 μM. In other embodiments, the subject has a plasma phenylalanine concentration of between 200 μM and 600 μM. In still other embodiments, the subject has a plasma phenylalanine concentration of between 600 μM and 1200 μM. Yet another class of subjects to be treated is those that have an unrestricted plasma phenylalanine concentration greater than 1200 μM.

In specific embodiments, the subject is an infant, more particularly, an infant having a plasma phenylalanine concentration greater than 1200 μM. The invention contemplates methods of treating an infant having phenylketonuria, comprising administering a bacterial PAL composition to the subject in an amount effective to produce a decrease in the plasma phenylalanine concentration of the infant wherein the infant is between 0 and 3 years of age and the infant has a plasma phenylalanine concentration of between about 360 µM to about 4800 µM. Prior to the administering of bacterial PAL, the infant has a phenylalanine concentration of about 1200 µM and the administering of bacterial PAL decreases the plasma phenylalanine concentration to about 1000 µM. In other embodiments, prior to the administering of bacterial PAL the infant has a phenylalanine concentration of about 800 µM and the administering of PAL decreases the plasma phenylalanine concentration to about 600 µM. In still further embodiments, prior to the administering of PAL the infant has a phenylalanine concentration of about 400 µM and the administering of PAL decreases the plasma phenylalanine concentration to about 300 µM. The therapeutic methods contemplated herein should preferably reduce the plasma phenylalanine concentration of the infant to a range of between about 120 µM to about 360 µM and most preferably to a range of between about 120 µM to about 240 µM.

Also contemplated herein is a method for the treating a pregnant female having hyperphenylalaninemia (HPA) comprising administering to the subject bacterial PAL alone or in combination with a protein-restricted diet, wherein administration of bacterial PAL alone or in combination with the protein-restricted diet is effective to lower the phenylalanine concentration in the plasma of the subject as compared to the concentration in the absence of the combined administration. In certain embodiments, the subject has an unrestricted plasma phenylalanine concentration of greater than 180 µM but less than 600 µM. In other embodiments, the subject has an unrestricted plasma phenylalanine concentration of greater than 500 µM but less than 1200 µM. In still other embodiments, the subject has an unrestricted plasma phenylalanine concentration of greater than 1200 µM. Pregnant subjects with a plasma phenylalanine concentration greater than 1200 µM are particularly attractive candidates for this type of therapy, as are subject who are females of childbearing age that are contemplating pregnancy. In those embodiments, in which the subject has a plasma phenylalanine concentration greater than 1200 µM, and the method further comprises administering a protein-restricted diet to the subject.

The invention describes methods of treating classic severe phenylketonuria (PKU) in a subject comprising administering to the subject a bacterial PAL or a biologically active fragment, mutant, variant or analog thereof wherein the administration of bacterial PAL is effective to lower the phenylalanine concentration in the plasma of the subject as compared to the concentration in the absence of bacterial PAL administration. A subject selected for treatment according to the methods of the invention will have an elevated plasma Phe concentration, such a concentration may be greater than 1800 µM in the absence of the therapeutic. Other embodiments contemplate a subject that has a plasma phenylalanine concentration of greater than 1000 µM in the absence of a therapeutic regimen. In preferred embodiments, the combined administration methods of the invention decrease the plasma phenylalanine concentration of the subject to less than 600 µM. More preferably, it is decreased to less than 500 µM. Even more preferably, the combined administration decreases the plasma phenylalanine concentration of the subject in the range from about 120 µM to about 360 µM. Most preferably, the plasma phenylalanine concentration of the subject is reduced in the range from about 120 µM to about 240 µM.

Preferred embodiments include optimizing the dosage to the needs of the organism to be treated, preferably mammals or humans, to effectively ameliorate the disease symptoms. PAL may be administered in a single daily dose, multiple doses on a daily basis, in a single weekly dose or multiple doses on a weekly basis. In some embodiments, the PAL therapy is not continuous, but rather PAL is administered on a daily basis until the plasma phenylalanine concentration of the subject is decreased to less than 360 µM. Preferably, wherein the plasma phenylalanine concentration of the subject is monitored on a daily basis and the PAL is administered when a 10% increase in plasma phenylalanine concentration is observed. In yet other preferred embodiments, doses are delivered once weekly. The invention contemplates doses of at least 0.001 mg/kg, 0.005 mg/kg, 0.01 mg/kg, 0.05 mg/kg, and may range up to 0.1 mg/kg, 0.5 mg/kg, 1.0 mg/kg or higher per week. The preferred dose is 0.001 mg/kg/week.

A variety of parenteral or nonparenteral routes of administration, including oral, transdermal, transmucosal, intrapulmonary (including aerosolized), intramuscular, subcutaneous, or intravenous that deliver equivalent dosages are contemplated. Administration by bolus injection or infusion directly into the joints or CSF is also specifically contemplated, such as intrathecal, intracerebral, intraventricular, via lumbar puncture, or via the cisterna magna. Preferably the doses are delivered subcutaneously or orally.

Other means of increasing PAL activity in the human subjects are also contemplated, including gene therapy. Transfer of a PAL gene is possible through a variety of means known in the art, including viral vectors, homologous recombination, or direct DNA injection. Within the scope of this aspect are embodiments featuring nucleic acid sequences encoding all or a part of bacterial PAL or a biologically active mutant or analogs thereof, which may be administered in vivo into cells affected with PAH deficiency.

In another embodiment, bacterial PAL may also be administered in combination with a protein restricted diet. The protein-restricted diet administered in the methods herein is one that is a phenylalanine-restricted diet wherein the total phenylalanine intake of the subject is restricted to less than 600 mg per day. In other embodiments, the protein-restricted diet is a phenylalanine-restricted diet wherein the total phenylalanine is restricted to less than 300 mg per day. In still other embodiments, the protein-restricted diet is one, which is supplemented with amino acids, such as tyrosine, valine, isoleucine and leucine. Also contemplated is a composition comprising bacterial PAL and a pharmaceutically acceptable carrier, diluent or excipient. The composition may further comprise a medical protein supplement. In other embodiments, the PAL composition is part of an infant formula. In still other embodiments, the protein supplement is phenylalanine free. The protein supplement preferably is fortified with L-tyrosine, L-glutamine, L-carnitine at a concentration of 20 mg/100 g supplement, L-taurine at a concentration of 40 mg/100 g supplement and selenium. It may further comprise the recommended daily doses of minerals, e.g., calcium, phosphorus and magnesium. The supplement further may comprise the recommended daily dose of one or more amino acids selected from the group consisting of L-leucine, L-proline, L-lysine acetate, L-valine, L-isoleucine, L-arginine, L-alanine, glycine, L-asparagine monohydrate, L-tryptophan, L-serine, L-threonine, L-histidine, L-methionine, L-glutamic acid, and L-aspartic acid. In addition, the supplement may be fortified with the recommended daily dosage of vitamins A, D and E. The supplement preferably comprises a fat content that provides at least 40% of the energy of the supplement. Such a supplement may be provided in the form of a powder supplement or in the form of a protein bar.

The invention contemplates methods of treating various forms of neoplastic growth and cancer, including but not limited to lymphoblastic leukemia, mammary tumors, and melanomas.

The invention contemplates methods of using bacterial PAL for the commercial production of phenylalanine from ammonia and t-cinnamate. Phenylalanine is used in aspartame, a sweetener and other food products, including beverages, cereals, cakes, desserts, egg and cheese dishes, fats, oils, fish and other seafoods, meat and meat products, milk and milk products, nuts, sauces and condiments, soups, sugars, jams and spreads, and vegetables.

It is further contemplated that bacterial PAL may be used for the production of herbicides and antimicrobial agents including enterocin and erythromycin.

In a third aspect, the present invention features a method to produce prokaryotic PAL or a biologically active fragment, mutant, variant or analog thereof in amounts which enable using the enzyme therapeutically. The present invention contemplates PAL produced by bacteria including but not limited to *Streptomyces, Sorangium, Pseudomonas*, and cyanobacteria such as *Nostoc* and *Anabaena*. In some embodiments, PAL is produced by the bacterial species *Streptomyces maritimus, S. verticillatus, Soragium cellulosum, Nostoc punctiforme, Nostoc tobacum, Anabaena variabilis*, and *Pseudomonas putida*. In another embodiment prokaryotic PAL enzyme activity is generated using cDNA or DNA sequences that are derived from sequences sometimes described as coding for HAL activity or featuring a PAL-HAL motif, but possessing key PAL residues which differ them from HAL.

In a broad embodiment, the method comprises the step of transforming a cDNA or DNA encoding for all or a part of a prokaryotic PAL or a biologically active fragment, mutant, variant or analog thereof into a cell suitable for the expression thereof. In preferred embodiments, an expression vector is used to transfer the DNA into a suitable cell or cell line for expression thereof. In one particularly preferred embodiment, the cDNA is transformed into *E. coli* and recombinant bacterial PAL is overexpressed as fusion protein. In a further embodiment, the method of producing prokaryotic PAL comprises the steps of: (a) growing cells transformed with a cDNA encoding all or a biologically active variant, fragment or mutant of prokaryotic PAL in a suitable growth medium to an appropriate density to produce a seed culture, (b) introducing the transformed cells into a bioreactor, (c) supplying a suitable growth medium to the bioreactor, and (d) separating the transfected cells from the media containing the enzyme.

In a preferred embodiment, recombinant PAL is over-expressed as an N-terminal octahistidyl-tagged fusion protein in a vector preferably *E coli* BL21(DE3)/pLyseS (Invitrogen) with an inducible promoter such as with IPTG (isopropyl-beta-D-thiogalactopyranoside). In a particularly preferred embodiment, the method of producing prokaryotic PAL comprises the steps of: (1) growing a seed culture for a bioreactor/fermenter from a glycerol stock in shake flasks, (2) introducing such seed culture into a controlled bioreactor in fed-batch mode; (3) growing said culture in glucose-supplemented media, pH (7.8), >20% dissolved oxygen, agitation up to 1200 rpm, 300 C until reaching a cell density of OD600 of 70-100 (~22-25 hrs); (4) inducing said culture with 0.4 mM IPTG; (5) growing said culture at a reduced temperature of 22 to 260 C until activity change is <0.1 IU/ml (approximately 40-48 hrs and an OD600 typically of 200); and (5) harvesting bacteria by continuous centrifugation. In a preferred embodiment, the cell culture media is typically defined and composed of yeast extract protein, peptone-tryptone, glucose, glycerol, casamino acids, trace salts and phosphate buffering salts.

In a fourth aspect, the present invention features a method to purify bacterial PAL or a biologically active fragment, mutant or analog thereof. According to a first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another preferred embodiment, the method to purify the bacterial PAL comprises the steps of: (a) Lysis of the bacteria containing recombinant PAL; (b) treatment of lysate with heat to inactivate viruses; (c) clarification of this lysate using a second continuous centrifigation step and/or depth filtration (d) passage of clarified lysate through a charcoal filtration step; (e) passage of filtrate in (d) through a final filtration step (as with a Sartorious Sartopore 0.2 μM filter); (f) passage of final filtrate over a hydrophobic interaction chromatography resin, such as a butyl hydrophobic interaction chromatography; (g) passage of eluate in (f) over an anionic chromatography resin, such as a Q ion exchange column; (h) recovery of final product by buffer exchange with tangential flow filtration; and (i) sterilization of the final product. Those skilled in the art readily appreciate that one or more of the chromatography steps may be omitted or substituted, or that the order of the chromatography steps may be changed within the scope of the present invention. Finally, appropriate sterilizing steps may be performed as desired.

In a fifth aspect, the present invention contemplates screening assays for identifying bacterial PAL that can prevent, ameliorate, or treat enhanced levels of phenylalanine by contacting a cell containing elevated levels of phenylalanine with the bacterial PAL and determining whether the bacterial PAL reduces such elevated levels of phenylalanine. Such screening assays may also include the steps of creating variants that include conservative or non-conservative substitutions in the active sites, e.g. Gly 142, Thr-Ser-Gly triad (143-145), Asp 146, Leu 147, Asn 196, Ile 195, Leu 192, Leu 76, Asn 79, Met 400, Thr 428, Gln 432 in EncP from *Streptomyces maritimus* which are equivalent to residues Ser 210 Ala-Ser-Gly triad (211-213) Asp214, Leu 215, Asn270, Val269, Leu266, Leu 134, His 137, Lys468, Glu496, Gln 500 in PAL from *Rhodosporidium toruloides*, in regions adjacent to the active sites, or throughout the polypeptide sequence, followed by testing the variants for in vitro phenylalanine converting activity. In certain embodiments, the method is a high throughput assay. In a preferred embodiment, complete genomes of the bacterial species are sequenced and screened for the presence of PAL homologs using a bioinformatics approach. In yet another preferred embodiment, PAL catalytic activity of the protein product of such homologs is confirmed, such as by testing ability to convert phenylalanine to trans-cinnamate in vitro.

In a sixth aspect, the invention provides methods of using bacterial PAL compositions for the diagnosis of diseases, including but not limited to disorders caused all or in part by a deficiency in PAH activity. In one embodiment, bacterial PAL is used to measure levels of phenylalanine in blood samples. In a further embodiment, the invention contemplates a diagnostic kit comprising bacterial PAL for use in monitoring blood samples of subjects with elevated levels of phenylalanine.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

FIG. 1. FIG. 1A: Gene sequence of *Nostoc punctiforme* (SEQ ID NO:1); FIG. 1B: Protein sequence of *Nostoc punctiforme* (SEQ ID NO:2).

FIG. 2. FIG. 2A: Gene sequence of *Anabaena variabilis* (SEQ ID NO:3); FIG. 2B: Protein sequence (SEQ ID NO:4).

FIG. 4. Alignment of cyanobacterial protein sequences of *N. punctiforme* PAL (SEQ ID NO:2) and *A. variabilis* PAL (SEQ ID NO:4) with EncP PAL (SEQ ID. No. 5) and *P. putida* HAL (SEQ ID NO:6). Active site residues, which correspond to PAL or HAL activity, are highlighted and underlined.

DETAILED DESCRIPTION OF THE INVENTION

Although PAL is a ubiquitous higher plant enzyme that catalyzes the nonoxidative deamination of phenylalanine to cinnamic acid in the committed step to phenylpropanoid metabolites (Hahlbrock, et al., Annu. Rev. Plant Phys. Plant Mol. Biol. 40:347-369 (1989)), PAL has only been encountered in a few bacteria where it is involved in benzoyl-CoA biosynthesis in "*S. maritimus*" (Xiang, et al., J. Biol. Chem. 277:32505-32509 (2002)) and Sorangium cellulosum (Hill, et al. Chem. Coomun.: 1358-1359 (2003)) and in the biosynthesis of cinnamamide in *Streptomyces verticillatus* (Bezanson, et al. Can. J. Microbiol. 16:147-151 (1970)). The bacteriostatic agent enterocin is a natural product of the marine bacterium "*Streptomyces maritimus*" whose biosynthesis involves a number of unusual features (Hertweck, et al., Chem. Biol. 11:461-468 (2004); Piel, et al. Chem. Biol. 7:943-955 (2000), Piel, et al., J. Am. Chem. Soc. 122:5415-5416 (2000); Xiang, et al, Proc. Natl. Acad. Sci. USA 101: 15609-15614 (2004)). Among these is the formation of the rare polyketide synthase (PKS) starter unit benzoyl-coenzyme A (CoA) (Moore, et al., Nat. Prod. Rep. 19:70-99 (2002)). The initial biochemical reaction involves the conversion of the amino acid L-phenylalanine to trans-cinnamic acid by the novel bacterial phenylalanine ammonia-lyase (PAL, EC 4.3.1.5) EncP (Xiang, et al., J. Biol. Chem. 277: 32505-32509 (2002)). Activation of cinnamic acid to its CoA thioester followed by a single round of beta-oxidation yields benzoyl-CoA (Hertweck, et al., ChemBioChem 2:784-786. (2001); Hertweck, et al., Tetrahedron 56:9115-9120 (2000); Xiang, et. al., J. Bacteriol. 185:399-404 (2003)), which primes the enterocin type II PKS for chain extension with seven molecules of malonyl-CoA.

Figure 3:
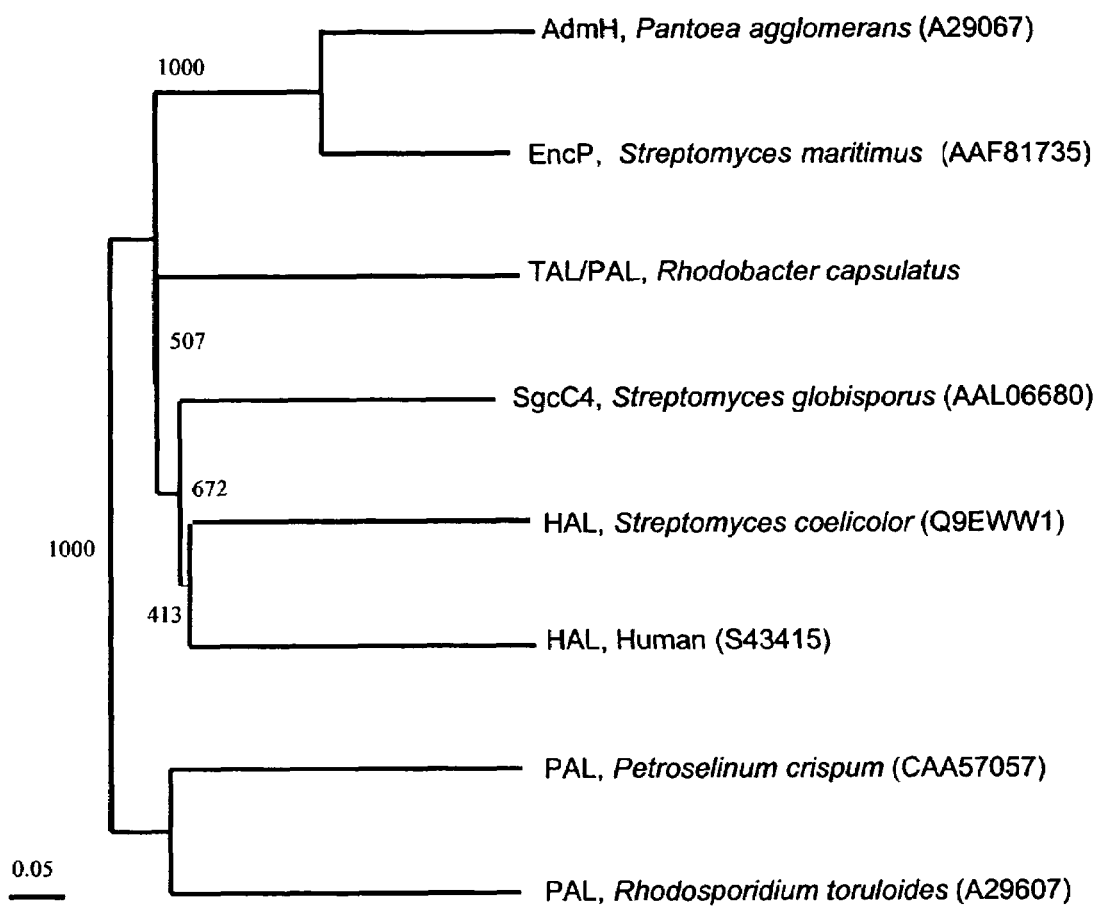
FIG. 3. Relatedness tree of aromatic amino acid ammonia-lyases from prokaryotes and eukaryotes. Sequences were retrieved from GenBank (accession numbers are given in parentheses) and aligned with ClustalX (1.83) using the Neighbour Joining Method.

The first prokaryotic PAL-encoding gene (encP) (SEQ ID:7) was characterized and its inactivation resulted in the abolishment of de novo cinnamic acid and enterocin synthesis in "*S. maritimus*" (Kalaitzis, J. Am. Chem. Soc. 125:9290-9291 (2003); Xiang, et al., J. Biol. Chem. 277:32505-32509 (2002)). Enterocin biosynthesis could be restored in encP-inactivated mutants through supplementation with cinnamic or benzoic acids as well as complementation with plasmid-bome encP. Furthermore, the heterologous expression of the encP gene under the control of the ermE* promoter in *Streptomyces coelicolor* led to the production of cinnamic acid in the fermented cultures (Xiang, et al., J. Biol. Chem. 277: 32505-32509 (2002)). The encP gene encodes a 522 amino acid protein that is considerably smaller than eukaryotic PALs by nearly 200 amino acid residues. Although sequence homologous to plant PALs such as from *Petroselinum crispum* (Röther, et al., Eur. J. Biochem. 269:3065-3075 (2002)) (CAA57056, 30% identical and 48% similar), it rather shares greater homology to bacterial histidine ammonia-lyases (HALs, EC 4.3.1.3) such as from *Pseudomonas putida* (Schwede, et al., Biochemistry 27:5355-5361 (1999)) (A35251, 36% identical and 54% similar, SEQ ID NO:8, FIG. 4) and to tyrosine ammonia-lyase (TAL) from *Rhodobacter capsulatus* (Kyndt, et al., FEBS Lett. 512:240-244 (2002)) (FIG. 3). The homology includes the conserved active site serine residue at position 143 of the phenylalanine/histidine/tyrosine family of ammonia-lyases that is the probable precursor of the modified dehydroalanine residue in the 4-methylideneimidazole-5-one (MIO) prosthetic group (Langer, et al., Advances in Protein Chemistry, vol. 58 (2001); . Poppe, Curr. Opin. Chem. Biol. 5:512-524 (2001); Schwede, et al., Biochemistry 27:5355-5361 (1999)). EncP shares greatest sequence homology to AdmH (AAO39102, 63% identical and 76% similar), a putative phenylalanine aminomutase involved in andrimid biosynthesis in *Pantoea agglomerans* that is related to the tyrosine aminomutase Sgc4 from *Streptomyces globisporus* (Christenson, et al., J. Am. Chem. Soc. 125:6062-6063 (2003); Christenson, et al., Biochemistry 42:12708-12718 (2003)). Notably, because encP has closer homology to a human protein (HAL) encP may be potentially less immunogenic. Also because they are very similar it could be possible to mutate encP to look like human HAL, a humanized version of encP.

HAL and PAL were shown to share in common a mechanism for the chemically difficult elimination of ammonia from histidine and phenylalanine, respectively. With both enzymes, a superelectrophilic prosthetic group 5 methylene-3,5-dihydroimidazol-4-one (MIO) to activate the non-acidic beta hydrogen atoms of their respective substrates by a Friedel-Crafts-type attack at the aromatic ring. The sigma complex that is generated prevents the extraction of protons from the ring by excluding any bases from access to the binding pocket of the enzyme. The formation of an exocyclic double bond is key in the elimination of ammonia, rearomatization, and fragmentation. The prosthetic MIO group is regenerated and the product urocanate or cinnamate is formed (Poppe, Lazlo and Retey, Janos, Friedel-Crafts-Type mechanism for the enzymatic elimination of ammonia from histidine and phenylalanine, Angew. Chem. Int. Ed. 44:3668-3688 (2005)).

Because of the high homology between HAL and PAL, the conserved regions of HAL and PAL are referred to HAL/PAL conserved region. This high homology can create some ambiguities in databases like NCBI on the potential enzyme activity of a "PAL-HAL" protein conducting to mislabeling, such as with protein sequences listed in the NCBI database for *Nostoc punctiforme* and *Anabaena variabilis*. Therefore some PAL enzymes can be mislabeled HAL enzymes. Although the active sites of PALs and HALs are very similar, they are predicted to differ in some key residues (Calabrese et al., 2004; Xiang & Moore, 2002; Williams et al., 2005). Particularly in HAL, the methionine 383 and glutamic acid 415 from *Pseudomonas putida* (SEQ ID NO:8) are highly conserved in all HALs but are always replaced in all the PALs described so far (eukaryotic or prokaryotic) by lysine and glutamine respectively (FIG. 4). So it can be said that all proteins with a "PAL-HAL" region and having the homologues of lysine 383 and glutamic acid 415 have the sequence signature of a protein with PAL activity. This relatively newly described PAL signature (Williams et al., 2005) allows to label properly some enzymes from HAL to PAL and could be used to identify some new PAL enzymes from already published genes and proteins database.

The present invention relates to compositions of such prokaryotic PAL and biologically active fragments, mutants and variants thereof and their uses for therapeutic and industrial purposes.

A. DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry 3rd Ed." Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Amino acids may also be grouped as follows:
(1) hydrophobic: met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel, et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (Thompson, et al. CLUSTAL W: improving the sensitivity of progressive multiple sequence alignment through sequence weighting, positions-specific gap penalties and weight matrix choice, Nucleic Acids Research 22: 4673-4680 (1994)).

Another example of algorithm that is suitable for determining percent sequence identity and sequence similarity is the BLAST algorithm, which is described in Altschul, et al., J. Mol Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, the conjugates of the invention are substantially pure or isolated with respect to the macromolecular starting materials used in their synthesis. In some embodiments, the pharmaceutical composition of the invention comprises a substantially purified or isolated conjugate of a RAP polypeptide and the active agent admixed with one or more pharmaceutically acceptable excipient.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Wild-type" (wt) is a term referring to the natural genetic form of an organism. A wild type is distinguished from a mutant form (an organism with a genetic mutation).

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein, which includes modifications, such as deletions, additions and substitutions (generally conservative in nature), to the native sequence, so long as the protein maintains the desired activity. These modifications may be deliberate, as through site-directed mutagenesis, or may be accidental, such as through mutations arising with hosts that produce the proteins or errors due to PCR amplification.

As used herein, an "analogue" or "derivative" is a compound, e.g., a peptide, having more than about 70% sequence but less than 100% sequence similarity with a given compound, e.g., a peptide. Such analogues or derivatives may be comprised of non-naturally occurring amino acid residues, including by way of example and not limitation, homoarginine, ornithine, penicillamine, and norvaline, as well as naturally occurring amino acid residues. Such analogues or derivatives may also be composed of one or a plurality of D-amino acid residues, and may contain non-peptide interlinkages between two or more amino acid residues.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a PAL polypeptide and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

B. STRUCTURE-BASED PROTEIN ENGINEERING

Numerous methods are known for protein engineering using rational optimization based primarily on protein structural information (Brannigan, et al., (2002) ibid.; 735 Marshall, et al., Drug Discov. Today, 8(5):212-221 (2003)). Systematic replacement of structural features can lead to improved protein properties and/or a redesign of substrate specificity. Recruitment of function from one member of a gene family into another homologous member can be accomplished by the introduction of a limited number of amino acid substitutions in the immediate substrate binding vicinity. Such improvements in protein function by generating improved protein variants can lead to useful proteins for industrial, agricultural, and therapeutic applications (Bocanegra, et al, Biochemistry, 32(11):2737-2740 (1993); Failla, et al., Fold Des., 1(1):35-42 (1996); Hayes, Proc Natl Acad Sci USA., 99(25):15926-15931 (2002); Voigt, et al., Nat. Struct. Biol., 9(7):553-558 (2002); Malashkevich, et al., Nat Struct Biol., 2(7):548-553 (1995); Wells, et al, Proc Natl Acad Sci USA., 84(15):5167-5171 (1987); Wilks, et al., Science, 242(4885):1541-1544 (1988)).

C. THE STRUCTURE OF PAL

The three dimensional structure of wild-type prokaryotic PAL can be determined using x-ray crystallography. The PAL protein is a homotetramer, with each monomer consisting of mainly alpha-helices and subdivisible into four domains—a central catalytic domain, an N-terminal domain, and a small C-terminal domain with similarity to the *Pseudomonas putida* histidine ammonia-lyase structure (HAL, Schwede, et al., Biochemistry, 38(17):5355-5361 (1999)) plus an additional domain inserted in the C-terminal region that protrudes from the ends of the intact tetramer molecule. The N-terminal first 25 residues are not visible in the structure for all four monomers in the tetramer, and this region is probably disordered. The loop regions between residues 109-123 and 350-353 are disordered for monomer B, with regions 103-123 and 350-353 disordered for monomers A, C, and D in the PAL tetramer. Two other X-ray structures of *Rhodosporidium toruloides* PAL have been determined using trans-cinnamate and NH4 ion addition during the crystallization process, with resolutions of 2.1 Å (P3221 space group) and 2.7 Å (P21 space group; Calabrese, et al., Biochemistry 43(36):11403-11416 (2004)). The lower pH used for crystallization and the lower resolution of these structures led to more inherent disorder in the structures (especially in the N-terminal regions) and the inability to unambiguously assign additional electron density present on the MIO cofactor to an NH2 adduct.

There are a number of related structures (using DALI, Holm, et al., J. Mol. Biol. 233:123-138 (1993)) in this family of tetrameric enzymes that catalyze the elimination of various groups from carboxylic acids, including the ammonia-lyases (PAL, HAL, and aspartate ammonia-lyase (AAL)), fumarase, and arginosuccinate lyase (Schwede, et al., Biochemistry, 38(17):5355-5361 (1999)). In addition, the δ-crystallin avian eye lens protein has a similar fold but is a non-enzymatic form of this structural family (Schwede, et al., (1999), ibid.).

The three-dimensional X-ray structures of HAL from *P. putida* (Röther, et al., Eur. J. Biochem. 268:6011-6019 (2001); Schwede, et al., Biochemistry 27:5355-5361 (1999), and more recently of PAL from *Rhodosporidium toruloides* (Calabrese, et al., Biochemistry 43:11403-11416 (2004)), revealed the active site residues of these tetrameric enzymes that are important for substrate binding, catalysis and MIO formation. All active site residues in HAL are present in EncP except for H83 and E414, which are replaced with valine and glutamine residues, respectively (Xiang, L., et al., J. Biol. Chem. 277:32505-3250924 (2002)). H83 in HAL is proposed to bind and orientate the imidazole moiety of L-histidine at the active site and to stabilize an enzyme-bound cationic intermediate, whereas the carboxylate group of E414 may act as a base in catalysis.

The high-resolution three-dimensional protein crystal structure of PAL may be used in methods involving protein engineering to improve the biochemical and biophysical properties of PAL, and to increase the in vivo therapeutic effectiveness of PAL. In addition, the structure provides information regarding which regions of the structure are the most flexible (to remove and generate a more compact and stable form of PAL), which residues are located near the active site (to mutate in order to enhance activity and/or minimize the size of the protein as well as to provide information for structure-based inhibitor design), and which surface locations are close to immunogenic (e.g. linear epitopes identified in mapping studies) and/or proteolytic sensitive sites (from protease mapping studies), allowing for the introduction of site-specific mutants for direct disruption of problem sites or, alternatively, for surface pegylation or other chemical derivatization to protect sensitive sites present in native PAL.

D. USES OF THE STRUCTURE COORDINATES OF PAL

The high-resolution three-dimensional crystal structure of PAL may be used in computerized methods for selecting regions of the protein for mutation, modification, or combined mutation and modification. For example, the commercially available program GETAREA calculates surface-exposure for amino acid residues based upon X-ray crystallographic coordinates.

The high-resolution three-dimensional crystal structure can further be used in in-silico methods to design ligands for the active site of the enzyme. For example, commercially available software programs for docking and designing structure-based small-molecules can be used to design PAL inhibitors (Billett, et al., Biochim Biophys Acta, 524(1):219-230 (1978); Janas, et al., Acta Biochim Pol., 32(2):131-143 (1985); Zon, et al., Phytochemistry, 59(1): 9-21 (2002); Alunni, et al., Arch Biochem Biophys., 412(2):170-175 (2003))

Structure-Based PAL Engineering

The elucidation of a reliable three-dimensional structure or structural model for a specific macromolecule permits rational design to become a productive method for optimization of specific structure and/or function of said macromolecule (Penning, et al., Chem Rev., 101(10): 3027-3046 (2001)). Optimization approaches include but are not limited to re-engineering of coenzyme specificity (Bocanegra, et al., Biochemistry, 32(11):2737-2740 (1993)), improvement of protein stabilities (Malakauskas, et al., Nat Struct Biol., 5(6): 470-475 (1998); Jiang, et al., Protein Sci., 10(7):1454-1465 (2001); Luo, Protein Sci., 11(5):1218-1226 (2002); Filikov, et al., Protein Sci., 11(6):1452-1461 (2002); O'Fagain, Enz Microb Technol. 33:137-149 (2003); Cammett, et al., J Mol Biol. 327(1, pp. 285-297 (2003)), redesign of substrate specificities (Hedstrom, et al., Science 255(5049): 1249-1253 (1992); Failla, et al., Fold Des., 1(1):35-42 (1996); Malashkevich, et al., Nat Struct Biol., 2(7):548-553 (1995); Wilks, et al., Biochemistry, 31(34):7802-7806 (1992); Feil, et al., Protein Eng., 10(3):255-262 (1997); Whittle, et al., J Biol Chem., 276(24):21500-21505 (2001)), alteration of ligand or receptor binding specificities (Cunningham, et al., Proc Natl Acad Sci USA, 88(8):3407-3411 (1991); Reddy, et al., Nat Biotechnol., 14(13):1696-1699 (1996); Doyle, et al., Curr Opin Chem Biol., 4(1):60-63 (2000)), and re-engineering of biological activities (Chen, et al., Proc. Natl. Acad. Sci. U.S.A., 90(12): 5618-5622 (1993); Sarkar, et al., Nat Biotechnol., 20:908-913 (2002); Blatt, et al., J Interferon Cytokine Res., 16(7):489-499 (1996)).

Structure-based engineering can be used to generate PAL variants including rational mutants such as truncations, deletions, insertions, splice variants, point mutations, substitutions, chimeras, loop re-engineered mutants, loop swapping mutants, surface veneering mutants, as well as stochastically-derived mutants (including directed evolution-derived mutants, alone or in combination with rationally developed mutants). In addition, PAL variants can be made comprising PAL mutants wherein mutations have been introduced for site-specific pegylation and/or other chemical derivatizations. The PAL mutants for use in such methods includes any PAL variant having substantially the same functional activity as wild-type *R. toruloides* PAL, including variants, fragments, and chemical derivatives of the parent PAL protein.

Directed Evolution Protein Optimization

Directed evolution methods randomly mutate gene(s) of interest to explore more completely larger regions of protein mutational space. Numerous directed evolution methods exist, including error-prone PCR and random insertion and deletion (RID) mutagenesis to introduce diversity throughout a DNA sequence, and more focused or "directed" diversity-generating methods such as site-saturation mutagenesis and other oligonucleotide-based mutagenesis methods (Brannigan, et al., (2002) ibid.). In addition, DNA sequence recombinational methods have been used to combine advantageous sites of mutation and simultaneously remove deleterious mutations, producing novel DNA sequences (e.g. methods of DNA shuffling, StEP, RACHITT, ITCHY). Finally, structure-based directed evolution techniques have been used to redesign proteins for therapeutic advantage (structure-based combinatorial engineering, SCOPE, and protein design automation, PDA, methods). The SCOPE method is based on a semi-rational protein engineering approach that uses protein structure information coupled with DNA manipulation techniques to design and create multiple crossover protein variant libraries from non-homologous genes (O'Maille, et al., J Mol Biol., 321(4):677-691 (2002)). In PDA, a computational pre-screening of mutational space allows the inclusion of only mutations compatible with a specific protein fold, thus reducing the number of sequence variants to a size amenable to experimental screening (U.S. Pat. No. 6,403,312; Dahiyat, et al., Proc Natl Acad Sci, USA., 94(19): 10172-10177 (1997); Dahiyat, et al., Protein Sci., 6(6):1333-1337 (1997); Hayes, et al., Proc Natl Acad Sci USA., 99(25): 15926-15931 (2002) Orencia, et al., Nature Struct Biol, 8:238-242 (2001).

A large number of examples exist where the use of directed evolution (with coupling to an effective selection or screening protocol) has led to improved catalytic function and biophysical properties (e.g. reduced immunogenicity, increased stability), starting from an initial enzyme species and mutating that species for altered and/or improved function (Vasserot, et al., Drug Discovery Today, 8(3):118-126 (2003)). For example, successful mutants have been obtained using directed evolution and other "random" mutagenesis methods on a number of different proteins (Triose-phosphate isomerase, Hermes, et al., Proc Natl Acad Sci USA, 87(2): 696-700 (1990); Beta-lactamase, Stemmer, W. P., Nature, 370(6488):389-391 (1994), Orencia, M. C., et al., Nature Struct Biol, 8:238-242 (2001), Voigt, C. A., et al., (2002) ibid; para-nitrobenzyl esterase,) Moore, et al., Nature Biotechnol., 14:458-467 (1996); Galactosidase to fucosidase, Zhang, et al., Proc Natl Acad Sci USA, 94(9):4504-4509 (1997); Aspartate aminotransferase, Yano, et al., Proc Natl Acad Sci USA, 95(10):5511-5515 (1998); Green fluorescent protein, Crameri, et al., Nat Biotechnol, 14(3):315-319 (1996); Horseradish peroxidase, Lin, et al., Biotechnol Prog, 15: 467-471 (1999); Cytochrome P450, Joo, et al., Nature, 399(6737): 670-673 (1999); Biphenyl dioxygenase, Kumamaru, et al., Nat Biotechnol, 16(7):663-666 (1998); Arsenate detoxification pathway, Crameri, et al., Nat Biotechnol, 15(5):436-438 (1997); Cephalosporinase, Crameri, et al., Nature, 391(6664):288-291 (1998); various proteins, Shao, et al., Curr Opin Struct Biol, 6(4):513-518 (1996), various proteins, Skandalis, et al., Chem Biol, 4, pp. 889-898 (1997); Subtilisin, Cunningham, et al., Protein Eng., 1(4):319-325 (1987); Nitrilase, DeSantis, et al., J Am Chem. Soc., 125(38):11476-11477 (2003); Alpha-aspartyl dipeptidase, Kong, et al., Biochem Biophys Res Commun., 289(1):137-142 (2001); Aspartate aminotransferase, Rothman, et al., Protein Science, 13(3):763-772 (2004); L-aspartase, Wang, et al., Biochem Biophys Res Commun., 276(1):346-349 (2000); and lactate dehydrogenase, Wilks, et al., Biochemistry 31(34):7802-7806 (1992).

These studies have repeatedly demonstrated the utility of applying "random" mutagenesis techniques to the development of improved enzyme variants with increased stability, activity, and resistance to degradative pathways. Structural analysis of evolved protein clones leads to insight on the molecular changes that are involved with the improved physical and chemical properties that are obtained (Orencia, et al., in Advances in Protein Chemistry: Evolutionary protein design, F. H. Arnold, Editor, Academic Press: San Diego, pp. 227-259 (2001)). The rewards to be gained with directed evolution techniques are especially evident in light of the repeated occurrence of beneficial mutations that involve non-active site residues, with some sites of mutation located over 15-20 Å from enzyme active site regions having beneficial effects (Oue, et al., J. Biol. Chem., 274(4):2344-2349 (1999)). Directed evolution and other random mutagenesis techniques, coupled to selection and screening procedures, can be used to develop more proteolytically stable and chemically robust forms of PAL to be used in industrial applications or, alternatively, for enzyme substitution therapy, e.g. for PKU.

E. MODIFIED PAL

Previous experiments have described modified forms of PAL, such as PAL mutants (Schuster, et al., FEBS Lett., 349(2):252-254 (1994); Schuster, et al., Proc Natl Acad Sci USA., 92(18):8433-8437 (1995); Langer, et al., Biochemistry, 36:10867-10871 (1997); El-Batal, et al., Acta Microbiol Pol., 49(1):51-61 (2000); Röther, et al., Eur. J. Biochem. 269:3065-3075 (2002)) and HAL mutants (Taylor, et al., J. Biol. Chem., 269(44):27473-27477 (1994); Baedeker, et al., Eur. J. Biochem., 269(6):1790-1797 (2002)).

Optimization of PAL Kinetics—Prokaryotic Mutants with Enhanced Catalytic Activity The biologically active sites of wild-type PAL according to the invention may be modified as desired to optimize PAL kinetic characteristics. Km, the concentration of substrate that gives half-maximal activity, is intimately associated with the therapeutic efficacy of PAL in maintaining phe levels within an acceptable range, i.e. 120 uM to 240 uM. Km is the affinity of the enzyme for the substrate. By controlling affinity, one can limit or control the efficacy of any enzyme against substrate at different concentrations. For example, if Km is 1000 uM (*Rhodosporidium toruloides*), the activity of the enzyme will be reduced to about 12.5% at blood phe levels of 240 uM and to about 3% at blood phe levels of 60 uM. If Km is 240 uM, the activity of the enzyme will be reduced to about 50% at blood phe levels of 240 uM and to about 12% at blood phe levels of 60 uM. If Km is 120 uM, the activity of the enzyme will be reduced to about 70% at blood phe levels of 240 uM and to about 35% at blood phe levels of 60 uM. Optimally, a preferred therapeutic objective would be to have an enzyme with sufficient activity to reduce but also maintain phe within the optimal range of about 120 uM to about 240 uM. An enzyme with a high Km (i.e. 1000 uM) will lose activity rapidly as phe levels drop to within normal range and will also require the impractical administration of highly concentrated or large volumes of doses. On the other hand, an enzyme with a very low Km may rapidly deplete phe levels, which may be fatal for hyperphenylanemias but may be useful in the management of cancer.

In most preferred embodiments, the biologically active modified mutant PAL has a kcat of at least about 4.0 s−1 and preferably greater than 20 s−1. In other preferred embodiments, the biologically active modified PAL has a Km of between about 100 µM to about 1000 µM. In most preferred embodiments, the biologically active modified PAL exhibits enzymatic activity that is from about two-fold to about 1000-fold times greater that that of the wild-type. Such biological active mutants may be formed using methods well known in the art, such as by site-directed mutagenesis.

All active site residues in HAL were shown to be present in EncP except for H83 and E414, which are replaced with valine and glutamine residues, respectively (Xiang, L., et al., J. Biol. Chem. 277:32505-32509 (2002)). The role of H83 in HAL in binding and orientating the imidazole moiety of L-histidine at the active site and in stabilizing an enzyme-bound cationic intermediate was investigated (Xiang, Longkuan and Moore, Bradley S., Biochemical characterization of a prokaryotic phenylalanine ammonia lyase, J. Bacteriology 187(12):4286-4289 (2005)). It was proposed that the carboxylate group of E414 may act as a base in catalysis. In the study, EncP mutants were generated by site-directed mutagenesis to assess the contribution of V83 to cinnamic acid formation by EncP. Replacement of valine with histidine generated a mutant, V83H, which was characterized by a loss in PAL activity. Replacement of the valine with alanine resulted in a mutant, V83A, which was more active than the wild-type EncP V83A had a slightly lower affinity to L-phenylalanine with a Km of 120 µM versus 23 µM for the wild-type enzyme. However, in comparison with wild-type EncP, V83A had a higher kcat higher and was more active than the wild-type enzyme Specific Protein Variants: Variants Having Reduced Immunogenicity A number of strategies are currently used to reduce protein immunogenicity. Preferably, modifications that are introduced to minimize the immune response do not destroy the structure, function, or stability of the macromolecule. Effective strategies used include increasing human sequence content (chimeras and/or other 'humanization' approaches), improving solution properties, removing antibody epitopes, introducing chemical derivatization (such as pegylation), and/or identifying and removing MHC agretopes. For an injected therapeutic, in vivo immunoreactivity can be addressed by performing epitope mapping followed by rational mutagenesis to modify and/or otherwise mutate these sites of immunogenicity, alone and in combination with site-specific pegylation (Hershfield, et al., (1991) ibid.; Leong, et al., (2001) ibid.; Lee, et al., Pharm. Res., 20(5):818-825 (2003)) or other chemical derivatization methods to reduce protein immunoreactivity to an acceptable level.

Modification of antigenic surface protein regions reduces immunogenicity (Chirino, et al., (2004) ibid.). One method of improvement involves the construction of smaller sized proteins that retain catalytic activity (e.g. an absorbance assay is used for activity measurement). A second method of improvement, protein engineering coupled to ELISA screening, can also be used to identify mutants with reduced immunoreactivity. Another method introduces point mutations for additional surface Lys sites for pegylation derivatization, a method shown to reduce immunogenicity with the test enzyme purine nucleoside phosphorylase (Hershfield, et al., (1991) ibid.). An alternative pathway uses mutation of residues located in protein epitope regions to remove immunogenic sites (Yeung, et al., J Immunol., 172(11):6658-6665 (2004)). In an approach that is analogous to antibody humanization, homologous loop regions and/or residues from human antibodies are substituted into the corresponding loop regions of a homologous protein.

Removal of protein therapeutic proteolytic processing sites can also provide a reduction in immunogenicity by preventing proteasomal processing, thereby preventing clipping and processing into peptide fragments for antigen presenting cell binding. A similar phenomenon has been observed in the alteration of flanking regions for class II MHC determinants, preventing display to autoreactive T cells (Maverakis, et al., Proc Natl Acad Sci, USA., 100(9):5342-5347 (2003)).

Epitope Mapping

Protein therapeutic epitopes can be calculated using a number of algorithms or experimentally determined with in vitro or in vivo approaches. Computer programs such as "Peptide Companion" and "Protean" in the Lasergene program suite from DNAStar are commonly used to estimate surface epitope regions of a protein based on the chemical composition and conformation of a protein. Immunogenic regions in a protein sequence are those regions of highest calculated hydrophilicity, based on a hydrophilicity index, and antigenicity, based on the amphipathicity and other conformational parameters of calculated surface protein regions. Alternatively, agretopes in a protein sequence can be located based on computer-modeled predictions of potential HLA binding (Robinson, et al., Nucleic Acids Res., 31(1):311-314 (2003); De Groot, et al., Novartis Found. Symp., 254:57-72 (2003)). In addition, epitopes can be identified using in vitro biochemical (Tangri, et al., (200) ibid.) and in vitro cell-based methods (Stickler, et al., J Immunother., 23(6):654-660 (2000); Stickler, et al., J Immunol Methods, 281(1-2):95-108 (2003)). For protein engineering, the relative reduction in immunogenicity can be monitored using assays similar to the in vitro cell-based assay of Stckler, et al. (Toxicol Sci., 77(2): 280-289 (2004)).

Pepscan analysis (epitope mapping) involves use of a library of overlapping peptides covering surface regions of the enzyme sequence and probing with rabbit polyclonal antibodies raised against overlapping peptides covering the entire enzyme protein sequence, and thereby reveal linear epitopes present in the enzyme. Based on the three-dimensional structure of the enzyme, the experimentally-identified sites of antigenicity are mutated by either randomly mutating epitope region residues to remove the epitope recognition sites or using site-specific mutation to introduce Lys or Cys residues on the surface near these epitope sites to provide locations for pegylation to cover and protect these sites from immunogenic recognition. ELISA screening of these potentially non-immunogenic enzyme mutants (or pegylated forms of these enzyme mutants) provides in vitro identification of subsets of enzyme mutants that display decreased immunoreactivity.

Surface Residue Identification and Mutation

The surface-exposed residues in or near the immunogenic regions of the enzyme can be identified. These locations will be a subset of the total number of solvent-accessible surface locations present in the protein, dependent upon proximity to the surface as well as proximity to regions of immunogenicity/antigenicity. The three-dimensional structure of the protein, determined using X-ray crystallography, NMR, or homology modeling, can be used in commercially available software programs to calculate macromolecule solvent-accessible surface area. The output provided using the program GETAREA 1.1 (Fraczkiewicz, et al., J. Comp. Chem., 19:319-333 (1998)) gives a reliable estimate of surface accessibility for R. toruloides PAL. GETAREA and PARAREA and similar programs calculate solvent-accessible surface area using continuum methods with a parametric approach based on the Gauss-Bonnet theorem. PARAREA finds potential intersection points in the Gauss-Bonnet path using all atom pairs in the neighbor list of each atom, whereas GETAREA more efficiently calculates the solvent-exposed vertices using intersection half-spaces defined by planes of two-sphere intersections.

In native PAL, GETAREA identified twelve surface-exposed Lys residues, distributed throughout the tetrameric PAL protein surface, as well as one partially-exposed surface Cys residue (Cys140). These positions are directly available for pegylation derivatization. Further, the three-dimensional structure of PAL can be used to identify additional surface residues available for site-directed mutagenesis. These additional sites can be mutated using standard protein engineering techniques to generate more favorable PAL mutants with reduced immunogenicity, improved proteolytic resistance, and/or improved stability/activity.

Strategies for mutation of the protein to provide protein mutants with improved properties, such as reduced immunogenicity are known in the art. One popular route mutates every non-alanine residue in an epitope to Ala, and mutate every alanine residue in an epitope to Gly. Other methods remove charged and hydrophobic residues from epitope regions, either by mutation or deletion. Additional mutation strategies introduce site-specific mutations followed by site-specific chemical derivatization.

Truncations can also be used for the production of protein improvements. Bioinformatics analysis of PAL relative to histidine ammonia-lyase (HAL) has suggested truncation mutants (residues 23-716 and 1-564). In addition, analysis of the PAL 3-D structure provides an alternative region for truncation, based on the absence of a C-terminal domain region in the structure of the highly homologous HAL protein. C-terminal domain deletion mutants, including mutants where the corresponding loop region from HAL is fused into the PAL sequence to substitute for the C-terminal domain protruding region of the PAL structure (calculated to have major epitope regions), form smaller, more robust, and predicted less immunogenic variants of PAL.

In another method, protein engineering using rational mutagenesis in combination with directed evolution can be used to obtain mutant forms of PAL. For example, implementation of rational design along with experimental and combinatorial design has improved the activity of compstatin (Morikis, et al., Biochem. Soc. Trans., 32(Pt 1):28-32 (2004)). The combination of rational mutagenesis and directed evolution has also shown promise (Bomscheuer, et al., Curr. Opin. Chem. Biol., 5(2):137-143 (2001); Dwyer, et al., Science, 304(5679):1967-1971 (2004)).

Mutant forms of PAL that display less than optimal enzymatic activity can be evolved for activity using the protein engineering method of directed molecular evolution, wherein a random mutagenesis step is followed by a selection procedure for mutants that are active, producing a new protein mutant pool of only those clones that have activity. For example, if a specific mutant PAL (that we have designed to introduce a surface lysine residue near an epitope-containing region of the structure) is inactive, performing directed evolution on this mutant (mutating the inactive mutant and selecting for transformants with activity) generates a new mutant pool containing this beneficial mutation (the surface lysine site) plus a subset of additional random mutations located throughout the structure that restore activity to each active clone. In addition, the directed evolution technique of molecular breeding that can cross different species of the same protein or similar sequences of different proteins (Crameri, et al., Nature, 391:288-291 (1998); Minshull, et al., Curr. Opin. Chem. Biol., 3(3):284-290 (1999)) can substitute the sequence of human histidine ammonia-lyase to replace some of the most immunogenic regions of PAL with a human sequence that won't be recognized by the immune system.

Mutant forms of PAL can be obtained by making hybrid protein variants based on semi-rational approaches thereby allowing for a more directed level of protein design relative to pure directed evolution-based methods, as well as providing for a more random level of mutational manipulation for those regions of a protein structure identified using such biased protein engineering approaches. For example, the PDA method generates computationally pre-screened libraries of protein variants, allowing for more rapid optimization of protein properties over pure random, or non-biased protein engineering methods (U.S. Pat. No. 6,403,312; Dahiyat, Curr Opin Biotechnol., 10(4):387-390 (1999); Filikov, et al., ibid. (2002); Hayes, et al., (2002) ibid.; Luo, P., et al., (2002) ibid.). Similarly, the SCOPE method constructs hybrid enzyme variants based on "equivalent" subdomains of structure, allowing the creation of multiple crossover protein variant libraries starting from non-homologous genes (O'Maille, et al., (2002) ibid.). In a similar fashion, the method developed by Voigt, et al., constructs hybrids based upon the application of a computational algorithm that identifies fragments of proteins, or 'schemas,' that can be recombined without disrupting the integrity of a protein's three-dimensional structure (Voigt, et al., (2002) ibid.). Computational analysis can also identify conserved core regions of structurally and functionally important positions in a protein fold, based on secondary structural element assignments (Mizuguchi, et al., Bioinformatics, 16(12):1111-1119 (2000)). Mutant forms of PAL can be obtained following the procedures of any of the art methods.

HAL as an Alternative Enzyme Substitute

The structure of encP from *Streptomyces maritimus* has been homology modeled based on the structure of *P. putida* HAL. Although smaller than PAL, the structure of *S. maritimus* is more similar to human PAL, making encP a possibly less immunogenic form of an ammonia-lyase to use for PAL protein engineering. An alternative method for obtaining non-immunogenic PAL variants involves mutation of *S. maritimus* encP or other prokaryotic PAL to replace immunogenic sequences by human histidine ammonia-lyase sequences (HAL, Suchi, et al., (1993) ibid.), using mutation followed by selection for encP or other prokaryotic mutants with PAL activity, to obtain a "humanized" encP or other prokaryotic PAL protein that can be further pegylated following the steps of mutation and selection for activity.

Specific Protein Variants: Variants Having Reduced Protease Sensitivity

A number of strategies are currently used to reduce protein protease susceptibility. The modifications introduced to minimize proteolytic sensitivity preferably do not destroy the structure, function, or stability of the macromolecule. Effective strategies include providing an enzyme with an active-site stabilizing species such as a competitive inhibitor (Gilbert, et al. (1981) ibid.; U.S. Pat. Nos. 6,584,644; 6,451,986; 6,433,158; 6,461,849), chemically modifying the amino groups in susceptible Lys and/or Arg sites to block trypsin binding sites, mutating chymotrypsin-sensitive Tyr, Phe, and/or Trp residues to smaller neutral amino acids to abolish cleavage susceptibility, ligate or couple PAL to other protective macromolecules (such as Fc antibody domains or the botulinum neurotoxin nontoxic components), and/or introducing Lys or Cys sites near protease susceptible sites for subsequent chemical derivatization with PEG or other chemically protective and stabilizing groups.

F. CHEMICALLY MODIFIED PAL VARIANTS

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., Curr Opin Biotechnol., 13(4):297-303 (2002)). Preferably, chemical modification is used to reduce immunogenicity. Pegylation is a demonstrated method to reduce immunogenicity of proteins (Bhadra, et al., Pharmazie, 57(1):5-29 (2002)) but glycosylation and other chemical derivatization procedures, using modification with phosphorylation, amidation, carboxylation, acetylation, methylation, creation of acid-addition salts, amides, esters, and N-acyl derivatives are also possible (Davis, Science, 303:480-482 (2004)).

Pegylated Proteins

A series of different pegylation reactions on PAL, using a range of PEG chemical reagent to PAL protein ratios, will provide PEG-PAL derivatives for each modification method. The optimal degree of pegylation can be determined based upon the residual activity obtained for each derivatized PAL species using the absorbance assay in combination with PAGE and Native gel analysis to determine the extent of PEG derivatization. After initial ranges of optimal modification are determined, comparative kinetic analysis (including Vmax and Km determinations, binding constants of substrates, proteolytic stability, pH dependence of activity, temperature-dependence of activity) and immunoreactivity of optimal PEG-PAL species can be determined by ELISA, immunoprecipitation, and Western blot. Protein engineering can also be used to generate the most favorable PAL mutant for pegylation using the optimal derivatization conditions; by minimizing the size of the PAL protein and only modifying the most antigenic regions of the PAL surface, cost of PEG modification will be reduced while at the same time retaining the maximum amount of enzymatic activity and minimum amount of immunogenicity. Similarly, site-specific pegylation can be used to provide enzyme derivatives.

Other chemical modifications such as phosphorylation or other chemical modification of lys, arg, cys residues can be used to mask immunogenic regions and/or proteolytic sensitive regions. Such chemical modifications include the polymer addition method of Bednarsaki and the Altus Corporation cross-linking method for improving PAL stability, reducing immunogenicity, and improving protease resistance are representative examples. Bednarsaki demonstrated that polymer addition improves protein temperature stability (Wang, et al., J. Am. Chem. Soc., 114(1):378-380 (1992)), and Altus Corporation has found that glutaraldehyde cross-linking improves enzyme stability.

To discover if the in vivo therapeutic half-life of a protein such as PAL would benefit from pegylation, a variety of different PEG:PAL conjugates are synthesized, characterized in vitro and tested in vivo for L-Phe reduction. In order to both optimize the potential effects of pegylation and to identify the preferred sites of PEG attachment, a design strategy is employed wherein polymer length, conformation, and the degree of PEG attachment is varied.

Methods for preparing the pegylated PAL of the present invention generally comprise the steps of (a) reacting PAL with polyethylene glycol under conditions whereby PAL becomes attached to one or more PEG groups, and (b) obtaining the reaction product(s). Because the specific sites of PAL modification might significantly alter the intrinsic activity of the conjugate, different types and amounts of PEG were explored. The chemistry used for pegylation of PAL was the acylation of the primary amines of PAL using the NHS-ester of methoxy-PEG (O-[(N-Succinimidyloxycarbonyl)-methyl]-O'-methylpolyethylene glycol). Acylation with methoxy-PEG-NHS or methoxy-PEG-SPA results in an amide linkage that eliminates the charge from the original primary amine.

The present methods provide for a substantially homogenous mixture of polymer:protein conjugate. "Substantially homogenous" as used herein means that only polymer:protein conjugate molecules are observed. The polymer:protein conjugate has biological activity and the present "substantially homogenous" pegylated PAL preparations provided herein are those which are homogenous enough to display the advantages of a homogenous preparation, e.g., ease in clinical application in predictability of lot to lot pharmacokinetics.

The polymer molecules contemplated for use in the pegylation approaches described herein may be selected from among water-soluble polymers or a mixture thereof. The water-soluble polymer may be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), HPMA, Fleximer™, and polyvinyl alcohol, mono-(C1-C10)alkoxy-PEG, aryloxy-PEG, tresyl monomethoxy PEG, PEG propionaldehyde, bis-succinimidyl carbonate PEG, cellulose, or other carbohydrate-based polymers. The polymer selected should be water-soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected and on the number of available reactive groups (typically ε amino groups) present. As relates to molecular weight, in general, the higher the molecular weight of the polymer used, the fewer number of polymer molecules which may be attached to the protein. Similarly, branching of the polymer should be taken into account when optimizing these parameters. Generally, the higher the molecular weight (or the more branches) the higher the polymer:protein ratio. The present invention contemplates several different linear PEG polymer lengths including but not limited to 5 kDa and 20 kDa, conjugates of two-armed branched PEG polymers, including but not limited to 10 kDa and 40 kDa. In general, for the PEGylation reactions contemplated herein, the preferred average molecular weight is about 2 kDa to about 100 kDa (the term "about" indicating +/−1 kDa). More preferably, the average molecular weight is about 5 kDa to about 40 kDa. The ratio of water-soluble polymer to PAL will generally range from 1:1 for monoPEG-, 2:1 for diPEG etc.

Examples 6 through 8 describe the effects of pegylated and nonpegylated forms of lysine mutant R91K PAL from *Rhodosporidium toruloides*, PAL produced by the cyanobacterium *Nostoc punctiforme* (NpPAL), and PAL produced by the cyanobacterium *Anabaena variabilis* (AvPAL) on phenylalanine levels in the ENU2 or BTBR$^{enu2}$ mouse over a 12 day-period. This animal model is a homozygous mutant at the phenylalanine hydroxylase gene (PAH) locus resulting in an animal with severe hyperphenylalanemia. Thus, the high plasma phenylalanine (Phe) levels make this animal the appropriate model for evaluating the ability of phenylalanine ammonia lyase (PAL) to reduce plasma Phe. The effects of pegylated and nonpegylated forms of lysine mutant R91K PAL and NpPAL on phenylalanine levels in this PKU animal model were also evaluated over a 90-day period. The results showed that pegylated forms of NpPAL and AvPAL resulted in greater reduction in phenylalanine in the PKU animal model in comparison with unpegylated NpPAL and AvPAL, respectively. Further, such effects of pegylated NpPAL to reduce elevated phenylalanine levels were maintained over a ten-week period. These studies show that pegylation of PAL from the cyanobacteria, *Nostoc punctiforme* and *Anabaena variabilis* is essential in reducing phenylalanine levels in the PKU affected mice. The findings suggest that a pegylated variant of bacterial PAL may serve as an effective therapeutic in the management of PKU.

G. SELECTION AND SCREENING ASSAYS

For production and screening of active PAL or HAL variants, initial mutant clone expression can utilize any of the known vector expression systems, such as the His-tag vector expression system, facilitating a high-throughput metal chelate purification step for protein variant isolation. A three-tier screening system can be used to identify favorable protein variants. Initial positive clone identification can use transformation and selection for growth in a phenylalanine auxotrophic *E. coli* strain. A second round of screening can utilize the OD290 absorbance measurement (Hodgins, (1968) ibid.) amenable to high-throughput processing. Finally, screening for proteolysis resistance (using incubation in the presence of protease cocktail) or, alternatively, immunogenicity reduction (using competitive ELISA measurements), can be used to identify favorable protein variants.

H. THERAPEUTIC USES AND ADMINISTRATION OF OPTIMIZED PAL PROTEINS

1. Various Forms of Hyperphenylalanemia (HPA)

The present invention is directed to the treatment of a variety of HPA patient populations with methods that comprise the use of PAL compositions, either alone or in combination with other therapeutic regimens, for managing HPA and/or PKU. In particular, it is contemplated that PAL compositions may be used to treat that patient population with phenylalanine concentrations that are low enough that dietary intervention is not normally used (i.e., patients with mild HPA), patients with moderate PKU, patients with classic or severe PKU, and any subpopulations thereof. Such patients that are amenable to treatment with PAL compositions to ameliorate the effects of mild HPA, include pregnant women and infants with serum concentrations of less than 200 µM. The various patient populations, and their different therapeutic needs, are discussed in further detail in the present section.

Certain embodiments of the present invention are directed to treating classic severe PKU by administering to the subject a protein-restricted diet in combination with a composition comprising PAL or biologically active variants, mutants, and fragments thereof, wherein the combined administration of the protein-restricted diet and PAL is effective to lower the phenylalanine concentration in the plasma of said subject as compared to said concentration in the absence of said combined administration. In addition, the invention also contemplates treating a pregnant female that has HPA by administering to the female a protein-restricted diet in combination with PAL or a biologically active derivative thereof, such that the combined administration of the protein-restricted diet and PAL is effective to lower the phenylalanine concentration in the plasma of the pregnant woman as compared to such a concentration in the absence of said combined administration. In specific embodiments, therapy is contemplated for patient who manifest Phe levels greater than 420 µM Other embodiments of the invention entail administering a PAL composition to any individual that has HPA, characterized by a plasma Phe concentration greater than 180 µM prior to the administration of PAL, in an amount effective to produce a decrease in such a plasma Phe concentration of the patient. The methods of the invention will be useful in treating an infant having PKU characterized by an elevated Phe concentrations of between greater than 300 µM with PAL compositions described herein. By "infant" the present application refers to a patient that is between the ages of 0 to about 36 months.

Characteristics of Severe Classical PKU and Methods of Treatment Thereof According to the Present Invention.

Severe PKU manifests in a plasma Phe concentration greater than 1200 µM and may be found to be as high as 4800 µM. Patients that have this disorder must be treated with a Phe-free diet in order to bring their plasma Phe concentrations down to a level that is clinically acceptable (typically, less than 600 µM and preferably less than 300 µM). These patients are only able to tolerate a maximum of between 250-350 mg dietary Phe per day (Spaapen et al., Mol. Genet and Metab. 78:93-99, 2003). As such, these patients are started on a Phe-restricted formula diet between 7-10 days after birth and are burdened with this dietary restriction for the remainder their lifespan. Any alleviation of the strict dietary restrictions that these individuals are encumbered with would be beneficial.

The tests used for the diagnosis of individuals with classical Phe are described in further detail below. These tests have revealed that patients with classical severe PKU require a low phenylalanine diet (Lucke et al., Pediatr. Neurol. 28:228-230, 2003). Thus, it is contemplated that the methods of the invention will entail determining that the patient is suffering from classical PKU by monitoring the plasma Phe concentration of the individual. The patient is then treated by administering prokaryotic PAL compositions alone or a combined regimen of a low protein diet and PAL such that there is produced at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with severe classical PKU has a Phe concentration of 4800 µM a 90% decrease in the Phe concentration will produce a plasma Phe concentration of 480 µM, a concentration that is sufficiently low to require little dietary restriction). Of course, it should be understood that the treatment methods of the present invention (whether for treating severe classical PKU or any other HPA described herein), should attempt to lower the plasma Phe concentrations of the patient to levels as close to a range of about 120 µM to about 360 µM±15 µM as possible, and most preferably to an optimal range of about 120 µM to about 240 µM.

In preferred embodiments the plasma Phe concentrations of the classical PKU patient being treated is reduced from any amount of unrestricted plasma Phe concentration that is greater than 1000 µM to any plasma Phe level that is less than 600 µM. Of course, even if the combined treatment with PAL and the protein-restricted diet produces a lesser decrease in plasma Phe concentration, e.g., to a level of between 800 µM to about 1200 µM, this will be viewed as a clinically useful outcome of the therapy because patients that have a plasma Phe concentration in this range can manage the disease by simply restricting the amount of protein in the diet as opposed to eating a Phe-restricted formula, thereby resulting in a marked improvement in the quality of life of the individual, as well as leading to greater patient compliance with the dietary restriction.

Any increase in the amount of dietary Phe levels that can be tolerated by the patient as a result of the treatment will be considered to be a therapeutically effective outcome. For example, it is contemplated that as a result of administering the PAL therapy, the patient will be able to increase his/her intake of dietary Phe from 250-350 mg/day to 350-400 mg/day (i.e., the Phe tolerance phenotype of the patient is altered from that of a classic PKU patient to a moderate PKU patient). Of course, it would be preferable that the therapeutic intervention taught herein would allow the patient to increase his/her intake of dietary Phe from 250-350 mg/day to 400-600 mg/day (i.e., the Phe tolerance phenotype of the patient is altered from that of a classic PKU patient to a mild PKU patient), or even more preferably, to allow the patient to have an intake of greater than 600 mg Phe/day (i.e., normal dietary intake).

Characteristics of BH4-Non Responsive PKU Patients and Methods of Treatment Thereof According to the Present Invention.

A second group of patients that can be treated with the methods of the present invention are those individuals that have been determined to have an elevated plasma Phe concentrations i.e., any concentration that is greater than 200 µM, but have been diagnosed to be non-responsive to BH4 therapy (as determined by the BH4 loading test described below). Such patients may include those individuals that have mild PKU (i.e., plasma Phe concentrations of up to 600 µM), individuals that have moderate PKU (i.e., plasma Phe concentrations of between 600 µM to about 1200 µM), as well as patients that have classic severe PKU (i.e., plasma Phe concentrations that are greater than 1200 µM).

The patients that are non-responsive to BH4 therapy are given PAL in combination with a reduced amount of protein in their diet in order to decrease the plasma Phe concentrations of the patient. The methods of the present invention are such that the administration of PAL produces a greater decrease in the plasma Phe concentrations of the patient as compared to the decrease that is produced with the same dietary protocol administered in the absence of PAL therapy. The dietary restrictions may be a diet that restricts the Phe intake by providing a synthetic medical protein formula that has a diminished amount of Phe or alternatively, the dietary restriction may be one which simply requires that the patient limit his/her overall protein intake but nevertheless allows the patient to eat normal foodstuffs in limited quantities.

The preferred therapeutic outcomes discussed for classical PKU patients are incorporated into the present section by reference. Preferred therapeutic outcomes for patients with moderate PKU (i.e., patients that has an unrestricted plasma Phe concentration of 600 μM/L to 1200 μM) include at least a 25% decrease in the plasma Phe concentrations of the patient. Preferably, the method will produce a 30% decrease in the plasma Phe concentration. Even more preferably, the method will produce a 40%, 50%, 60%, 70%, 80%, 90% or greater decrease in the plasma Phe concentration of the individual (for example, where a patient with moderate classical PKU has a Phe concentration of 1000 μM, a 90% decrease in the Phe concentration will produce a plasma Phe concentration of 100 μM, a concentration that is sufficiently low to require little or no dietary restriction).

In preferred embodiments, the plasma Phe concentrations of the moderate PKU patient being treated is reduced from any amount of unrestricted plasma Phe concentration that is between 600 μM to 1200 μM to any plasma Phe level that is less than 300 μM. A particularly preferred treatment with PAL (either alone or in combination with a dietary restriction) produces a decrease in plasma Phe concentration, e.g., to a level of between 200 μM to about 400 μM, which will be viewed as a clinically useful outcome of the therapy because patients that have a plasma Phe concentration in this range can manage the disease by simply restricting the amount of protein in the diet as opposed to eating a Phe-restricted formula. Indeed, in many studies, it is taught that such patients may even eat a normal diet.

Any increase in the amount of dietary Phe levels that can be tolerated by the patient as a result of the treatment will be considered to be a therapeutically effective outcome. For example, it is contemplated that as a result of administering the PAL therapy (either alone or in combination with other therapeutic intervention), the patient will be able to increase his/her intake of dietary Phe from 350-400 mg/day to 400-600 mg/day (i.e., the Phe tolerance phenotype of the patient is altered from that of a moderate PKU patient to a mild PKU patient). Of course, it would be preferable that the therapeutic intervention taught herein would allow the patient to increase his/her intake of dietary Phe from 350-400 mg/day to 400 to allow the patient to have an intake of greater than 600 mg Phe/day (i.e., normal dietary intake).

Even if the patient being treated is one who manifests only mild PKU, i.e., has a dietary allowance of 400-600 mg Phe intake/day) will benefit from the PAL-based therapies of the present invention because it is desirable to produce a normalized plasma Phe concentration that is as close to 360 μM±15 μM as possible. For such patients, a preferred therapeutic outcomes will include at least a 25% decrease in the plasma Phe concentrations of the patient. Preferably, the method will produce a 30% decrease in the plasma Phe concentration. Even more preferably, the method will produce a 40%, 50%, 60%, or greater decrease in the plasma Phe concentration of the individual (for example, where a patient with mild PKU has a Phe concentration of 600 μM, a 60% decrease in the Phe concentration will produce a plasma Phe concentration of 360 μM, i.e., an acceptable, normal concentration of plasma Phe).

In preferred embodiments, the plasma Phe concentrations of the mild PKU patient being treated is reduced from any amount of non-restricted plasma Phe concentration that is between 400 μM to 600 μM to any plasma Phe level that is less than 100 μM. Of course, even if the treatment with PAL (either alone or in combination with a dietary restriction) produces a lesser decrease in plasma Phe concentration, e.g., to a level of between 200 μM to about 400 μM, this will be viewed as a clinically useful outcome of the therapy.

Any increase the amount of dietary Phe levels that can be tolerated by the patient as a result of the treatment will be considered to be a therapeutically effective outcome. For example, it is contemplated that as a result of administering PAL therapy (either alone or in combination with other therapeutic intervention), the patient will be able to increase his/her intake of dietary Phe from 400-600 mg/day (i.e., the Phe tolerance phenotype of the patient is altered from that of a mild PKU patient to a mild HPA patient) to allow the patient to have an intake of greater than 600 mg Phe/day (i.e., normal dietary intake).

Furthermore, even if the patient is one who only manifests the symptoms of non PKU HPA, i.e., has an elevated plasma Phe concentration of up to 600 μM, but is otherwise allowed to eat a normal protein diet will benefit from PAL therapy of the invention because it has been shown that elevated Phe concentrations have significant effects on the IQ of such individuals. Moreover, as discussed below, PAL therapeutic intervention of subjects with special needs, e.g., pregnant women and infants, is particularly important even if that patient's plasma Phe levels are within the perceived "safe" level of less than 200 μM.

Maternal PKU and Methods of Treatment Thereof According to the Present Invention.

Metabolic control of plasma Phe levels in PKU women planning conception and those who are pregnant is important because of the serious consequences to the fetus exposed to even moderately elevated Phe levels in utero, regardless of the PAH status of the fetus. Therapeutic control of plasma Phe concentration is especially important in the first trimester of pregnancy, as failure to achieve adequate control will result in disorders including microcephaly, mental deficiency and congenital heart disease.

For example, the NIH Consensus Statement (vol 17 #3, October 2000) on Phenylketonuria reported that exposure of a fetus to maternal Phe levels of 3-10 mg/dL produced a 24% incidence of microcephaly, whilst those exposed to greater than 20 mg/dL (i.e., greater than 1200 μM) had a 73% incidence of microcephaly. Likewise congenital heart disease was found in over 10% of children exposed to maternal Phe levels that were greater than 20 mg/dL. Importantly, it has been noted that levels of Phe greater than 6 mg/dL significantly decrease the IQ of the child. Thus, it is imperative to ensure that the plasma Phe concentration of women with all forms of phenylketonuria, even those manifesting the mildest HPA, must be tightly controlled in order to avoid the risk of maternal PKU syndrome. However, the acceptable target levels for the plasma Phe concentrations of PKU women that have been used in U.S. clinics have ranged between 10 mg/dL and 15 mg/dL, which are much higher than the 2-6 mg/dL levels recommended for pregnant women or the 1-4 mg/dL that are used in British and German clinics to diminish the risks of developing maternal PKU syndrome.

Another important consideration for pregnant women is their overall protein intake. During pregnancy, it is important that women eat sufficient protein because it has been suggested that a low protein diet during pregnancy will result in retarded renal development and subsequent reduction in the number of nephrons and potentially leads to hypertension in adulthood. (D'Agostino, *N. Engl. J. Med.* 348(17)1723-1724, 2003). The following table provides exemplary guidelines for the recommended total dietary protein intake for various individuals.

TABLE 1

United States Guidelines for dietary protein requirements

| | Age | Recommended Total Protein Intake (g) |
|---|---|---|
| Infant | 6 months or less | 13 |
| | 6 months-1 year | 14 |
| | 1-3 years | 16 |
| Children | 4-6 years | 24 |
| | 7-10 years | 28 |
| Males | 11-14 years | 45 |
| | 15-18 years | 59 |
| | 19-24 | 58 |
| | 25-50 | 63 |
| | 51+ | 63 |
| Females | 11-14 years | 46 |
| | 15-18 years | 44 |
| | 19-24 | 46 |
| | 25-50 | 50 |
| | 51+ | 50 |
| Pregnant | | 60 |
| Lactating | | 65 |

As can be seen from the above exemplary guidelines, in the United States, the recommended protein intake for women of child-bearing age (e.g., less than 51) is from about 44 to 50 g/day, whereas pregnant women require are recommended an intake of about 60 g/day. In Canada and the United Kingdom, the recommended protein intake for pregnant women is in the order of about 70 g/day and 52 g/day. Thus, the need to ensure that the plasma Phe concentration levels of pregnant women are tightly controlled is further complicated by the fact that this group of PKU patient requires more protein than non-pregnant PKU females of comparable age.

In view of the above, it is contemplated that PAL therapies of the present invention will be particularly useful in pregnant women. It is contemplated that a woman suffering from any form of HPA who is pregnant or is contemplating pregnancy will be placed on a course of PAL therapy to ensure that her plasma Phe concentration levels are maintained as close to 180 μM to about 360 μM as possible. Such a course of therapy will preferably allow that woman to increase her level of normal protein intake.

The discussion of levels of plasma Phe concentrations and the degrees to which such Phe concentrations should be decreased discussed herein above in Sections IA and IB are incorporated into the present section for pregnant women.

Managing PKU in Infants and Methods of Treatment Thereof According to the Present Invention.

As discussed herein throughout, it has been determined that an elevation in the plasma Phe concentration in infants (ages zero to 3 years old) results in significant drop in IQ of the child. However, as has been discussed elsewhere in the specification, patients that have an elevated plasma Phe concentration of anywhere up to 400 μM do not normally receive any dietary intervention. Thus, infants at the age of zero to 3 years in age suffer from significant deleterious effects from the present therapies. The instant application contemplates treating any infant having an unrestricted plasma Phe concentration that is greater than 360 μM±15 μM with a therapeutic composition that comprises PAL in order to produce a beneficial decrease the plasma Phe concentration of that subject.

In preferred embodiments, the infant is aged between zero and 3 years of age and has an unrestricted plasma Phe concentration of about 1200 μM prior to the administration of PAL and said administration decreases the plasma Phe concentration. Preferably, the plasma Phe concentration is decreased to from greater than 1800 to about 1500 μM, about 1200 μM, about 1100 μM, about 1000 μM, about 900 μM, about 800 μM, about 700 μM, about 600 μM, about 550 μM, about 500 μM, about 450 μM, 400 μM, about 350 μM, about 300 μM, about 275 μM, about 250 μM upon administration. In other embodiments, the infant is aged between zero and 3 years of age and has an unrestricted plasma Phe concentration of greater than 1200 μM and preferably, this plasma Phe concentration is decreased to about 800 μM, or more preferably to about 500 μM or even more preferably to about 360 μM upon administration of PAL, either alone or in combination with diet. Those of skill in the art would understand that the invention contemplates treating infants with unrestricted plasma Phe concentrations of greater than 360 μM with PAL to produce decreases in such plasma Phe concentrations. The discussion of therapeutic reductions of plasma Phe concentrations above are incorporated herein by reference. Further, any decrease over 10% of the initial unrestricted plasma Phe concentration will be considered a therapeutic outcome for the therapeutic regimens for the infants. It should be understood that the PAL therapies may be combined with dietary restrictions to effect the therapeutic decrease in plasma Phe concentrations in such infants.

Table 2 lists a number of disease conditions wherein administration of therapeutically effective amounts of PAL would be beneficial. Parenteral, oral, or other standard routes of administration and dosage can be determined using standard methods.

TABLE 2

Exemplary disease conditions amenable to PAL protein therapy

Phenylketonuria
Hyperphenylalanemia
Tyrosinemia
Cancer

2. Compositions for Use in the Treatment

The present invention contemplates therapeutic intervention of PKU/HPA. Such intervention is based initially on the use of PAL, which may be used alone or in combination with dietary restrictions. Further PAL and/or dietary restrictions may further be combined with other therapeutic compositions that are designed, for example to combat other manifestations of PKU, such as for example, large neutral amino acids to prevent Phe accumulation in the brain (see Koch et al., Mol. Genet. Metabol. 79:110-113, 2003) or tyrosine supplementation. The present section provides a discussion of the compositions that may be used in the treatments contemplated herein.

PAL Compositions

In general, the present invention contemplates pharmaceutical compositions comprising effective amounts of protein or derivative products of the invention together with pharmaceutically acceptable diluents, stabilizers, preservatives, solubilizers, emulsifiers, adjuvants and/or carriers. Such compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, 18th Ed. (1990, Mack Publishing Co., Easton, Pa. 18042) pages 1435:1712 which are herein incorporated by reference. An effective amount of active ingredient is a therapeutically, prophylactically, or diagnostically effective amount, which can be readily determined by a person skilled in the art by taking into consideration such factors as body weight, age, and therapeutic goal.

The PEG:PAL compositions of the present invention may also include a buffering agent to maintain the pH of the solution within a desired range. Preferred agents include sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. The preferred pH range for the compositions of the present invention is pH 3.0-7.5.

The compositions of the present invention may further include an isotonicity adjusting agent to render the solution isotonic and more compatible for injection. The most preferred agent is sodium chloride within a concentration range of 0-150 mM.

As used herein, and when contemplating PEG:PAL conjugates, the term "therapeutically effective amount" refers to an amount, which gives a decrease in serum L-phenylalanine that provides benefit to a patient. The amount will vary from one individual to another and will depend upon a number of factors, including the overall physical condition of the patient. The amount of PAL used for therapy gives an acceptable rate of serum L-phenylalanine decrease and maintains this value at a beneficial level (usually at least about 30% and typically in a range of 10% to 50%). A therapeutically effective amount of the present compositions may be readily ascertained by one skilled in the art using publicly available materials and procedures.

The invention provides for administering PEG:PAL conjugates less frequently than native PAL. The dosing frequency will vary depending upon the condition being treated, but in general will be about one time per week. It is understood that the dosing frequencies actually used may vary somewhat from the frequencies disclosed herein due to variations in responses by different individuals to the PEG:PAL conjugates; the term "about" is intended to reflect such variations.

The present invention may thus be used to reduce serum L-phenylalanine levels. Most commonly, serum L-phenylalanine levels are increased due to hyperphenylalaninemia. Among the conditions treatable by the present invention include hyperphenylalaninemia associated with phenylketonuria. Also treatable are conditions that may lead to increased serum L-tyrosine levels such as found in tyrosinemia. In addition, numerous cancer-related conditions, where depletion of serum L-phenylalanine and/or serum L-tyrosine levels would be beneficial, may also be treated with the PEG:PAL conjugates of the invention.

PEG:PAL conjugates prepared in accordance with the present invention are preferably administered by injection intraperitoneally, subcutaneously, or intramuscularly. However, it would be clear to one skilled in the art that other routes of delivery could also be effectively utilized using the compositions of the present invention.

The methods described herein use pharmaceutical compositions comprising the molecules described above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sufobutyl ether cyclodextrins) etc. Suitable excipients for non-liquid formulations are also known to those of skill in the art.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences,* 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup.

Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

The PEG:PAL compounds identified described above can be administered to a patient at therapeutically effective doses to treat or ameliorate cardiovascular disease. The toxicity and therapeutic efficacy of such compounds can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are normally preferred.

The data obtained from the cell culture assays and animal studies can be used in formulating a range of dosage for use in humans. The dosage preferably lies within a range of circulating concentrations that include the $ED_{50}$ with little or minimal toxicity. The dosage can vary within this range depending upon the dosage form employed and the route of administration utilized. The therapeutically effective dose can be determined from cell culture assays, and from animal models.

Dietary Protein

In addition to administering PAL and related analogs to HPA/PKU patients, it is contemplated that the dietary protein of the patients also may be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art may use the referenced protein formulas, which are generally free of Phe concentrations. The protein formulas often are supplemented with amino acids that are deficient in PKU patients. Such amino acids include, for example, L-tyrosine, and L-glutamine. It has been suggested that it may be desirable to supplement the diet of PKU patients with valine, isoleucine and leucine (see U.S. Pat. No. 4,252,822). In certain clinical manifestations, the toxic effects of PKU are caused by Phe blocking the brain uptake of other amino acids such as tyrosine and tryptophan. It has been found that supplementing the diet of a PKU patient with excess of such large neutral amino acids blocks Phe uptake into the brain and lowers brain Phe levels. Thus, it is contemplated that for the methods of the present invention, the dietary regimen may further be supplemented with compositions that comprise one or more of these amino acids (Koch et al., Mol. Genet. Metabol. 79:110-113, 2003).

Further, as it is known that L-carnitine and taurine, which are normally found in human milk and other foodstuffs of animal origin, also should be supplied in addition to the protein restriction. In certain embodiments, the L-carnitine may be supplied as 20 mg/100 g of protein supplement, and the taurine may be supplied as 40 mg/100 g protein supplement in order to help supply amounts of these factors normally found in human milk and foods of animal origin.

In addition, those of skill in the art are referred to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the discussion above regarding total protein amounts and desirable plasma Phe concentrations, one of skill in the art will be able to determine the amount of dietary protein restriction that is required and thus adjust the diet of the patient accordingly. Taking for example, a male of about 11-14 years of age, that individual should preferably receive 45 g protein/day. In the event that the individual is one that has severe classic PKU, his unrestricted plasma Phe concentration will likely be greater than 1200 μM, and most, if not all of the dietary protein source for that individual is likely to be from a powdered protein supplement, which preferably lowers his plasma Phe concentrations to less than 600 μM. By administering PAL to that subject, a therapeutic outcome would be one which produces greater decrease in the plasma Phe concentrations of patient or alternatively, the therapeutic outcome is one in which the individual's plasma Phe concentrations is lowered to a similar degree, but that individual is able to tolerate protein from a normal diet rather than from a dietary formula.

Similarly, a male of about 11-14 years of age, is one who has moderate PKU, it may be possible using the methods of the present invention to give him the allotted 45 g protein/day through a normal protein intake rather than a restricted formula. Determining whether the methods of the invention are effective will entail determining the plasma Phe concentrations of the patient on a regular basis to ensure that the plasma Phe concentrations remain below at least 400 μM. Tests for determining such concentrations are described below. Preferably, concentrations of less than or about 360 μM are achieved.

3. Identifying and Monitoring Patient Populations

As discussed herein throughout, it will be necessary in various embodiments of the present invention to determine whether a given patient is responsive to PAL therapy, and to determine the phenylalanine concentrations of the patient both initially to identify the class of PKU patient being treated and during an ongoing therapeutic regimen to monitor the efficacy of the regimen. Exemplary such methods are described herein below.

BH4 Loading Test

The BH4 loading test allows discrimination between patients that have HPA due to a deficit in BH4 or through a deficiency in PAH.

The simplest BH4 loading test is one in which exogenous BH4 is administered and the effects of the administration on lowering of plasma Phe concentrations is determined. Intravenous loading of 2 mg/kg BH4 was initially proposed by Danks et al., (Lancet 1:1236, 1976), as BH4 of greater purity has become available it has become possible to perform the test using an oral administration of BH4 in amounts of about 2.5 mg/kg body weight. Ultimately, a standardized approach was proposed by Niederwieser et al. in which a 7.5 mg/kg single oral dose of BH4 is administered (Eur. J. Pediatr. 138:441, 1982), although some laboratories do still use upwards of 20 mg BH4/kg body weight.

In order for the simple BH4 loading test to produce reliable results, the blood Phe levels of the patient need to be higher than 400 µM. Therefore, it is often customary for the patient to be removed from the PKU diet for 2 days prior to performing the loading test. A BH4 test kit is available and distributed by Dr. Schircks Laboratories (Jona, Switzerland). This kit recommends a dosage of 20 mg BH4/kg body weight about 30 minutes after intake of a normal meal.

Determination of Phe Concentrations

There are numerous methods for determining the presence of Phe in blood (Shaw et al., Analytical Methods in Phenylketonuria-Clinical Biochemistry, In Bickett et al. Eds. Phenylketonuria and Some Other Inborn Errors of Amino Acid Metabolism, Stuttgart, Georg Thiem Verlag, 47-561971,). Typically, phenylalanine and tyrosine concentrations are determined from the serum of a patient using a fluorometric assay. This assay relies on the formation of fluorescent substance when phenylalanine is heated with ninhydrin in the presence of leucylalanine (McCaman et al., J. Lab. Clin. Med. 59:885-890, 1962.)

The most popular method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of bacterial growth thereby yielding an area of bacterial growth that can be correlated to phenylalanine concentration by comparison to similar assays performed using discs containing known amounts of Phe.

Other methods of quantifying Phe concentration include HPLC, mass spectrometry, thin layer chromatography and the like. Such methods can be used to determine the plasma Phe concentration of a patient before the therapy and to monitor the Phe concentration during the therapeutic regimen to determine the efficacy thereof.

It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the PAL and/or dietary protein requirements accordingly.

Combination Therapy

Certain methods of the invention involve the combined use of PAL and dietary protein restriction to effect a therapeutic outcome in patients with various forms of HPA. To achieve the appropriate therapeutic outcome in the combination therapies contemplated herein, one would generally administer to the subject the PAL composition and the dietary restriction in a combined amount effective to produce the desired therapeutic outcome (i.e., a lowering of plasma Phe concentration and/or the ability to tolerate greater amounts of Phe/protein intake without producing a concomitant increase in plasma Phe concentrations). This process may involve administering the PAL composition and the dietary protein therapeutic composition at the same time. This may be achieved by administering a single composition or pharmacological protein formulation that includes all of the dietary protein requirements and also includes the PAL within said protein formulation. Alternatively, the dietary protein (supplement or normal protein meal) is taken at about the same time as a pharmacological formulation (tablet, injection or drink) of PAL. PAL also may be formulated into a protein bar or other foodstuff such as brownies, pancakes, cake, suitable for ingestion.

In other alternatives, PAL treatment may precede or follow the dietary protein therapy by intervals ranging from minutes to hours. In embodiments where the protein and the PAL compositions are administered separately, one would generally ensure that a significant period of time did not expire between the time of each delivery, such that PAL will still be able to exert an advantageously effect on the patient. In such instances, it is contemplated that one would administer the PAL within about 2-6 hours (before or after) of the dietary protein intake, with a delay time of only about 1 hour being most preferred. In certain embodiments, it is contemplated that PAL therapy will be a continuous therapy where a daily dose of PAL is administered to the patient indefinitely. In other situations, e.g., in pregnant women having only the milder forms of PKU and HPA, it may be that PAL therapy is only continued for as long as the woman is pregnant and/or breast feeding.

Further, in addition to therapies based solely on the delivery of PAL and dietary protein regulation, the methods of the present invention also contemplate combination therapy with a third composition that specifically targets one or more of the symptoms of HPA. For example, it is known that the deficit in tyrosine caused by HPA results in a deficiency in neurotransmitters dopamine and serotonin. Thus, in the context of the present invention, it is contemplated that PAL and dietary protein based methods could be further combined with administration of L-dopa, carbidopa and 5-hydroxytryptophan neurotransmitters to correct the defects that result from decreased amounts of tyrosine in the diet.

As the administration of phenylase would not generate tyrosine (unlike administration of PAH), such treatment will still result in tyrosine being an essential amino acid for such patients. Therefore dietary supplementation with tyrosine may be desirable for patients receiving phenylase in combination with the BH4 therapy.

I. SCREENING AND CHARACTERIZATION OF PAL HOMOLOGS

Another aspect of the invention is a screening assay for identifying bacterial PAL that can prevent, ameliorate, or reduce enhanced levels of phenylalanine by contacting a cell containing elevated levels of phenylalanine with the bacterial PAL and determining whether the bacterial PAL reduces such elevated levels of phenylalanine. In certain embodiments, the method is a high throughput assay. In a preferred embodiment, complete genomes of the bacterial species are sequenced and screened for the presence of PAL homologs using a bioinformatics approach. In a more preferred embodiment, genes with homology to encP are identified and BLAST analysis of the related protein sequence is conducted to determine percent identity. Primary sequence alignments of such proteins are assessed for the presence of conserved residues essential for PAL activity. Position 83 (HAL from *P. putida*) of all HAL enzymes is an histidine whereas it is an aliphatic amino acid, preferably Leucine or Valine in enzymes with PAL activity. Analysis at position 83 will elucidate whether HAL annoted enzymes may be mislabeled and have actually demonstrate PAL activity. For example, position 413 is a glutamine (Q) in most HAL enzymes and is followed at position 414 by a glutamic acid (E) in all HAL enzymes. By comparison, position 414 is a glutamine (Q) followed at position 415 by an aspartic acid (D) or an asparaginine (N) in most PAL enzymes identified so far. Representative annotated HAL enzymes which are determined by this bioinformatic method to be most likely mislabeled as prokaryotic PAL enzymes include HAL enzymes from *Rhodobacter sphaeroides* 2.4.1 (ZP 00005404), from *Rubrobacter xylanophilus* DSM9941 (ZP 00188602), from *Photorhhabdus luminescens* subsp. LaumondiiTT01 (NP 930421), from *Thermoanaerobacter tengcongensis* (AA051415).

In a further embodiment, PAL catalytic activity of the protein product of such homologs is confirmed. In a preferred embodiment, the genomes of PAL homologs are PCR amplified and cloned into pHIS8 or a similar vector. The putative PAL proteins are heterologously expressed in *E. coli* as His-tagged proteins, purified and assayed for PAL activity. Assays for PAL activity may include but are not limited to ability to convert phenylalanine to cinnamate in vitro, inability to convert tyrosine to p-coumarate in vitro, assays to test for HAL activity and assays to characterize the kinetics of the enzymes.

J. PRODUCTION OF PROKARYOTIC PAL

Another aspect of the invention is a method of producing prokaryotic PAL. In a preferred embodiment, recombinant PAL is over-expressed as an N-terminal octahistidyl-tagged fusion protein in a vector preferably *E coli* BL21(DE3)/pLysS (Invitrogen) with an inducible promoter such as with IPTG (isopropyl-beta-D-thiogalactopyranoside). Seed culture for a bioreactor/fermenter is grown from a glycerol stock in shake flasks. Such seed culture is then used to spike into a controlled bioreactor in fed-batch mode. Glucose is supplemented and pH is controlled with base (NH4OH) and agitation is up to 1200 rpm. $O_2$ feed keeps dissolved oxygen to greater than 20%. The cells are grown at a temperature of 30° C. until reaching and $OD_{600}$ of 70-100 (~22-25 hrs) and then induced with 0.4 mM IPTG. The temperature is reduced to 22 to 26° C. and grown until activity change is <0.1 IU/ml (approximately 40-48 hrs and an OD6% typically of 200). Cell culture media is typically defined and composed of yeast extract protein, peptone-tryptone, glucose, glycerol, casamino acids, trace salts and phosphate buffering salts. The recombinant PAL product is produced intra-cellularly and not secreted. The bacteria are harvested by continuous centrifugation (Alfa-Laval, Carr, Ceba, or equivalent).

K. PURIFICATION OF PROKARYOTIC PAL

A further aspect of the present invention features a method to purify bacterial PAL or a biologically active fragment, mutant or analog thereof. According to a first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another preferred embodiment, the method to purify the bacterial PAL comprises: (a) Lysis of the bacteria containing recombinant PAL using a pressure homogenizer (but potentially by other physical means such as glass bead lysis); (b) Heat treatment (c) Clarification of this lysate using a second continuous centrifugation step and/or depth filtration (as with Cuono Zeta Plus or Maximizer, Pall Filtron, or Millipore Millistak or Opticao filters) (d) passage through a charcoal filtration step (as with Millipore Millistak 40AC); (e) passage through a final filtration step (as with a Sartorious Sartopore 0.2 µm filter); (f) Passage over a butyl hydrophobic interaction chromatography (as in Toyopearl Butyl 650M from Tosoh Biosciences); (g) passage over a Q ion exchange column (as in a Macroprep High Q from BioRad); (h) recovery of final product by buffer exchange with tangential flow filtration (as with a Sartorious Hydrosart or PES 100 kDa membrane). Those skilled in the art readily appreciate that one or more of the chromatography steps may be omitted or substituted, or that the order of the chromatography steps may be changed within the scope of the present invention. Finally, appropriate sterilizing steps may be performed as desired.

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLE 1

Cloning of *Nostoc punctiforme* and *Anabaena variabilis*

DNA Manipulations

*N. punctiforme* genomic DNA was purchased from ATCC (29133D) and the PAL gene (ZP_00105927) was PCR-amplified from primers 5'-CACTGTCATATGAATATAA-CATCTCTACAACAGAACAT-3' and 5'-GACAGTGGCG-GCCGCTCACGTTGACTTTAAGCTCGAAAAAATATG-3'. The resulting PCR product was digested with NdeI and NotI and the 1.7 kb fragment was ligated into pET-28a(+) and pET-30a(+) (Novagen) for N-His Tagged and untagged, respectively.

*A. variabilis* cells were purchased from ATCC (29413). Genomic DNA was extracted (Qiagen) and the PAL gene (YP_324488) was amplified by SOE-PCR to remove an NheI site. Primer 1 (5'-CACTGTGCTAGCATGAAGACAC-TATCTCAAGCACAAAG-3') and primer 2 (5'-GGAAATTTCCTCCATGATAGCTGGCTTG-GTTATCAACATCAATTAGTGG-3') were used to amplify nucleotides 1-1190 and primer 3 (5'-CCACTAATTGATGT-TGATAACCAAGCCAGCTATCATGGAGGAAATTTCC) and primer 4 (5'-CACTGTGCGGCCGCTTAATGCAAG-CAGGGTAAGATATCTTG-3') were used to amplify nucleotides 1142-1771. These two PCR products were combined to amplify the full-length gene with primers 1 and 4. The resulting PCR product was digested with NheI, blunted with Klenow (NEB), then digested with NotI. The 1.7 kb fragment was ligated into pET-28a(+) and pET-30a(+) (Novagen).

Bacterial Strains and Culture Conditions.

*E. Coli* BL21(DE3) cells (Stratagene) were transformed with pGro7 (TaKaRa) and competent BL21(DE3)pGro7 cells were prepared by the Inoue Method (Sambrook and Russell, 2001). These cells were transformed with pET-28-NpPAL and cultured in 25 ml LB with 50 mg/L kanamycin and 20 mg/L chloramphenicol overnight at 37° C. Twenty milliliters of this culture was seeded into 1 L of LB medium with kanamycin, chloramphenicol, and 500 mg/L L-arabinose and grown at 37° C. At an OD600 of 0.6, the culture was chilled on ice. After 5 minutes the culture was induced with 0.3 mM IPTG and grown for 16 hours at 20° C. Cells were harvested by centrifugation.

BL21(DE3)pLysS cells (Stratagene) were transformed with AvPAL and cultured identically to NpPAL without the arabinose induction.

EXAMPLE 2

Purification of NpPAL and AvPAL

The cultures were centrifuged in a bench-top centrifuge at 5,000 g for 20 minutes and the supernatant discarded. The cell pellets were typically frozen at −70° C. prior to further processing. Upon thawing, the cell pellets were suspended to approximately 80 optical density units (600 nm) in TBS (25 mM tris, 150 mM NaCl, pH 7.8). The cells were lysed by two passes through an APV pressure homogenizer at 12-14,000 psi. The crude lysate was then heat-treated at 55° C. for 2 hours. The lysate is centrifuged at 10,000 g for 30 minutes and the supernatant retained and filtered with a 0.2 μm vacuum filter (Corning).

The PAL was purified from the clarified lysate by passage sequentially over a butyl 650M column (Tosoh BioSciences) and a MacroPrep High Q column (BioRad). The eluted product showed a high level of purity by both SDS PAGE and reverse phase HPLC.

EXAMPLE 3

Generation of Pegylated PAL Variants

Protein Pegylation

Pegylation uses modifications of literature methods (Hershfield, et al., (1991) ibid.; 304; U.S. Pat. No. 6,057,292; 558; Lu, et al., Biochemistry, 40(44):13288-13301 (2001); Nektar Therapeutics, 2003 catalog). Activated PEGs include both the linear PEG succinimidyl succinates (mPEG-SPA, MW 5 kDa or MW 20 kDa) and the branched PEG hydrosuccinimides (mPEG$_2$-NHS ester, MW 10 kDa or MW 40 kDa), which are both capped on one end with a methoxy group and available from Nektar Therapeutics; experimental determination of optimal pegylated proteins is normally required (Veronese, F. M., et al., Journal of Bioactive and Compatible Polymers, 12, pp. 196-207 (1997)). Optimal pegylation conditions are determined using different ratios of PAL:PEG (taking into account the molar ratio of protein along with the number of lysines per protein monomer), different pHs, different buffers, various temperatures and incubation times. High PAL protein:PEG derivatization ratios are necessary since native PAL has a large number of lysines (29 per monomer) and because un-modified PAL displays immunoreactivity upon repeated injection in mice and since naked (wild-type) PAL is quickly inactivated upon exposure to proteases. Pegylation reactions are stopped by freezing at −20° C., and the samples will be analyzed by SDS-PAGE, MALDI-TOF mass spectroscopy, activity assessment, proteolytic sensitivity, and immunoreactivity.

Prior to activity, proteolysis, and immune assessment, and in order to remove excess unreacted PEG, reactions are dialyzed against pH 8.5, 0.05 M potassium phosphate buffer overnight at 4° C. with stirring using Tube-O-Dialyzers (GenoTechnology). After protein concentration is determined using the NI protein assay kit (GenoTechnology), PAL activity measurements will be performed on underivatized and PEG derivatized PAL samples using standard reaction conditions, as previously described. Following in vitro characterization, in vivo trials will be conducted with the most promising pegylated therapeutic candidates using the PKU mouse model.

Characterization

Protein concentration is determined using the PAL extinction coefficient (0.5 mg mL$^{-1}$ cm$^{-1}$) at 280 nm for non-modified protein samples and for pegylated protein samples the concentration is calculated using the NI Protein Assay (GenoTechnology) that includes sample processing to remove non-protein contaminants that might interfere with accurate protein concentration determination.

PEG-PAL products are characterized with MALDI-TOF MS to determine the number of PEG molecules attached to each PAL monomer, as well as characterized using activity assessment and SDS-PAGE and native gel analysis, to assure retention of activity, complete derivatization, and no loss of tetrameric PAL formation, respectively. For PAL and PEG-PAL samples, MALDI-TOF mass spectroscopic analysis requires the use of 0.5 M urea or 0.025 M guanidine-HCl to improve subunit dissociation and the reproducibility of species detection.

PAL Activity Assay

The PAL activity assay is conducted using a Cary UV spectrophotometer (Cary 50) in the kinetics mode. The activity of PAL with L-phenylalanine substrate is assayed at room temperature (25° C.) by measuring the production of trans-cinnamate monitored by the absorbance increase at 290 nm (Hodgins, Biochem. Biophys. Res. Commun., 32:246-253 (1968)). The molar extinction coefficient of trans-cinnamic acid at 290 nm is 10.2381 liter M$^{-1}$cm$^{-1}$. Reaction mixtures contain 22.5 mM phenylalanine in 100 mM Tris-HCl buffer, pH 8.5. For standard measurements the final enzyme concentration is 0.0035 mg/mL, but for kinetic studies the enzyme concentration in the assay is adjusted so that the slope at 290 nm per min is in the range of 0.005 to 0.02. Activity data is expressed as specific activity (μmol×min$^{-1}$mg$^{-1}$). One unit of PAL is defined as that amount of enzyme that produces 1 μmol of trans-cinnamic acid per minute at room temperature.

EXAMPLE 4

Test of In Vitro Half-Life and Immunogenicity

After biochemical characterization, the most promising PEG-PAL candidates are screened for immunoreactivity against antibodies raised by PKU mice injected with native PAL (non-pegylated) using three different and complimentary techniques (Western blot, ELISA, and immunoprecipitation (IP)).

For Western blot analysis, PAL anti-serum (from mice injected with native PAL) is used in a dilution 1:10,000. As a negative control the serum from buffer treated-mice is also used in the same dilution. The secondary antibody, alkaline phosphatase-conjugated goat anti-mouse IgG (Promega), is diluted to 1:5,000 and color is developed using the AP substrate Western Blue (Promega). The ELISA test is performed using Nunc/Immuno Maxisorp plates (Nalge Nunc International) following standard procedures using 1 mg/mL of PAL in PBS and blocking with PBS, 0.05% Tween-20, 2% BSA. The mouse antisera (from native PAL exposed mice) is diluted 1:10,000 in EB block solution (PBS, 0.05% Tween-20, 2% BSA), and a HRP-goat anti-mouse IgG is used as secondary antibody with TMB used for detection at 450 nm.

Immunoprecipitation is used to test for PAL antibody binding. Protein samples (PAL or pegylated PAL) are incubated in TTBS buffer (Tris buffered saline with 0.1% Tween) and PAL activity is measured before adding the antibody sample. Each sample is incubated with 8-fold excess of positive control anti-PAL serum and a duplicate negative control reaction using non-immune mouse serum. After incubation, protein G Sepharose 4 (50%, v/v) is added in excess, taking into account the mouse IgG binding capacity of the beads, and the samples are incubated again at 4° C. overnight with rotation. Supernatants are recovered by centrifugation and the PAL activity of each sample is assayed on the supernatants. The bead pellets are not discarded, so that further analysis by Western blot can be performed. To confirm that antibody-bead binding has occurred, Western blot is used to detect the PAL antigen on the beads. Beads that have been recovered by centrifugation after the PAL binding step are washed several times with TTBS and TBS buffers. Following these rinses, SDS-PAGE loading buffer is added to the beads and the samples are heated at 95° C. for 5 minutes. Samples are then analyzed by Western blot using PAL anti-serum. Enzyme variants showing poor antibody binding have corresponding little PAL in the pelleted bead fractions as detected by Western blot and show higher activities remaining in the supernatant as compared to native un-modified PAL which displays high antibody binding.

EXAMPLE 5

Test of Protease Sensitivity

Protease mapping studies on native PAL from *R. toruloides* have indicated primary sites of proteolytic sensitivity. Removal of such sites may reduce or eliminate proteolytic sensitivity and contribute to the development of an effective PKU enzyme substitute. However, elimination of such sites for proteolytic sensitivity may result in the reduction or loss of enzyme activity.

After protein engineering has created improved PAL (and PEG-PAL) mutants that retain activity, screening for protease resistance using incubation with a trypsin/chymotrypsin protease cocktail, followed by monitoring for retention of activity (via $OD_{290}$ measurement) and reduced protein cleavage (via PAGE gel analysis) allows for the identification of mutants with appropriate in vitro properties to be used for in vivo testing.

Proteolytic stability will be assessed using incubation with a protease cocktail that approximates the intestinal environment and contains 2.3 mM trypsin, 3.5 mM chymotrypsin, 3.05 mM carboxypeptdase A, and 3.65 mM carboxypeptidase B. Proteolysis testing will involve enzymatic incubations, adding proteases to the PAL solutions, to determine the degree of protease sensitivity for the different protein variants being examined (native or mutant protein with or without pegylation or other chemical modification), including time courses of activity retention and stability retention after protease exposure. SDS-PAGE and MALDI-TOF mass spectrometric mapping experiments will be used to determine the location of any protease sensitive sites (Kriwacki, R. W., et al., http://abrf.org/JBT/1998/September98/sep98m_r.html (1980). These mapping results will be important to determine primary sites of protease susceptibility (such as the two primary sites already identified), so that all major sensitivity sites can be removed using pegylation protection and/or mutation to remove and/or protect susceptible regions from the PAL architecture.

EXAMPLE 6

Generation of PEGylated NpPAL and AvPAL

In general, PEGylation for both NpPAL and AvPAL involves mixing the protein with SUNBRIGHT ME-200HS 20 kDa NHS-activated PEG (NOF).

Protocol for PEGylation, Standard "HC" Method Using NHS-Activated 20 kDa Linear Peg 1) The protein was evaluated for the presence of endotoxin. A protein solution (0.1 mL) was diluted in 0.9 ml fresh MQ water and tested with a hand-held Charles River apparatus (EndoPTS) for endotoxin at the 0.5 EU/ml sensitivity level. If endotoxin was greater than 0.5 EU/ml, then endotoxin was reduced initially by Mustang E filtration, followed by Sterogene Etox resin, and less preferably by further chromatographic purification. Reduction was limited but sufficiently useful by passage over DEAE FF (Amersham) at pH 7.8.

2) Concentration and Buffer Exchange of Protein:

The protein was concentrated to greater than 25 mg/ml but less than or equal to 75 mg/ml and buffer exchanged to 50 mM $KPO_4$, pH 8.5. If a spin filter was used to prepare this concentration, the filter was first tested for endotoxin by spinning at reduced speed and time (3000 rpm, 3 minutes) with buffer alone, then testing the retained buffer for endotoxin in the same way as the protein in step 1. The buffer batch record/recipe for 50 mM KPO4, pH 8.5 consisted of water (QS to 1 L), Potassium phosphate dibasic (8.4913 g/L of 48.75 mM), and potassium phosphate monobasic (0.17011 g/L of 1.25 mM). The solution was filtered through a 0.2% filter and stored at room temperature. The concentrated product was slowly filtered (1-2 ml/min) through a Mustang E filter acrodisc. A sample diluted and blanked with sterile TBS, pH 7.5 was measured at A280 to determine protein concentration. The extinction coefficient was 0.83 for NpPAL and 0.75 for AvPAL.

3) PEGylation of NPPAL and AvPAL:

PEG normally stored at −80 C was warmed to room temperature. KPO4 buffer was added to PEG to resuspend by vortexing at maximum speed, and shaking tube hard in hand to ensure all large chunks were suspended. The protein was added to the well-suspended PEG solution within one minute of having first wetted the PEG and mixed by very gentle inversion. Tubes wrapped in aluminum foil were placed on the axis of a rocker and rocked very gently at room temperature for 3 hours. The tubes were filled with TBS (pH 7.5) and sterile filtered. The suspensions were either formulated immediately or stored at 4° C. until ready for formulation.

4) Formulation

The formulation buffer recipe/batch record consisted of water (QS to 1 L), Tris-Base (3.2 mM), Tris-HCl (16.8 mM), and sodium chloride; The buffer solution was filtered through a 0.2µ filter and stored at room temperature. The buffer solution was subjected to tangential flow filtration using a Vivalow 50 (smaller lots) or Vivalfow 200 (larger lots) with an 100 MWCO regenerated cellulose membrane. The solution was flushed with MQ water, 0.1 N NaOH, and 200 mL water again. The solution was equilibrated with TBS, pH 7.5 at 50 mL/min cross-flow. The pH of the permeate was determined to ensure a pH of 7.5.

The solution was buffer exchanged by first diluting with TBS approximately 3-fold and returning to original volume at least four times. Cross-flow was typically 180-200 mL/min for both Vivaflow 50 and 200.

The final product was filtered through Mustang E. The presence of endotoxin was evaluated after diluting 0.1 mL with 1.9 ml sterile fresh water. If endotoxin was greater than 1 EU/ml, reduction was conducted with Sterogene Etox gel. Formulated and sterile PEGylated NpPAL or AvPAL were sealed in vials and placed at −70° C. until ready for in vivo studies.

EXAMPLE 7

Effect of *Nostoc punctiforme* PAL (npPAL) and its PEGylated Form in PKU Affected Mice The objective of this study was to determine plasma phenylalanine (Phe) levels following subcutaneous administrations of npPAL or pegylated npPAL.

The effects of (1) a lysine mutant R91K PAL from *Rhodosporidium toruloides* and its pegylated form (1:3 PA::PEG) (PEG from Nippon Oil and Fat, NOF) at a dose of 3.0 IU/mL; (2) NpPAL and its pegylated form (1:3 PAL:PEG NOF) at doses ranging from 0.6 IU/mL to 3.0 IU/mL, and (3) vehicle were tested homozygous ENU2 mice (also known as BTBR$^{enu2}$) mice. R91K PAL was previously shown to have improved activity relative to wild-type *R. toruloides* PAL. R91K is located in the helix spanning Asp86 to Leu101, near the surface of the protein. All solutions had less than 1.0 EU/mL endotoxin and were stored at −75-80° C. The ENU2 or BTBR$^{enu2}$ mouse is homozygous mutant at the phenylalanine hydroxylase gene (PAH) locus resulting in an animal with severe hyperphenylalanemia. The high plasma phenylalanine (Phe) levels make this animal the appropriate model for evaluating the ability of phenylalanine ammonia lyase (PAL) to reduce plasma Phe.

Experimental Design

TABLE 3

Group Designations and Dose Levels

| Group # | N | Administered | Dose Level (IU/mouse) | Test Article Activity (IU/mL) | Dose Volume mL |
|---|---|---|---|---|---|
| 1 | 2 | R91K | 1.0 | 3.0 | 0.33 |
| 2 | 2 | R91K 1:3 PAL:PEG NOF | 1.0 | 3.0 | 0.33 |
| 3 | 5 | npPAL | 0.2 | 0.6 | 0.33 |
| 4 | 5 | npPAL | 0.4 | 1.2 | 0.33 |
| 5 | 5 | npPAL | 0.6 | 1.8 | 0.33 |
| 6 | 5 | npPAL | 1.0 | 3.0 | 0.33 |
| 7 | 5 | npPAL 1:3 PAL:PEG NOF | 0.2 | 0.46 | 0.43 |
| 8 | 5 | npPAL 1:3 PAL:PEG NOF | 0.4 | 0.92 | 0.43 |
| 9 | 5 | npPAL 1:3 PAL:PEG NOF | 0.6 | 1.38 | 0.43 |
| 10 | 5 | npPAL 1:3 PAL:PEG NOF | 1.0 | 2.30 | 0.43 |
| 11 | 2 | Vehicle | 0.0 | 0.0 | 0.43 |

The solutions were administered via subcutaneous bolus between the shoulder blades on day 1, in the right abdomen on day 4, and in the left abdomen on day 8. The solutions were administered using a 25-gauge needle and 1 or 3 cc syringe into the subcutaneous space. Each animal received 0.2, 0.4, 0.6 or 1.0 IU of test article in the dose volumes described in the table above. The animals were lightly anesthetized by inhalation of halothane (1-3% mg/kg) and also restrained by hand. Dose administration was performed at approximately the same time on each dose administration day.

Animals were observed daily for morbidity, mortality and general health. In particular, the injection site was observed for signs of redness or edema. Body Weights were measured and recorded on Days −3, 8 and 12 and used as a clinical parameter but not used to determine dose volume. Blood collections (P-plasma, S-serum) were performed on Day −3 (P,S), Day 2 (P), Day 4 Pre-dose (P), Day 5 (P), Day 8 Pre-dose (P,S), Day 9 (P,S), Day 12 (P), and Day 23 (S). Approximately 50-100 uL of whole blood was collected at each time point (for 25-50 uL of plasma or serum). Blood was collected from the tail vein. Plasma or serum was collected as indicated in the schedule above. The tail vein was punctured and the blood droplets were collected using RAM Scientific Green-Top Capillary Blood Collection Tubes (#07 7250). For serum collection, blood droplets were collected into a tube with no additives. Plasma/serum were harvested and transferred into a storage tube to be stored at −20° C. (plasma) or −80° C. (serum).

Results

Figure 5A:
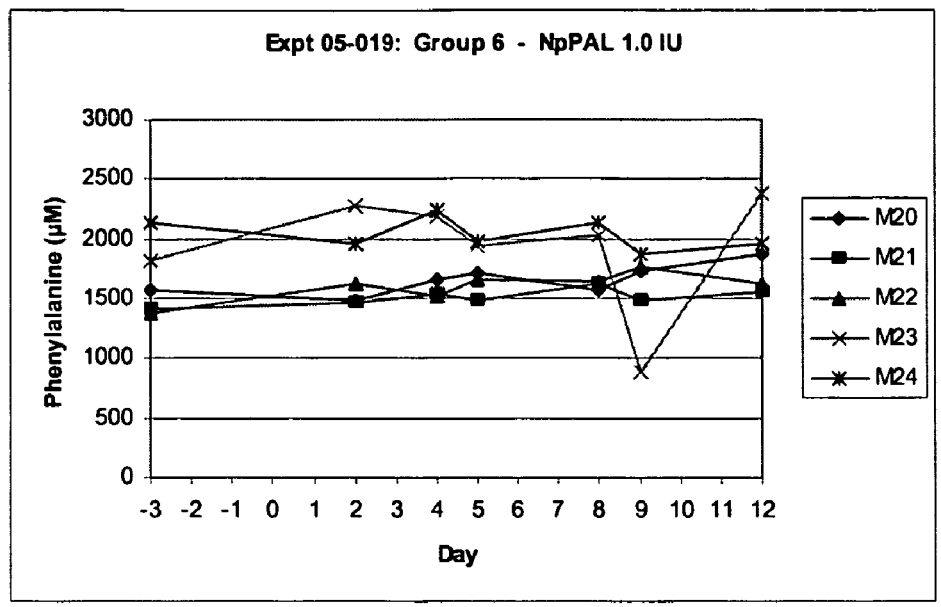
FIG. 5. Effect of (A) non-pegylated NpPAL (1.0 IU/mL) and (B) pegylated NpPAL 1:3 PAL:PEG (Nippon Fat and Oil) (1.0 IU/mL) on phenylalanine levels (uM) over a 12-day period.
Figure 5B:
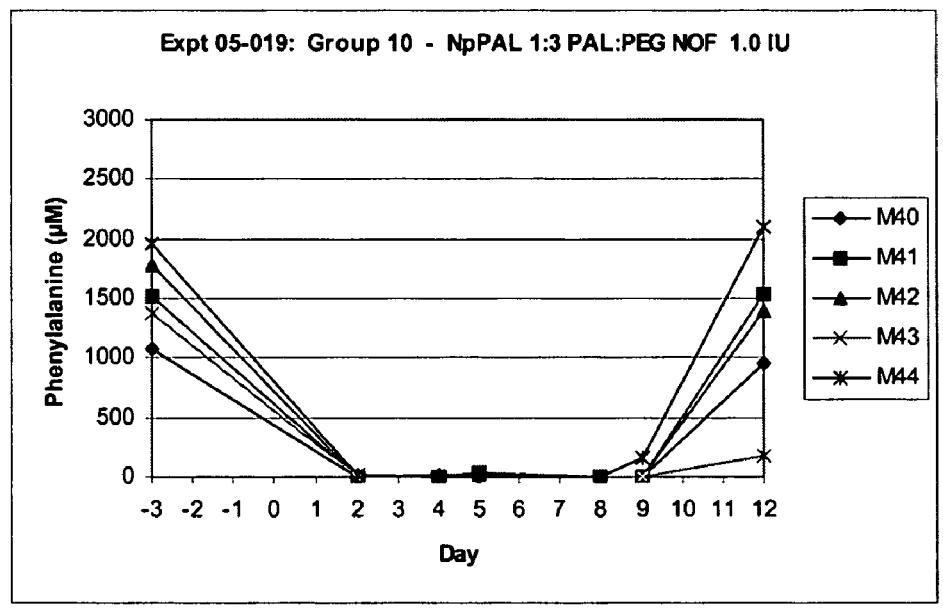

The results for NpPAL short-term dosing studies demonstrate the efficacy of the PEGylated enzymes in lowering excessive phenylalanine levels. Notably, unPEGylated NpPAL did not lower phenylalanine levels after any injection, even before there could be any immunogenic response. Therefore, PEGylation is an absolute requirement for NpPAL to be a potential treatment for PKU (FIG. 5).

EXAMPLE 8

Effect of *Anabaena variabilis* PAL (avPAL) and its Pegylated Form in PKU Affected Mice The objective of this study was to determine plasma phenylalanine (Phe) levels following subcutaneous administrations of avPAL or pegylated avPAL.

The effects of (1) a lysine mutant R91K PAL from *Rhodosporidium toruloides* in its pegylated form (1:3 PAL::PEG) (PEG from Nippon Oil and Fat, NOF) at a dose of 3.0 IU/mL; (2) avPAL and its pegylated form (1:3 PAL:PEG NOF) at doses of 0.6 IU/mL and 3.0 IU/mL, and (3) vehicle were tested homozygous ENU2 mice (also known as BTBR$^{enu2}$) mice. R91K PAL was previously shown to have improved activity relative to wild-type *R. toruloides* PAL. R91K is located in the helix spanning Asp86 to Leu101, near the surface of the protein. All solutions had less than 1.0 EU/mL endotoxin and were stored at −75-80° C. The ENU2 or BTBR$^{enu2}$ mouse is homozygous mutant at the phenylalanine hydroxylase gene (PAH) locus resulting in an animal with severe hyperphenylalanemia. The high plasma phenylalanine (Phe) levels make this animal the appropriate model for evaluating the ability of phenylalanine ammonia lyase (PAL) to reduce plasma Phe.

Experimental Design

TABLE 4

Group Designations and Dose levels

| Group # | N | Administered | Dose Level (IU/mouse) | Test Article Activity (IU/mL) | Dose Volume (mL) | Route | Dose Frequency |
|---|---|---|---|---|---|---|---|
| 1 | 3 | Vehicle | 0 | 0 | 0.33 | SC | Days 1, 4, 8 |
| 2 | 5 | avPAL | 0.2 | 0.6 | 0.33 | | |
| 3 | 5 | avPAL | 1.0 | 3.0 | 0.33 | | |
| 4 | 5 | avPAL PEG | 0.2 | 0.6 | 0.33 | | |
| 5 | 6 | avPAL PEG | 1.0 | 3.0 | 0.33 | | |
| 6 | 5 | R91K PEG | 1.0 | 3.0 | 0.33 | | |

The solutions were administered via subcutaneous bolus in the animal's rear back on days 1, 4, and 8. The solutions were administered using a 25-gauge needle and 1 or 3 cc syringe into the subcutaneous space. Each animal received 0.2, 0.4, 0.6 or 1.0 IU of test article in the dose volumes described in the table above. The animals were lightly anesthetized by inhalation of halothane (1-3% mg/kg) and also restrained by hand. Dose administration was performed at approximately the same time on each dose administration day.

Animals were observed daily for morbidity, mortality and general health. In particular, the injection site was observed for signs of redness or edema. Body Weights were measured and recorded on Days −3, 8 and 12 and used as a clinical parameter but not used to determine dose volume. Blood collections (P-plasma, S-serum) were performed on Day −3 (P,S), Day 2 (P), Day 4 Pre-dose (P), Day 5 (P), Day 8 Pre-dose (P,S), Day 9 (P,S), Day 12 (P), and Day 22 (S). Approximately 50-100 uL of whole blood was collected at each time point (for 25-50 uL of plasma or serum). Blood was collected from the tail vein. Plasma or serum was collected as indicated in the schedule above. The tail vein was punctured and the blood droplets were collected using RAM Scientific Green-Top Capillary Blood Collection Tubes (#07 7250). For serum collection, blood droplets were collected into a tube with no additives. Plasma/serum were harvested and transferred into a storage tube to be stored at −20° C. (plasma) or −80° C. (serum).

Results

Figure 6A:
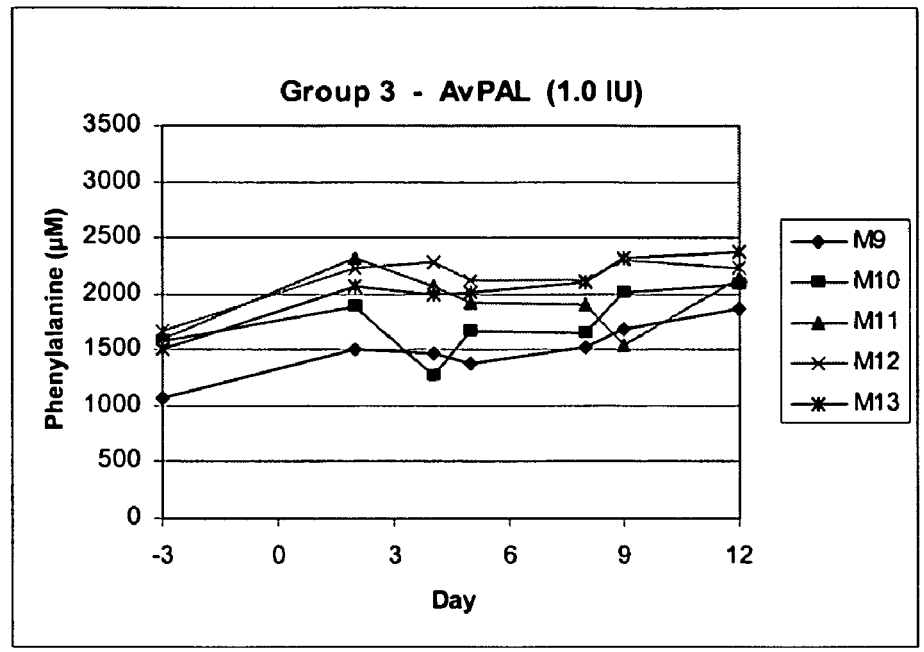
FIG. 6. Effect of (A) non-pegylated AvPAL (1.0 IU/mL) and (B) pegylated AvPAL 1:3 PAL:PEG (Nippon Fat and Oil) (1.0 IU/mL) on phenylalanine levels (uM) over a 12-day period.
Figure 6B:
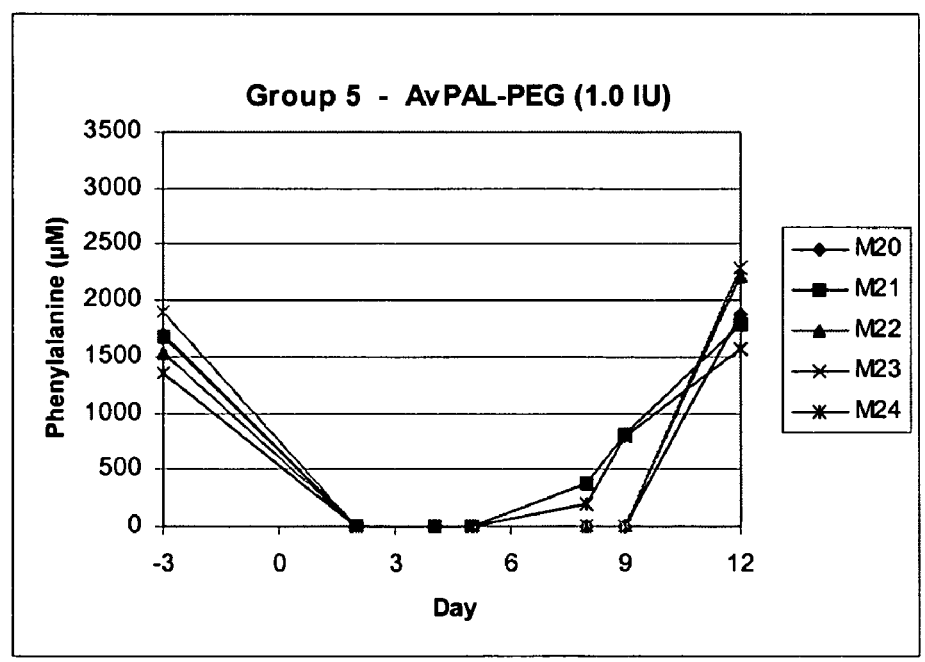

The results for AvPAL short-term dosing studies demonstrate the efficacy of the PEGylated enzymes in lowering excessive phenylalanine levels. Notably, unPEGylated AvPAL did not lower phenylalanine levels after any injection, even before there could be any immunogenic response. Therefore, PEGylation was shown to be an absolute requirement for AvPAL to be a potential treatment for PKU (FIG. 6).

EXAMPLE 9

Chronic (90 day) Tolerance Study of UnPEGylated and PEGylated R91K PAL and PEGylated npPAL in PKU Affected Mice The objective of this study was to evaluate the pharmacodynamic parameters and immunogenicity effects of chronic (90 day) dosing with pegylated and unpegylated R91K PAL and pegylated npPAL in ENU/2 mice, a disease model of phenylketonuria.

Two batches of each test article (R91K and its PEGylated form R91KPAL: PEG 1:3, npPAL and its PEGylated form npPAL:PEG 1:3 NOF, and vehicle Tris HCl) were produced, one used for the first half of the study and the second for the second half of the study. Test solutions were stored at −70° C. to −80° C. A total of 55 (n=3-7 per dose group) homozygous ENU2 mice (aka BTBR$^{enu2}$) were used, and under no circumstances were non-naïve (mice previously injected with PAL) animals used.

Experimental Design

TABLE 5

Group Designations and Dose Levels

| Group Number | Group Descriptors | Administered | Number of Doses | N |
|---|---|---|---|---|
| 1 | Vehicle control, s.i.d. | Tris NaCl | 90 | 3 |
| 2 | b.i.w. [a] | R91K | 26 | 3 |
| 3 | b.i.w. post week 3 [b] | R91K | 22 | 3 |
| 4 | Escalating Dose, s.i.d. | R91K | 90 | 7 |
| 5 | Decreasing Dose, s.i.d | R91K | 90 | 7 |
| 6 | b.i.w. [a] | R91K 1:3 NOF | 26 | 6 |
| 7 | b.i.w. post week 3 [b] | R91K 1:3 NOF | 22 | 6 |
| 8 | Escalating Dose, s.i.d. | R91K 1:3 NOF | 90 | 7 |
| 9 | Decreasing Dose, s.i.d | R91K 1:3 NOF | 90 | 7 |
| 10 | Bacterial PAL, s.i.w. [c] | npPAL 1:3 NOF | 13 | 6 | b.i.w.: twice per week
s.i.d.: once per day
s.i.w.: once per week
[a] Dose day 1 and 4 on a 7 day schedule (example, every Monday and Thursday)
[b] Groups 3 and 7 will be dosed on day 1 and 8, and starting on day 22 will follow the same 7 day schedule as groups 2 and 6.
[c] Dose day 1 on a 7 day schedule (example, every Monday)

TABLE 6

Dose Levels

| Group Numbers | Group Descriptors | Dose Days 1-14 | 15-28 | 29-42 | 43-56 | 57-90 |
|---|---|---|---|---|---|---|
| | | Dose level in IU/mouse/day | | | | |
| 1 | Vehicle control | 0 | 0 | 0 | 0 | 0 |
| 2, 3, 6 and 7 | Static dose, b.i.w. | 1.0 | 1.0 | 1.0 | 1.0 | 1.0 |
| 4 and 8 | Escalating Dose, s.i.d. | 0.2 | 0.4 | 0.6 | 0.8 | 1.0 |
| 5 and 9 | Decreasing Dose, s.i.d. | 3.0 | 2.0 | 1.0 | 0.8 | 0.6 |
| 10 | Bacterial PAL, s.i.w. | 1.0 | 1.0 | 1.0 | 1.0 | 1.0 |

Dose administration was performed once daily for groups 1, 4, 5, 8 and 9. Groups 2 and 6 (b.i.w.) were dosed twice per week on days 1 and 4, e.g., every Monday and Thursday.

Groups 3 and 7 (b.i.w. post week 3) were dosed on days 1 and 8 and then again on day 22, after which the schedule matched that of groups 2 and 6 (every Monday and Thursday). Group 10 was dosed once weekly. The test solutions were administered by subcutaneous injection (bolus) using a 25 or 26-gauge needle and a 1 cc syringe into the subcutaneous space between the shoulder blades. Each animal received a predetermined dose volume calculated using the Test solution activity (IU/mL) and the dose level (IU/mouse). Dose administration was performed at approximately the same time on each dose administration day.

Animals were observed daily for morbidity, mortality and general health. In particular, the injection site was observed for signs of redness or edema. Body Weights were measured and recorded once weekly, (day −3, 5, 12, . . . , e.g. every Friday) and at study termination. If there was a death or unscheduled termination due to moribund state, body weight was recorded at that time. Approximately 100 µL of whole blood were collected at each time point (for 25 µL of plasma and 25 µL of serum). Blood was collected via tail vein puncture from conscious animals. The blood droplets for plasma were collected using RAM Scientific Green-Top Capillary Blood Collection Tubes (#07 7250). For serum collection, blood was collected into a tube with no additives. Blood samples were stored on wet ice for no more than 2 hours before separation by centrifugation into plasma/serum and stored at −70 to −80° C. until assessment in assays. Blood was collected for plasma and serum for the determination of both phenylalanine and antibody titers on the following days: −3 (pre-study start), 9, 17, 24, 31, 38, 45, 52, 59, 66, 73, 80, 87 and 91. On day 89, blood and plasma was also be collected from Group 1, 5, 9 and 10 animals. Single timepoints each week may not be providing an accurate view of blood phe response to dosing. Additional timepoints showed whether or not phe levels are varying between doses. The day 9 sample was of vital importance to study integrity since it marks the time when the PD effect was lost in all dosing regimens attempted to date. A final 100 uL blood sample was collected.

Results

Figure 7:
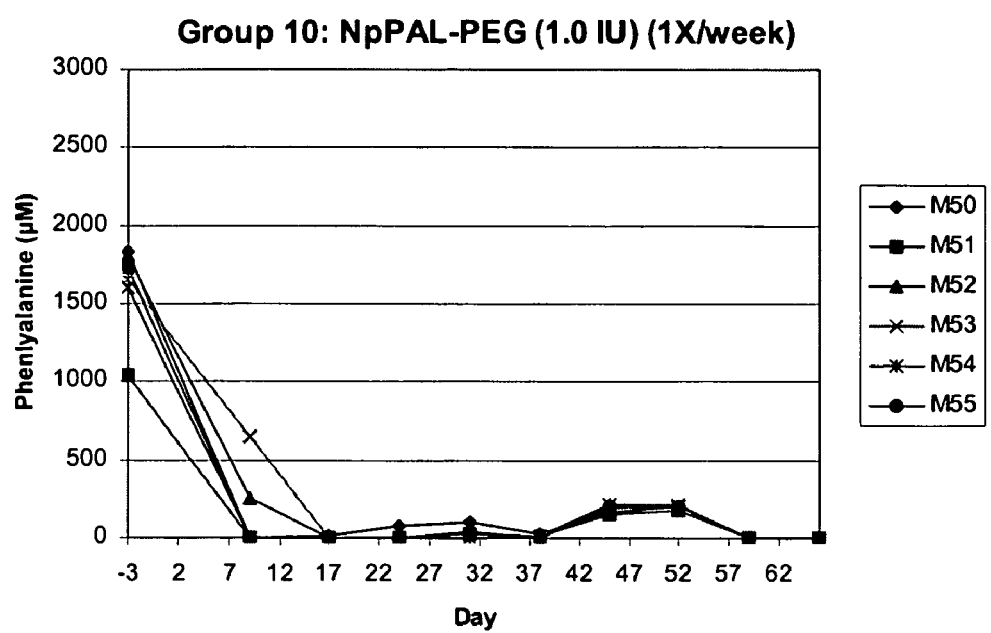
FIG. 7. Effect of pegylated NpPAL 1:3 PAL:PEG (Nippon Fat and Oil) (1.0 IU/mL) on phenylalanine levels (uM) in a 90-day chronic tolerance study.

The long-term dosing study shown in FIG. 7 shows continued efficacy after numerous weekly injections over a ten-week period (with NpPAL-PEG).

EXAMPLE 10

Clinical Evaluation with Prokaryotic PAL Compositions

The following example provides guidance on the parameters to be used for the clinical evaluation of compositions comprising prokaryotic PAL or biologically active variants, mutants, and fragments thereof ("PAL") in the therapeutic methods of the present invention. As discussed herein throughout, PAL will be used in the treatment of HPA including HPA, mild phenylketonuria (PKU) and classic PKU. Clinical trials will be conducted which will provide an assessment of oral or subcutaneous doses of PAL for safety, pharmacokinetics, and initial response of both surrogate and defined clinical endpoints. The trial will be conducted for a minimum, but not necessarily limited to, 24 weeks to collect sufficient safety information for 100 evaluable patients. The initial dose for the trials will vary from about 0.001 to about 1.0 mg/kg/week. In the event that this dose does not produce a reduction in excess plasma phenylalanine (Phe) levels in a patient, or produce a significant direct clinical benefit measured as an ability to increase daily oral Phe intake without increases in plasma Phe levels, the dose should be increased as necessary, and maintained for an additional minimal period of, but necessarily limited to, 24 weeks to establish safety and to evaluate further efficacy.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of PAL in blood. It is anticipated that these measures will help relate dose to clinical response.

Methods

Patients who have elevated levels of plasma Phe will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Diagnosis and Inclusion/Exclusion Criteria

The patient may be male or female, with a documented diagnosis of HPA or mild PKU confirmed by genetic testing and evidence of elevated Phe levels in blood. The study will include HPA or PKU patients who do not accurately follow dietary control. Female patients of childbearing potential must have a negative pregnancy test (urine β-hCG) just prior to each dosing and must be advised to use a medically accepted method of contraception throughout the study. A patient will be excluded from this study if the patient is pregnant or lactating; has received an investigational drug within 30 days prior to study enrollment; or has a medical condition, serious intercurrent illness, or other extenuating circumstance that may significantly decrease study compliance.

Dietary Intervention

Following the initial randomization and two-week treatment period, all study participants will undergo dietary counseling and will follow a standard Phe-restricted diet complemented with Phe-specific medical foods for a total of four to six weeks. Diets will be managed at home and dietary intake will be recorded in daily logs. Analyses of the intakes of nutrients and medical foods and the percent of Recommended Dietary Intakes (RDI) will be compared among the treatment groups.

PAL Safety

PAL therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

We claim:

1. A wild-type *Anabaena variabilis* phenylalanine ammonia lyase comprising a polyethylene glycol.

2. The phenylalanine ammonia lyase of claim 1 having a phenylalanine ammonia lyase:polyethylene glycol ratio of 1:3.

3. A pharmaceutical composition comprising the phenylalanine ammonia lyase of claim 1 and a pharmaceutically acceptable carrier.

4. A wild-type *Nostoc punctiforme* phenylalanine ammonia lyase comprising a polyethylene glycol.

5. The phenylalanine ammonia lyase of claim 4 having a phenylalanine ammonia lyase:polyethylene glycol ratio of 1:3.

6. A pharmaceutical composition comprising the phenylalanine ammonia lyase of claim 4 and a pharmaceutically acceptable carrier.

* * * * *

SEQUENCE LISTING

<160> NUMBER OF SEQ ID NOS: 8

<210> SEQ ID NO 1
<211> LENGTH: 1710
<212> TYPE: DNA
<213> ORGANISM: Nostoc punctiforme
<220> FEATURE:
<221> NAME/KEY: CDS
<222> LOCATION: (1)..(1710)

<400> SEQUENCE: 1

| | | | | | | | | | | | | | | | | |
|---|---|---|---|---|---|---|---|---|---|---|---|---|---|---|---|---|
| atg | aat | ata | aca | tct | cta | caa | cag | aac | ata | acg | cgt | tct | tgg | caa | ata | 48 |
| Met | Asn | Ile | Thr | Ser | Leu | Gln | Gln | Asn | Ile | Thr | Arg | Ser | Trp | Gln | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cct | ttc | act | aat | agt | tca | gat | tca | atc | gta | act | gta | ggc | gat | cgc | aat | 96 |
| Pro | Phe | Thr | Asn | Ser | Ser | Asp | Ser | Ile | Val | Thr | Val | Gly | Asp | Arg | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | aca | atc | gac | gag | gtt | gta | aat | gtt | gct | cgt | cat | gga | aca | cag | gtg | 144 |
| Leu | Thr | Ile | Asp | Glu | Val | Val | Asn | Val | Ala | Arg | His | Gly | Thr | Gln | Val | |
| | | | 35 | | | | | 40 | | | | | 45 | | | |

| | | | | | | | | | | | | | | | | |
|---|---|---|---|---|---|---|---|---|---|---|---|---|---|---|---|---|
| cgc | tta | act | gat | aat | gca | gat | gtc | att | cgg | ggt | gtt | caa | gca | tct | tgt | 192 |
| Arg | Leu | Thr | Asp | Asn | Ala | Asp | Val | Ile | Arg | Gly | Val | Gln | Ala | Ser | Cys | |
| | 50 | | | | | 55 | | | | | 60 | | | | | |

| | | | | | | | | | | | | | | | | |
|---|---|---|---|---|---|---|---|---|---|---|---|---|---|---|---|---|
| gat | tac | att | aac | aat | gca | gtc | gaa | aca | gca | cag | cca | att | tac | ggg | gtg | 240 |
| Asp | Tyr | Ile | Asn | Asn | Ala | Val | Glu | Thr | Ala | Gln | Pro | Ile | Tyr | Gly | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aca | tct | ggc | ttt | ggc | ggt | atg | gca | gat | gtt | gtc | atc | tct | cgc | gaa | caa | 288 |
| Thr | Ser | Gly | Phe | Gly | Gly | Met | Ala | Asp | Val | Val | Ile | Ser | Arg | Glu | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | gcg | gaa | ctt | cag | act | aat | tta | att | tgg | ttt | ctg | aaa | tcc | ggc | gca | 336 |
| Ala | Ala | Glu | Leu | Gln | Thr | Asn | Leu | Ile | Trp | Phe | Leu | Lys | Ser | Gly | Ala | |
| | | | | 100 | | | | | 105 | | | | | 110 | | |

| | | | | | | | | | | | | | | | | |
|---|---|---|---|---|---|---|---|---|---|---|---|---|---|---|---|---|
| gga | aac | aaa | tta | tcg | tta | gca | gac | gtg | cgt | gca | gct | atg | ctc | tta | cgt | 384 |
| Gly | Asn | Lys | Leu | Ser | Leu | Ala | Asp | Val | Arg | Ala | Ala | Met | Leu | Leu | Arg | |
| | | | 115 | | | | | 120 | | | | | 125 | | | |

| | | | | | | | | | | | | | | | | |
|---|---|---|---|---|---|---|---|---|---|---|---|---|---|---|---|---|
| gca | aat | tca | cat | ttg | tat | ggt | gcg | tct | ggt | ata | cga | ctc | gaa | ctt | att | 432 |
| Ala | Asn | Ser | His | Leu | Tyr | Gly | Ala | Ser | Gly | Ile | Arg | Leu | Glu | Leu | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| cag | cgg | att | gaa | act | ttc | ctc | aac | gct | ggc | gtg | aca | ccc | cat | gtc | tat | 480 |
| Gln | Arg | Ile | Glu | Thr | Phe | Leu | Asn | Ala | Gly | Val | Thr | Pro | His | Val | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gag | ttt | ggc | tct | atc | ggt | gct | agc | ggc | gat | ttg | gtg | cca | tta | tcc | tac | 528 |
| Glu | Phe | Gly | Ser | Ile | Gly | Ala | Ser | Gly | Asp | Leu | Val | Pro | Leu | Ser | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| att | act | ggg | gca | cta | atc | ggt | cta | gat | cct | agc | ttt | aca | gtt | gac | ttc | 576 |
| Ile | Thr | Gly | Ala | Leu | Ile | Gly | Leu | Asp | Pro | Ser | Phe | Thr | Val | Asp | Phe | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | ggt | aaa | gaa | atg | gat | gcc | gtt | aca | gcc | ttg | tct | cgt | ttg | ggt | ttg | 624 |
| Asp | Gly | Lys | Glu | Met | Asp | Ala | Val | Thr | Ala | Leu | Ser | Arg | Leu | Gly | Leu | |
| | | | 195 | | | | | 200 | | | | | 205 | | | |

| | | | | | | | | | | | | | | | | |
|---|---|---|---|---|---|---|---|---|---|---|---|---|---|---|---|---|
| cca | aag | ttg | caa | ttg | caa | ccg | aaa | gaa | ggt | tta | gca | atg | atg | aat | ggc | 672 |
| Pro | Lys | Leu | Gln | Leu | Gln | Pro | Lys | Glu | Gly | Leu | Ala | Met | Met | Asn | Gly | |
| | | 210 | | | | | 215 | | | | | 220 | | | | |

| | | | | | | | | | | | | | | | | |
|---|---|---|---|---|---|---|---|---|---|---|---|---|---|---|---|---|
| acc | tca | gtc | atg | aca | ggt | att | gca | gct | aac | tgt | gtg | tac | gat | gcg | aaa | 720 |
| Thr | Ser | Val | Met | Thr | Gly | Ile | Ala | Ala | Asn | Cys | Val | Tyr | Asp | Ala | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtt | ttg | ctc | gct | ctg | aca | atg | ggt | gta | cac | gcc | tta | gcc | atc | caa | ggt | 768 |
| Val | Leu | Leu | Ala | Leu | Thr | Met | Gly | Val | His | Ala | Leu | Ala | Ile | Gln | Gly | |
| | | | | 245 | | | | | 250 | | | | | 255 | | |

```
tta tac gga acg aat caa tct ttc cac ccg ttt att cat cag tgc aag      816
Leu Tyr Gly Thr Asn Gln Ser Phe His Pro Phe Ile His Gln Cys Lys
        260                 265                 270 cca cat ccc ggt caa cta tgg aca gca gat caa atg ttt tct ctg ctg      864
Pro His Pro Gly Gln Leu Trp Thr Ala Asp Gln Met Phe Ser Leu Leu
            275                 280                 285 aaa gat tca tct tta gtt cgt gaa gag ttg gat ggt aaa cac gaa tac      912
Lys Asp Ser Ser Leu Val Arg Glu Glu Leu Asp Gly Lys His Glu Tyr
290                 295                 300 cgt ggt aaa gat ctg ata cag gat cgt tat tct ctc cgc tgt ctg gca      960
Arg Gly Lys Asp Leu Ile Gln Asp Arg Tyr Ser Leu Arg Cys Leu Ala
305                 310                 315                 320 cag ttc ata ggg cca atc gtt gat ggg gta tca gag att acc aag caa     1008
Gln Phe Ile Gly Pro Ile Val Asp Gly Val Ser Glu Ile Thr Lys Gln
                325                 330                 335 atc gag gta gaa atg aac tca gtc acc gat aac cca ttg att gat gtc     1056
Ile Glu Val Glu Met Asn Ser Val Thr Asp Asn Pro Leu Ile Asp Val
            340                 345                 350 gag aac caa gtt agt tat cac ggc ggc aat ttt ctc gga cag tat gtg     1104
Glu Asn Gln Val Ser Tyr His Gly Gly Asn Phe Leu Gly Gln Tyr Val
        355                 360                 365 ggt gtg aca atg gat cgc cta cgt tat tac ata ggg cta ttg gcc aaa     1152
Gly Val Thr Met Asp Arg Leu Arg Tyr Tyr Ile Gly Leu Leu Ala Lys
370                 375                 380 cac atc gat gtg cag att gca ctt ctt gtc tcg cca gag ttt agc aac     1200
His Ile Asp Val Gln Ile Ala Leu Leu Val Ser Pro Glu Phe Ser Asn
385                 390                 395                 400 ggc tta cca ccc tct tta gtt ggt aat agc gat cgc aaa gtt aat atg     1248
Gly Leu Pro Pro Ser Leu Val Gly Asn Ser Asp Arg Lys Val Asn Met
                405                 410                 415 gga ctc aaa ggt ttg caa atc agt gga aac tcg att atg cca ctg ttg     1296
Gly Leu Lys Gly Leu Gln Ile Ser Gly Asn Ser Ile Met Pro Leu Leu
            420                 425                 430 agc ttc tat gga aat tcc cta gcc gat cgc ttt cct acc cac gcc gag     1344
Ser Phe Tyr Gly Asn Ser Leu Ala Asp Arg Phe Pro Thr His Ala Glu
        435                 440                 445 caa ttt aat caa aat att aac agc caa ggc tat att tcc gca aat ttg     1392
Gln Phe Asn Gln Asn Ile Asn Ser Gln Gly Tyr Ile Ser Ala Asn Leu
    450                 455                 460 aca cgt cgt tcc gta gac ata ttt cag aat tat atg gcg atc gcg ttg     1440
Thr Arg Arg Ser Val Asp Ile Phe Gln Asn Tyr Met Ala Ile Ala Leu
465                 470                 475                 480 atg ttt gga gtt caa gct gtt gac ctc cgc aca tat aag atg aaa ggt     1488
Met Phe Gly Val Gln Ala Val Asp Leu Arg Thr Tyr Lys Met Lys Gly
                485                 490                 495 cat tat gat gca cgt aca tgc ctc tca ccc aat act gtg cag tta tac     1536
His Tyr Asp Ala Arg Thr Cys Leu Ser Pro Asn Thr Val Gln Leu Tyr
            500                 505                 510 aca gca gtc tgc gag gta gtt gga aag cca cta acg tct gtg cgt cca     1584
Thr Ala Val Cys Glu Val Val Gly Lys Pro Leu Thr Ser Val Arg Pro
        515                 520                 525 tac att tgg aac gac aac gag caa tgt tta gat gag cat att gcc cgg     1632
Tyr Ile Trp Asn Asp Asn Glu Gln Cys Leu Asp Glu His Ile Ala Arg
    530                 535                 540 att tca gct gat atc gct ggt ggt ggt tta att gtg caa gca gtt gag     1680
Ile Ser Ala Asp Ile Ala Gly Gly Gly Leu Ile Val Gln Ala Val Glu
545                 550                 555                 560 cat att ttt tcg agc tta aag tca acg taa                             1710
His Ile Phe Ser Ser Leu Lys Ser Thr
                565
```

<210> SEQ ID NO 2
<211> LENGTH: 569
<212> TYPE: PRT
<213> ORGANISM: Nostoc punctiforme

<400> SEQUENCE: 2

```
Met Asn Ile Thr Ser Leu Gln Gln Asn Ile Thr Arg Ser Trp Gln Ile
1               5                   10                  15

Pro Phe Thr Asn Ser Ser Asp Ser Ile Val Thr Val Gly Asp Arg Asn
            20                  25                  30

Leu Thr Ile Asp Glu Val Val Asn Val Ala Arg His Gly Thr Gln Val
        35                  40                  45

Arg Leu Thr Asp Asn Ala Asp Val Ile Arg Gly Val Gln Ala Ser Cys
    50                  55                  60

Asp Tyr Ile Asn Asn Ala Val Glu Thr Ala Gln Pro Ile Tyr Gly Val
65                  70                  75                  80

Thr Ser Gly Phe Gly Gly Met Ala Asp Val Val Ile Ser Arg Glu Gln
                85                  90                  95

Ala Ala Glu Leu Gln Thr Asn Leu Ile Trp Phe Leu Lys Ser Gly Ala
            100                 105                 110

Gly Asn Lys Leu Ser Leu Ala Asp Val Arg Ala Ala Met Leu Leu Arg
        115                 120                 125

Ala Asn Ser His Leu Tyr Gly Ala Ser Gly Ile Arg Leu Glu Leu Ile
    130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                165                 170                 175

Ile Thr Gly Ala Leu Ile Gly Leu Asp Pro Ser Phe Thr Val Asp Phe
            180                 185                 190

Asp Gly Lys Glu Met Asp Ala Val Thr Ala Leu Ser Arg Leu Gly Leu
        195                 200                 205

Pro Lys Leu Gln Leu Gln Pro Lys Glu Gly Leu Ala Met Met Asn Gly
    210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
                245                 250                 255

Leu Tyr Gly Thr Asn Gln Ser Phe His Pro Phe Ile His Gln Cys Lys
            260                 265                 270

Pro His Pro Gly Gln Leu Trp Thr Ala Asp Gln Met Phe Ser Leu Leu
        275                 280                 285

Lys Asp Ser Ser Leu Val Arg Glu Glu Leu Asp Gly Lys His Glu Tyr
    290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
                325                 330                 335

Ile Glu Val Glu Met Asn Ser Val Thr Asp Asn Pro Leu Ile Asp Val
            340                 345                 350

Glu Asn Gln Val Ser Tyr His Gly Gly Asn Phe Leu Gly Gln Tyr Val
        355                 360                 365

Gly Val Thr Met Asp Arg Leu Arg Tyr Tyr Ile Gly Leu Leu Ala Lys
```

-continued

```
                370                 375                 380
His Ile Asp Val Gln Ile Ala Leu Leu Val Ser Pro Glu Phe Ser Asn
385                 390                 395                 400

Gly Leu Pro Pro Ser Leu Val Gly Asn Ser Asp Arg Lys Val Asn Met
            405                 410                 415

Gly Leu Lys Gly Leu Gln Ile Ser Gly Asn Ser Ile Met Pro Leu Leu
        420                 425                 430

Ser Phe Tyr Gly Asn Ser Leu Ala Asp Arg Phe Pro Thr His Ala Glu
            435                 440                 445

Gln Phe Asn Gln Asn Ile Asn Ser Gln Gly Tyr Ile Ser Ala Asn Leu
        450                 455                 460

Thr Arg Arg Ser Val Asp Ile Phe Gln Asn Tyr Met Ala Ile Ala Leu
465                 470                 475                 480

Met Phe Gly Val Gln Ala Val Asp Leu Arg Thr Tyr Lys Met Lys Gly
            485                 490                 495

His Tyr Asp Ala Arg Thr Cys Leu Ser Pro Asn Thr Val Gln Leu Tyr
            500                 505                 510

Thr Ala Val Cys Glu Val Val Gly Lys Pro Leu Thr Ser Val Arg Pro
        515                 520                 525

Tyr Ile Trp Asn Asp Asn Glu Gln Cys Leu Asp Glu His Ile Ala Arg
            530                 535                 540

Ile Ser Ala Asp Ile Ala Gly Gly Gly Leu Ile Val Gln Ala Val Glu
545                 550                 555                 560

His Ile Phe Ser Ser Leu Lys Ser Thr
                565

<210> SEQ ID NO 3
<211> LENGTH: 1704
<212> TYPE: DNA
<213> ORGANISM: Anabaena variabilis
<220> FEATURE:
<221> NAME/KEY: CDS
<222> LOCATION: (1)..(1704)

<400> SEQUENCE: 3 atg aag aca cta tct caa gca caa agc aaa acc tca tct caa caa ttt      48
Met Lys Thr Leu Ser Gln Ala Gln Ser Lys Thr Ser Ser Gln Gln Phe
1               5                   10                  15 tct ttt act gga aat tct tct gcc aat gta att att ggt aat cag aaa      96
Ser Phe Thr Gly Asn Ser Ser Ala Asn Val Ile Ile Gly Asn Gln Lys
            20                  25                  30 ctc aca atc aat gat gtt gca agg gta gcg cgt aat ggc acc tta gtg     144
Leu Thr Ile Asn Asp Val Ala Arg Val Ala Arg Asn Gly Thr Leu Val
        35                  40                  45 tct tta acc aat aac act gat att ttg cag ggt att cag gca tct tgt     192
Ser Leu Thr Asn Asn Thr Asp Ile Leu Gln Gly Ile Gln Ala Ser Cys
    50                  55                  60 gat tac att aat aat gct gtt gaa tct ggg gaa cca att tat gga gtg     240
Asp Tyr Ile Asn Asn Ala Val Glu Ser Gly Glu Pro Ile Tyr Gly Val
65                  70                  75                  80 aca tct ggt ttt ggc ggt atg gcc aat gtt gcc ata tcc cgt gaa caa     288
Thr Ser Gly Phe Gly Gly Met Ala Asn Val Ala Ile Ser Arg Glu Gln
            85                  90                  95 gca tct gaa ctc caa acc aac tta gtt tgg ttc ctg aaa aca ggt gca     336
Ala Ser Glu Leu Gln Thr Asn Leu Val Trp Phe Leu Lys Thr Gly Ala
        100                 105                 110 ggg aac aaa tta ccc ttg gcg gat gtg cgc gca gct atg ctc ttg cgt     384
Gly Asn Lys Leu Pro Leu Ala Asp Val Arg Ala Ala Met Leu Leu Arg
```

```
                    115                 120                 125
gca aac tct cat atg cgc ggt gca tct ggc atc aga tta gaa ctt atc       432
Ala Asn Ser His Met Arg Gly Ala Ser Gly Ile Arg Leu Glu Leu Ile
    130                 135                 140 aag cgt atg gag att ttc ctt aac gct ggt gtc aca cca tat gtg tat       480
Lys Arg Met Glu Ile Phe Leu Asn Ala Gly Val Thr Pro Tyr Val Tyr
145                 150                 155                 160 gag ttt ggt tca att ggt gca agt ggt gat tta gtg cca cta tcc tac       528
Glu Phe Gly Ser Ile Gly Ala Ser Gly Asp Leu Val Pro Leu Ser Tyr
                165                 170                 175 att act ggt tca ctg ata ggc tta gat ccc agt ttt aag gtt gac ttc       576
Ile Thr Gly Ser Leu Ile Gly Leu Asp Pro Ser Phe Lys Val Asp Phe
            180                 185                 190 aac ggt aaa gaa atg gat gcg cca aca gct cta cgt caa ctg aat ttg       624
Asn Gly Lys Glu Met Asp Ala Pro Thr Ala Leu Arg Gln Leu Asn Leu
        195                 200                 205 tca ccc ttg aca ttg ttg ccg aag gaa ggc ttg gcg atg atg aac ggc       672
Ser Pro Leu Thr Leu Leu Pro Lys Glu Gly Leu Ala Met Met Asn Gly
    210                 215                 220 act tca gtc atg aca ggt att gca gca aac tgc gtc tac gat act caa       720
Thr Ser Val Met Thr Gly Ile Ala Ala Asn Cys Val Tyr Asp Thr Gln
225                 230                 235                 240 att tta act gcg atc gct atg ggc gtt cac gct cta gat atc caa gct       768
Ile Leu Thr Ala Ile Ala Met Gly Val His Ala Leu Asp Ile Gln Ala
                245                 250                 255 tta aac gga acc aat caa tca ttc cat cca ttt atc cat aat tcc aaa       816
Leu Asn Gly Thr Asn Gln Ser Phe His Pro Phe Ile His Asn Ser Lys
            260                 265                 270 cca cat cct ggt caa tta tgg gca gca gat cag atg att tct ttg tta       864
Pro His Pro Gly Gln Leu Trp Ala Ala Asp Gln Met Ile Ser Leu Leu
        275                 280                 285 gcc aat tcc cag tta gtt cgt gat gag tta gat ggt aaa cac gat tat       912
Ala Asn Ser Gln Leu Val Arg Asp Glu Leu Asp Gly Lys His Asp Tyr
    290                 295                 300 cgt gat cac gag ttg att caa gat cgt tac tca ctc cga tgc ctt ccc       960
Arg Asp His Glu Leu Ile Gln Asp Arg Tyr Ser Leu Arg Cys Leu Pro
305                 310                 315                 320 cag tat ttg ggg cca atc gtt gat gga att tcc cag att gcc aaa caa      1008
Gln Tyr Leu Gly Pro Ile Val Asp Gly Ile Ser Gln Ile Ala Lys Gln
                325                 330                 335 att gaa atc gaa atc aac tca gtc acc gat aac cca cta att gat gtt      1056
Ile Glu Ile Glu Ile Asn Ser Val Thr Asp Asn Pro Leu Ile Asp Val
            340                 345                 350 gat aac caa gct agc tat cat gga gga aat ttc ctc gga cag tac gtg      1104
Asp Asn Gln Ala Ser Tyr His Gly Gly Asn Phe Leu Gly Gln Tyr Val
        355                 360                 365 ggt atg gga atg gat cac ctg cgt tac tat att ggg tta ttg gct aaa      1152
Gly Met Gly Met Asp His Leu Arg Tyr Tyr Ile Gly Leu Leu Ala Lys
    370                 375                 380 cac cta gat gtg cag att gcc ctc ctc gcc tca cca gag ttt agc aat      1200
His Leu Asp Val Gln Ile Ala Leu Leu Ala Ser Pro Glu Phe Ser Asn
385                 390                 395                 400 gga cta cca cca tct tta tta ggc aac cga gaa cgt aaa gtc aat atg      1248
Gly Leu Pro Pro Ser Leu Leu Gly Asn Arg Glu Arg Lys Val Asn Met
                405                 410                 415 gga ctc aaa ggt ctg caa ata tgc ggt aac tca att atg cca ctg ttg      1296
Gly Leu Lys Gly Leu Gln Ile Cys Gly Asn Ser Ile Met Pro Leu Leu
            420                 425                 430 acc ttc tat gga aat ccc atc gcc gat cgc ttt cct acc cat gca gaa      1344
```

-continued

```
                Thr Phe Tyr Gly Asn Ser Ile Ala Asp Arg Phe Pro Thr His Ala Glu
                        435                 440                 445 caa ttt aat cag aac atc aac agt caa gga tac act tca gcg act cta         1392
Gln Phe Asn Gln Asn Ile Asn Ser Gln Gly Tyr Thr Ser Ala Thr Leu
    450                 455                 460 gcc cgc cgt tct gtg gat atc ttc cag aat tat gtg gcg atc gct ctg         1440
Ala Arg Arg Ser Val Asp Ile Phe Gln Asn Tyr Val Ala Ile Ala Leu
465                 470                 475                 480 atg ttt gga gtc caa gct gtt gac ctc cgc aca tat aaa aag act ggt         1488
Met Phe Gly Val Gln Ala Val Asp Leu Arg Thr Tyr Lys Lys Thr Gly
                485                 490                 495 cat tac gat gca cgc gcc tgt cta tca cct gca act gag cgc tta tat         1536
His Tyr Asp Ala Arg Ala Cys Leu Ser Pro Ala Thr Glu Arg Leu Tyr
            500                 505                 510 tca gca gtc cgc cac gta gtt gga caa aaa cca act tca gat cgc cca         1584
Ser Ala Val Arg His Val Val Gly Gln Lys Pro Thr Ser Asp Arg Pro
        515                 520                 525 tat att tgg aat gat aat gag caa gga ctg gat gag cat att gcc cgg         1632
Tyr Ile Trp Asn Asp Asn Glu Gln Gly Leu Asp Glu His Ile Ala Arg
    530                 535                 540 att tct gct gat atc gct gct ggt ggt gtg att gtg caa gca gtt caa         1680
Ile Ser Ala Asp Ile Ala Ala Gly Gly Val Ile Val Gln Ala Val Gln
545                 550                 555                 560 gat atc tta ccc tgc ttg cat taa                                         1704
Asp Ile Leu Pro Cys Leu His
                565
```

<210> SEQ ID NO 4
<211> LENGTH: 567
<212> TYPE: PRT
<213> ORGANISM: Anabaena variabilis

<400> SEQUENCE: 4

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190
```

Asn Gly Lys Glu Met Asp Ala Pro Thr Ala Leu Arg Gln Leu Asn Leu
        195                 200                 205

Ser Pro Leu Thr Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 5
<211> LENGTH: 569
<212> TYPE: PRT
<213> ORGANISM: Nostoc punctiforme

<400> SEQUENCE: 5

```
Met Asn Ile Thr Ser Leu Gln Gln Asn Ile Thr Arg Ser Trp Gln Ile
1               5                   10                  15

Pro Phe Thr Asn Ser Ser Asp Ser Ile Val Thr Val Gly Asp Arg Asn
                20                  25                  30

Leu Thr Ile Asp Glu Val Val Asn Val Ala Arg His Gly Thr Gln Val
            35                  40                  45

Arg Leu Thr Asp Asn Ala Asp Val Ile Arg Gly Val Gln Ala Ser Cys
    50                  55                  60

Asp Tyr Ile Asn Asn Ala Val Glu Thr Ala Gln Pro Ile Tyr Gly Val
65                  70                  75                  80

Thr Ser Gly Phe Gly Gly Met Ala Asp Val Val Ile Ser Arg Glu Gln
                85                  90                  95

Ala Ala Glu Leu Gln Thr Asn Leu Ile Trp Phe Leu Lys Ser Gly Ala
                100                 105                 110

Gly Asn Lys Leu Ser Leu Ala Asp Val Arg Ala Ala Met Leu Leu Arg
            115                 120                 125

Ala Asn Ser His Leu Tyr Gly Ala Ser Gly Ile Arg Leu Glu Leu Ile
    130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                165                 170                 175

Ile Thr Gly Ala Leu Ile Gly Leu Asp Pro Ser Phe Thr Val Asp Phe
            180                 185                 190

Asp Gly Lys Glu Met Asp Ala Val Thr Ala Leu Ser Arg Leu Gly Leu
    195                 200                 205

Pro Lys Leu Gln Leu Gln Pro Lys Glu Gly Leu Ala Met Met Asn Gly
210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
                245                 250                 255

Leu Tyr Gly Thr Asn Gln Ser Phe His Pro Phe Ile His Gln Cys Lys
            260                 265                 270

Pro His Pro Gly Gln Leu Trp Thr Ala Asp Gln Met Phe Ser Leu Leu
    275                 280                 285

Lys Asp Ser Ser Leu Val Arg Glu Glu Leu Asp Gly Lys His Glu Tyr
290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
                325                 330                 335

Ile Glu Val Glu Met Asn Ser Val Thr Asp Asn Pro Leu Ile Asp Val
            340                 345                 350

Glu Asn Gln Val Ser Tyr His Gly Gly Asn Phe Leu Gly Gln Tyr Val
    355                 360                 365

Gly Val Thr Met Asp Arg Leu Arg Tyr Tyr Ile Gly Leu Leu Ala Lys
370                 375                 380

His Ile Asp Val Gln Ile Ala Leu Leu Val Ser Pro Glu Phe Ser Asn
385                 390                 395                 400

Gly Leu Pro Pro Ser Leu Val Gly Asn Ser Asp Arg Lys Val Asn Met
                405                 410                 415
```

-continued

Gly Leu Lys Gly Leu Gln Ile Ser Gly Asn Ser Ile Met Pro Leu Leu
                420                 425                 430

Ser Phe Tyr Gly Asn Ser Leu Ala Asp Arg Phe Pro Thr His Ala Glu
                435                 440                 445

Gln Phe Asn Gln Asn Ile Asn Ser Gln Gly Tyr Ile Ser Ala Asn Leu
                450                 455                 460

Thr Arg Arg Ser Val Asp Ile Phe Gln Asn Tyr Met Ala Ile Ala Leu
465                 470                 475                 480

Met Phe Gly Val Gln Ala Val Asp Leu Arg Thr Tyr Lys Met Lys Gly
                485                 490                 495

His Tyr Asp Ala Arg Thr Cys Leu Ser Pro Asn Thr Val Gln Leu Tyr
                500                 505                 510

Thr Ala Val Cys Glu Val Val Gly Lys Pro Leu Thr Ser Val Arg Pro
                515                 520                 525

Tyr Ile Trp Asn Asp Asn Glu Gln Cys Leu Asp Glu His Ile Ala Arg
                530                 535                 540

Ile Ser Ala Asp Ile Ala Gly Gly Leu Ile Val Gln Ala Val Glu
545                 550                 555                 560

His Ile Phe Ser Ser Leu Lys Ser Thr
                565

<210> SEQ ID NO 6
<211> LENGTH: 567
<212> TYPE: PRT
<213> ORGANISM: Anabaena variabilis

<400> SEQUENCE: 6

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
                35                  40                  45

Ser Leu Thr Asn Asn Thr Asp Ile Leu Gln Gly Ile Gln Ala Ser Cys
                50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
                115                 120                 125

Ala Asn Ser His Met Arg Gly Ala Ser Gly Ile Arg Leu Glu Leu Ile
                130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
                195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
            245                 250                 255

Leu Asn Gly Thr Asn Gln Ser Phe His Pro Phe Ile His Asn Ser Lys
        260                 265                 270

Pro His Pro Gly Gln Leu Trp Ala Ala Asp Gln Met Ile Ser Leu Leu
    275                 280                 285

Ala Asn Ser Gln Leu Val Arg Asp Glu Leu Asp Gly Lys His Asp Tyr
290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 7
<211> LENGTH: 523
<212> TYPE: PRT
<213> ORGANISM: Streptomyces maritimus

<400> SEQUENCE: 7

Met Thr Phe Val Ile Glu Leu Asp Met Asn Val Thr Leu Asp Gln Leu
1               5                   10                  15

Glu Asp Ala Ala Arg Gln Arg Thr Pro Val Glu Leu Ser Ala Pro Val

-continued

```
               20                  25                  30
Arg Ser Arg Val Arg Ala Ser Arg Asp Val Leu Val Lys Phe Val Gln
            35                  40                  45
Asp Glu Arg Val Ile Tyr Gly Val Asn Thr Ser Met Gly Gly Phe Val
        50                  55                  60
Asp His Leu Val Pro Val Ser Gln Ala Arg Gln Leu Leu Asn Ala Gly
65                  70                  75                  80
Ile Val Pro Cys Ile Pro Glu Lys Gly Ser Leu Gly Thr Ser Gly Asp
                85                  90                  95
Leu Gly Pro Leu Ala Ala Ile Ala Leu Val Cys Ala Gly Gln Trp Lys
            100                 105                 110
Ala Arg Tyr Asn Gly Gln Ile Met Pro Gly Arg Gln Glu Asn Leu Ile
        115                 120                 125
Asn Ala Val Ala Thr Asn Val Gly Ala Tyr Leu Asp Asp Thr Thr Ala
130                 135                 140
Arg Thr Ile Met Leu Ser Arg Ile Val Ser Leu Ala Arg Gly Asn Ser
145                 150                 155                 160
Ala Ile Thr Pro Ala Asn Leu Asp Lys Leu Val Ala Val Gln Ala Leu
                165                 170                 175
Ser Glu Ala Gly Val Glu Pro Met Glu Leu Ser Tyr Lys Asp Gly Leu
            180                 185                 190
Ala Leu Ile Asn Gly Thr Ser Gly Met Val Gly Leu Gly Thr Met Val
        195                 200                 205
Leu Gln Ala Ala Arg Arg Leu Val Asp Arg Tyr Leu Gln Val Ser Ala
210                 215                 220
Leu Ser Val Glu Gly Leu Ala Gly Met Thr Lys Pro Phe Asp Pro Arg
225                 230                 235                 240
Val His Gly Val Lys Pro His Arg Gly Gln Arg Gln Val Ala Ser Arg
                245                 250                 255
Leu Trp Glu Gly Leu Ala Asp Ser His Leu Ala Val Asn Glu Leu Asp
            260                 265                 270
Thr Glu Gln Thr Leu Ala Gly Glu Met Gly Thr Val Ala Lys Ala Gly
        275                 280                 285
Ser Leu Ala Ile Glu Asp Ala Tyr Ser Ile Arg Cys Thr Pro Gln Ile
290                 295                 300
Leu Gly Pro Val Val Asp Val Leu Asp Arg Ile Gly Ala Thr Leu Gln
305                 310                 315                 320
Asp Glu Leu Asn Ser Ser Asn Asp Asn Pro Ile Val Leu Pro Glu Glu
                325                 330                 335
Ala Glu Val Phe His Asn Gly His Phe His Gly Gln Tyr Val Ala Met
            340                 345                 350
Ala Met Asp His Leu Asn Met Ala Leu Ala Thr Val Thr Asn Leu Ala
        355                 360                 365
Asn Arg Arg Val Asp Arg Phe Leu Asp Lys Ser Asn Ser Asn Gly Leu
370                 375                 380
Pro Ala Phe Leu Cys Arg Glu Asp Pro Gly Leu Arg Leu Gly Leu Met
385                 390                 395                 400
Gly Gly Gln Phe Met Thr Ala Ser Ile Thr Ala Glu Thr Arg Thr Leu
                405                 410                 415
Thr Ile Pro Met Ser Val Gln Ser Leu Thr Ser Thr Ala Asp Phe Gln
            420                 425                 430
Asp Ile Val Ser Phe Gly Phe Val Ala Ala Arg Arg Ala Arg Glu Val
        435                 440                 445
```

```
Leu Thr Asn Ala Ala Tyr Val Ala Phe Glu Leu Cys Ala Cys
    450                 455                 460

Gln Ala Val Asp Ile Arg Gly Ala Asp Lys Leu Ser Ser Phe Thr Arg
465                 470                 475                 480

Pro Leu Tyr Glu Arg Thr Arg Lys Ile Val Pro Phe Phe Asp Arg Asp
                485                 490                 495

Glu Thr Ile Thr Asp Tyr Val Glu Lys Leu Ala Ala Asp Leu Ile Ala
                500                 505                 510

Gly Glu Pro Val Asp Ala Ala Val Ala Ala His
            515                 520
```

<210> SEQ ID NO 8
<211> LENGTH: 510
<212> TYPE: PRT
<213> ORGANISM: Pseudomonas putida

<400> SEQUENCE: 8

```
Met Thr Glu Leu Thr Leu Lys Pro Gly Thr Leu Thr Leu Ala Gln Leu
1               5                   10                  15

Arg Ala Ile His Ala Ala Pro Val Arg Leu Gln Leu Asp Ala Ser Ala
                20                  25                  30

Ala Pro Ala Ile Asp Ala Ser Val Ala Cys Val Glu Gln Ile Ile Ala
            35                  40                  45

Glu Asp Arg Thr Ala Tyr Gly Ile Asn Thr Gly Phe Gly Leu Leu Ala
        50                  55                  60

Ser Thr Arg Ile Ala Ser His Asp Leu Glu Asn Leu Gln Arg Ser Leu
65                  70                  75                  80

Val Leu Ser His Ala Ala Gly Ile Gly Ala Pro Leu Asp Asp Asp Leu
                85                  90                  95

Val Arg Leu Ile Met Val Leu Lys Ile Asn Ser Leu Ser Arg Gly Phe
            100                 105                 110

Ser Gly Ile Arg Arg Lys Val Ile Asp Ala Leu Ile Ala Leu Val Asn
        115                 120                 125

Ala Glu Val Tyr Pro His Ile Pro Leu Lys Gly Ser Val Gly Ala Ser
130                 135                 140

Gly Asp Leu Ala Pro Leu Ala Thr Met Ser Leu Val Leu Leu Gly Glu
145                 150                 155                 160

Gly Lys Ala Arg Tyr Lys Gly Gln Trp Leu Ser Ala Thr Glu Ala Leu
                165                 170                 175

Ala Val Ala Gly Leu Glu Pro Leu Thr Leu Ala Ala Lys Glu Gly Leu
            180                 185                 190

Ala Leu Leu Asn Gly Thr Gln Ala Ser Thr Ala Tyr Ala Leu Arg Gly
        195                 200                 205

Leu Phe Tyr Ala Glu Asp Leu Tyr Ala Ala Ile Ala Cys Gly Gly
    210                 215                 220

Leu Ser Val Glu Ala Val Leu Gly Ser Arg Ser Pro Phe Asp Ala Arg
225                 230                 235                 240

Ile His Glu Ala Arg Gly Gln Arg Gly Gln Ile Asp Thr Ala Ala Cys
                245                 250                 255

Phe Arg Asp Leu Leu Gly Asp Ser Ser Glu Val Ser Leu Ser His Lys
            260                 265                 270

Asn Cys Asp Lys Val Gln Asp Pro Tyr Ser Leu Arg Cys Gln Pro Gln
        275                 280                 285

Val Met Gly Ala Cys Leu Thr Gln Leu Arg Gln Ala Ala Glu Val Leu
```

-continued

```
                    290                 295                 300
Gly Ile Glu Ala Asn Ala Val Ser Asp Asn Pro Leu Val Phe Ala Ala
305                 310                 315                 320

Glu Gly Asp Val Ile Ser Gly Gly Asn Phe His Ala Glu Pro Val Ala
                325                 330                 335

Met Ala Ala Asp Asn Leu Ala Leu Ala Ile Ala Glu Ile Gly Ser Leu
                340                 345                 350

Ser Glu Arg Arg Ile Ser Leu Met Met Asp Lys His Met Ser Gln Leu
                355                 360                 365

Pro Pro Phe Leu Val Glu Asn Gly Gly Val Asn Ser Gly Phe Met Ile
370                 375                 380

Ala Gln Val Thr Ala Ala Ala Leu Ala Ser Glu Asn Lys Ala Leu Ser
385                 390                 395                 400

His Pro His Ser Val Asp Ser Leu Pro Thr Ser Ala Asn Gln Glu Asp
                405                 410                 415

His Val Ser Met Ala Pro Ala Ala Gly Lys Arg Leu Trp Glu Met Ala
                420                 425                 430

Glu Asn Thr Arg Gly Val Pro Ala Ile Glu Trp Leu Gly Ala Cys Gln
                435                 440                 445

Gly Leu Asp Leu Arg Lys Gly Leu Lys Thr Ser Ala Lys Leu Glu Lys
                450                 455                 460

Ala Arg Gln Ala Leu Arg Ser Glu Val Ala His Tyr Asp Arg Asp Arg
465                 470                 475                 480

Phe Phe Ala Pro Asp Ile Glu Lys Ala Val Glu Leu Leu Ala Lys Gly
                485                 490                 495

Ser Leu Thr Gly Leu Leu Pro Ala Gly Val Leu Pro Ser Leu
                500                 505                 510
```